(12) United States Patent
Fernandez-Salas et al.

(10) Patent No.: US 8,008,465 B2
(45) Date of Patent: Aug. 30, 2011

(54) NUCLEIC ACIDS ENCODING CHIMERA BOTULINUM TOXIN TYPE E

(75) Inventors: Ester Fernandez-Salas, Fullerton, CA (US); Lance E. Steward, Irvine, CA (US); Todd Herrington, Brookline, MA (US); K. Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 104 days.

(21) Appl. No.: 12/684,745

(22) Filed: Jan. 8, 2010

(65) Prior Publication Data

US 2010/0121042 A1    May 13, 2010

Related U.S. Application Data

(60) Division of application No. 11/036,532, filed on Jan. 14, 2005, now Pat. No. 7,691,983, which is a continuation-in-part of application No. 10/757,077, filed on Jan. 14, 2004, now Pat. No. 7,491,799, which is a continuation-in-part of application No. 10/163,106, filed on Jun. 4, 2002, now abandoned, which is a continuation-in-part of application No. 09/910,346, filed on Jul. 20, 2001, now abandoned, which is a continuation-in-part of application No. 09/620,840, filed on Jul. 21, 2000, now Pat. No. 6,903,187.

(51) Int. Cl.
    *C12N 15/31*    (2006.01)
(52) U.S. Cl. ..................................... 536/23.7
(58) Field of Classification Search .................. None
    See application file for complete search history.

(56) References Cited

U.S. PATENT DOCUMENTS

| | | | |
|---|---|---|---|
| 4,932,936 | A | 6/1990 | Dykstra et al. |
| 5,053,005 | A | 10/1991 | Borodic |
| 5,437,291 | A | 8/1995 | Pasricha et al. |
| 5,670,484 | A | 9/1997 | Binder |
| 5,714,468 | A | 2/1998 | Binder |
| 5,714,986 | A | 2/1998 | Dao |
| 5,721,215 | A | 2/1998 | Aoki et al. |
| 5,766,605 | A | 6/1998 | Sanders et al. |
| 5,939,070 | A | 8/1999 | Johnson et al. |
| 5,989,545 | A | 11/1999 | Foster et al. |
| 6,063,768 | A | 5/2000 | First |
| 6,113,915 | A | 9/2000 | Aoki et al. |
| 6,139,845 | A | 10/2000 | Donovan |
| 6,143,306 | A | 11/2000 | Donovan |
| 6,265,379 | B1 | 7/2001 | Donovan |
| 6,299,893 | B1 | 10/2001 | Schwartz et al. |
| 6,306,403 | B1 | 10/2001 | Donovan |
| 6,306,423 | B1 | 10/2001 | Donovan |
| 6,312,708 | B1 | 11/2001 | Donovan |
| 6,328,977 | B1 | 12/2001 | Donovan |
| 6,358,513 | B1 | 3/2002 | Voet et al. |
| 6,365,164 | B1 | 4/2002 | Schmidt |
| 6,395,277 | B1 | 5/2002 | Graham |
| 6,423,319 | B1 | 7/2002 | Brooks et al. |
| 6,458,365 | B1 | 10/2002 | Aoki et al. |
| 6,464,986 | B1 | 10/2002 | Aoki et al. |
| 6,903,187 | B1 | 6/2005 | Steward et al. |
| 7,393,925 | B2 | 7/2008 | Steward et al. |
| 7,491,799 | B2 | 2/2009 | Fernandez-Salas |
| 7,534,863 | B2 | 5/2009 | Fernandez-Salas |
| 2003/0027752 | A1 | 2/2003 | Steward et al. ................. 514/12 |
| 2003/0219462 | A1 | 11/2003 | Steward et al. ............ 424/239.1 |
| 2008/0177037 | A1 | 7/2008 | Steward et al. |
| 2008/0177041 | A1 | 7/2008 | Steward et al. |
| 2008/0177042 | A1 | 7/2008 | Steward et al. |
| 2008/0194797 | A1 | 8/2008 | Steward et al. |
| 2008/0214781 | A1 | 9/2008 | Steward et al. |
| 2009/0118475 | A1 | 5/2009 | Fernandaz-Salas |
| 2009/0202591 | A1 | 8/2009 | Fernandez-Salas |

FOREIGN PATENT DOCUMENTS

| | | |
|---|---|---|
| WO | WO94/15629 | 7/1994 |
| WO | WO 96/39166 | 12/1996 |
| WO | WO 97/32599 | 9/1997 |
| WO | WO98/08540 A1 | 3/1998 |
| WO | WO 00/05252 | 2/2000 |
| WO | WO 02/08268 A2 | 1/2002 |

OTHER PUBLICATIONS

Fernandez-Salas, E., et al., *Plasma membrane localization signals in the light chain of botulinum neurotoxin serotype A*, Society for Neuroscience Abstract Viewer and Itinerary Planner, vol. 2003; pp. Abstract No. 9.2.

Foran, Patrick G., et al., *Evaluation of the therapeutic usefulness of botulinum neurotoxin B, C1, E, and F compared with the long lasting type A. Basis for distinct durations of inhibition of exocytosis in central neurons*, Journal of Biological Chemistry, vol. 278, No. 2, Jan. 10, 2003, pp. 1363-1371.

Wang Xingmin, et al., *Genetic analysis of type E botulinum toxin-producing Clostridium butyricum strains*, Applied and Environmental Microbiology, vol. 66, No. 11, Nov. 2000, pp. 4992-4997.

Fernandez-Salas, E., et al., *Plasma membrane localization signals in the light chain of botulinum neurotoxin*, Proceedings of the National Academy of Sciences of the United States of America, Mar. 2, 2004, vol. 101, No. 9, pp. 3208-3213.

Adenis, et al., J. Fr. Ophthamol. (1990) 13:259-264, English Abstract only.

Binz, et al., J. Biol. Chem. (1990) 265:9153-9158.

Blitzer, et al., Ann. Otol. Rhinol Laryngol. (1985) 94:591-594.

Brin, et al., Advances in Neurology, vol. 50: Dystonia 2 (1988), pp. 599-608.

Cohn, et al., Neurology (1987) 37(3 Supp. 1):123-124, Abstract only.

Darsow, et al., J. Cell Biol. (1998) 142:913-922.

Elston, et al., Br. J. Opthamol. (1985) 69:718-724.

Elston, et al., Br. J. Opthamol. (1985) 69:891-896.

Galli, et al., Mol. Bio. Cell (1998) 9:1437-1448.

(Continued)

*Primary Examiner* — Robert C Hayes

(74) *Attorney, Agent, or Firm* — Kenton Abel; Debra Condino

(57) ABSTRACT

The present invention relates to a toxin comprising a modified light chain of a botulinum toxin type E, wherein the modified light chain comprises amino acid sequence PFVNKQFN (SEQ ID NO: 120) at the N-terminus, and amino acid sequence xExxxLL (SEQ ID NO: 112) at the C-terminus, wherein x is any amino acid.

12 Claims, 21 Drawing Sheets

OTHER PUBLICATIONS

Park and Simpson, "Inhalational poisoning by botulinium toxin and inhalation vaccination with its heavy-chain component," Infect. Immun. (2003) 71:1147-1154.

Atassi and Oshima, "Structure, activity and immune (T and B cell) recognition of botulinum neurotoxins," Crit. Rev. Immunol. (1999) 19:219-260.

Marchese Ragona, et al., "Management of parotid sialocele with botulinum toxin," The Laryngoscope (1999) 109:1344-1346.

Wiegand, et al., "125-I labelled botulinum A neurotoxin: pharmacokinetics in cats after intramuscular injection," Naunyn-Schmiedeberg's Arch. Pharmacol. (1976) 292:161-165.

Habermann, "125-I labeled neurotoxin from *Clostridium botulinum* A: preparation, bindng to synaptosomes and ascent to the spinal cord," Naunyn-Schmiedeberg's Arch. Pharmacol. (1974) 281:47-56.

Moyer, et al., "Botulinum Toxin Type B: Experimental and Clinical Experience," in Therapy with Botlinum Toxin, Jankovic, ed., 1994, pp. 71-84.

Gonelle-Gispert, "SNAP-25a and -25b isoforms are both expressed in insulin secreting cells and can function in insulin secretion," Biochem. J. (1999) 339:159-165.

International Conference on Botulinum Toxin: Basic Science and Clinical Therapeutics, Mov. Disord. (1995) 10:361-408.

Haberman, et al., "Tetanus toxin and botulinum A and C neurotoxins inhibit noradrenaline release from cultured mouse brain," J. Neurochem. (1988) 51:522-527.

Sanchez-Prieto, et al., "Botulinum toxin A blocks glutamate exocytosis from guinea pig cerebral cortical synaptosomes," Eur. J. Biochem. (1987) 165:675-681.

Pearce, "Pharmacologic characterization of botuinum toxin for basic science and medicine," Toxicon, 35:1373-1412, (1997).

Zhou, et al., Biochemistry (1995) 34:15175-15181.

Shin, et al., J. Biol. Chem. (1991) 266:10658-10665.

Raciborska and Charlton, Can. J. Physiol. (1999) 77:679-688.

Erdal, et al., Arch. Pharmacol. (1995) 351:67-78.

Naumann, et al., Eur. J. Neurol. (1999) 6:S111-S115.

Keller, et al., FEBS Lett. (1999) 456:137-142.

Dietrich, et al., J. Cell. Biol. (1997) 138:271-281.

Geisler, et al., J. Biol. Chem. (1998) 273:21316-21323.

Tan, et al., J. Biol. Chem. (1998) 273:17351-17360.

Liu, et al., Trends Cell Biol. (1999) 9:356-363.

Cai and Singh, Biochemistry (2001) 40:4693.

Tikkanen, et al., Traffic (2000) 1:631-640.

Rapaport, et al., EMBO J. (1998) 17:2148-2155.

Cowles, et al., Cell (1997) 91:109-118.

Aoki, et al., J. Neurol. (2001) 248 (Supp 1):3-10.

Aoki, Toxicon. (2001) 12:1815-1820.

Thompson, et al., Eur. J. Biochem. (1990) 189:73.

Cenci Di Bello, et al., Eur. J. Biochem. (1994) 219:161-169.

Arnon, et al., "Botulinum toxin as a biological weapon: medical and public health management," JAMA (2001) 285:1059-1070.

Eswaramoorthy, et al., "A novel mechanism for *Clostridium botulinum* neurotoxin inhibition," Biochemistry (2002)41:9795-9802.

Aoki, et al., "Is the light chain subcellular localization an important factor for Botulinum neurotoxin duration of action?," Naunyn Schmiedebergs Arch. Pharmacol. (2002) 365 (Suppl 2):R10.

Fernandez-Salas, et al., "Localization of BoNT light chains in neuronal and non-neuronal cell lines, implications for the duration of action of the different serotypes," Naunyn Schmiedebergs Arch. Pharmacol. (2002) 365 (Suppl 2):R19.

Steward, et al., "BoNT/A light chain and the dileucine motif: potential implications for light chain localization and neurotoxin duration of action," Naunyn Schmiedebergs Arch. Pharmacol. (2002) 365 (Suppl 2):R44.

Jancovic, et al., Neurology (1987) 37:616-623.

Kadkhodayan, et al., Protein Express. Purif. (2000) 19:125-130.

Kozaki, et al., J. Med. Sci. Biol. (1981) 34:61-68.

Lacy, et al., Nat. Struct. Biol. (1998) 5:898-902.

Li, et al., Biochemistry (1994) 33:7014-7020.

Maisey, et al., Eur. J. Biochem. (1988) 177:683-691.

Martinez-Arca, et al., J. Cell Biol. (2000) 149:889-899.

Milton, et al., Biochemistry (1992) 31:8799-8809.

Minton, Molecular genetics of Clostridial Neurotoxins, Montecucco C. (Ed.) Clostridial Neurotoxins in the molecular pathogenesis of tetanus and botulism, Berlin; NY: Springer Verlag, 1995, pp. 161-194.

Peden, et al., J. Biol. Chem. (2001) 276:49183-49187.

Swain, et al., Peptide Res. (1993) 6:147-154.

Dong, et al., PNAS, 101(41): 14701-14706, 2004.

Fernandez-Salas, et al., PNAS 101:3208-3213, 2004.

Fernandez-Salas, et al., "Plasma membrane signals in the light chain of Botulinum neurotoxin," slide presentation at USAMRDD, Jan. 2004.

Fernandez-Salas, et al., "Is the light chain subcellular localization an important factor in Botulinum toxin duration of action?" Movement Disorders (2004) 19:S23-S34.

Schantz, et al., Properties and use of Botulinum toxin and other microbial neurotoxins in medicine, Microbiological Reviews, Mar. 1992, vol. 56, No. 1, pp. 80-99.

Rudinger, "Characteristics of the amino acids as components of a peptide hormone sequence," 1976, Parson, Ed., Peptide Hormones, University Park Press, pp. 1-7.

Zhou et al, "Expression and purification of the light chain of botulinum neurotoxin A: A single mutation abolishes its cleavage of SNAP-25 and neurotoxicity after reconstruction with the heavy chain", Biochemistry, vol. 34, No. 46, pp. 15175-15181, 1995.

```
                    1                   19
rLC/A      (1)  MPFVNKQFNYKDPVNGVDI
dN-LC/A    (1)  --------MYKDPVNGVDI
LC/B       (1)  MPVTINNFNYNDPIDNNNI
LC/E       (1)  -MPKINSFNYNDPVNDRTI
Consensus  (1)  MP   INNFNYNDPVNGVDI
```

Figure 1

```
                                    (396) 396        410        420        430        44
              BoNT-A_HallA_LC (394) TNLAANFNGQNTEINNMNFKLKNFTGLEFYKLLVRGIITSK--
        Translation of LCE (NTP genomic) (378) -NL...
                  BoNT-E_Beluga (379) -NL...
Translation of pET-28a(+)-His6-synth LC/E (377) -NL...
              BoNT-E_NCTC11219 (379) -NL...
     Translation of pQBI25fC3 Dolly LCE (378) -NL...
                      Consensus (396) NLKVNFRGQNANLNPRIITPIT   GRLVKKLIRFCKNIVSVKG
```

Figure 2

Figure 14-a: Sequence of wild-type Beluga LC/E (SEQ ID NO: 136/137)

```
           T   T   K       Y   T   I       T   Q   K       Q   N   P       L   I   T
    679 ACTACAAAG TATACTATA ACACAAAAA CAAAATCCC CTAATAACA
        TGATGTTTC ATATGATAT TGTGTTTTT GTTTTAGGG GATTATTGT
           N   I   R       G   T   N       I   E   E       F   L   T       F   G   G
    724 AATATAAGA GGTACAAAT ATTGAAGAA TTCTTAACT TTTGGAGGT
        TTATATTCT CCATGTTTA TAACTTCTT AAGAATTGA AAACCTCCA
           T   D   L       N   I   I       T   S   A       Q   S   N       D   I   Y
    769 ACTGATTTA AACATTATT ACTAGTGCT CAGTCCAAT GATATCTAT
        TGACTAAAT TTGTAATAA TGATCACGA GTCAGGTTA CTATAGATA
           T   N   L       L   A   D       Y   K   K       I   A   S       K   L   S
    814 ACTAATCTT CTAGCTGAT TATAAAAAA ATAGCGTCT AAACTTAGC
        TGATTAGAA GATCGACTA ATATTTTTT TATCGCAGA TTTGAATCG
           K   V   Q       V   S   N       P   L   L       N   P   Y       K   D   V
    859 AAAGTACAA GTATCTAAT CCACTACTT AATCCTTAT AAAGATGTT
        TTTCATGTT CATAGATTA GGTGATGAA TTAGGAATA TTTCTACAA
           F   E   A       K   Y   G       L   D   K       D   A   S       G   I   Y
    904 TTTGAAGCA AAGTATGGA TTAGATAAA GATGCTAGC GGAATTTAT
        AAACTTCGT TTCATACCT AATCTATTT CTACGATCG CCTTAAATA
           S   V   N       I   N   K       F   N   D       I   F   K       K   L   Y
    949 TCGGTAAAT ATAAACAAA TTTAATGAT ATTTTTAAA AAATTATAC
        AGCCATTTA TATTTGTTT AAATTACTA TAAAAATTT TTTAATATG
           S   F   T       E   F   D       L   A   T       K   F   Q       V   K   C
    994 AGCTTTACG GAATTTGAT TTAGCAACT AAATTTCAA GTTAAATGT
        TCGAAATGC CTTAAACTA AATCGTTGA TTTAAAGTT CAATTTACA
           R   Q   T       Y   I   G       Q   Y   K       Y   F   K       L   S   N
   1039 AGGCAAACT TATATTGGA CAGTATAAA TACTTCAAA CTTTCAAAC
        TCCGTTTGA ATATAACCT GTCATATTT ATGAAGTTT GAAAGTTTG
           L   L   N       D   S   I       Y   N   I       S   E   G       Y   N   I
   1084 TTGTTAAAT GATTCTATT TATAATATA TCAGAAGGC TATAATATA
        AACAATTTA CTAAGATAA ATATTATAT AGTCTTCCG ATATTATAT
           N   N   L       K   V   N       F   R   G       Q   N   A       N   L   N
   1129 AATAATTTA AAGGTAAAT TTTAGAGGA CAGAATGCA AATTTAAAT
        TTATTAAAT TTCCATTTA AAATCTCCT GTCTTACGT TTAAATTTA
           P   R   I       I   T   P       I   T   G       R   G   L       V   K   K
   1174 CCTAGAATT ATTACACCA ATTACAGGT AGAGGACTA GTAAAAAAA
        GGATCTTAA TAATGTGGT TAATGTCCA TCTCCTGAT CATTTTTTT
           I   I   R       F   C   K       N   I   V       S   V   K       G   I   R
   1219 ATCATTAGA TTTTGTAAA AATATTGTT TCTGTAAAA GGCATAAGG
        TAGTAATCT AAAACATTT TTATAACAA AGACATTTT CCGTATTCC
           K   L   R
   1264 AAGCTTCGC
        TTCGAAGCG
```

Figure 15-a: Sequence of chimera LC/E with N-terminus of LC/A
(SEQ ID NO: 138/139)

```
        P   F   V     N   K   Q     F   N   Y     N   D   P     V   N   D
  1   CCATTTGTT   AATAAACAG   TTTAATTAT   AATGATCCT   GTTAATGAT
      GGTAAACAA   TTATTTGTC   AAATTAATA   TTACTAGGA   CAATTACTA
        R   T   I     L   Y   I     K   P   G     G   C   Q     E   F   Y
 46   AGAACAATT   TTATATATT   AAACCAGGC   GGTTGTCAA   GAATTTTAT
      TCTTGTTAA   AATATATAA   TTTGGTCCG   CCAACAGTT   CTTAAAATA
        K   S   F     N   I   M     K   N   I     W   I   I     P   E   R
 91   AAATCATTT   AATATTATG   AAAAATATT   TGGATAATT   CCAGAGAGA
      TTTAGTAAA   TTATAATAC   TTTTTATAA   ACCTATTAA   GGTCTCTCT
        N   V   I     G   T   T     P   Q   D     F   H   P     P   T   S
136   AATGTAATT   GGTACAACC   CCCCAAGAT   TTTCATCCG   CCTACTTCA
      TTACATTAA   CCATGTTGG   GGGGTTCTA   AAAGTAGGC   GGATGAAGT
        L   K   N     G   D   S     S   Y   Y     D   P   N     Y   L   Q
181   TTAAAAAAT   GGAGATAGT   AGTTATTAT   GACCCTAAT   TATTTACAA
      AATTTTTTA   CCTCTATCA   TCAATAATA   CTGGGATTA   ATAAATGTT
        S   D   E     E   K   D     R   F   L     K   I   V     T   K   I
226   AGTGATGAA   GAAAAGGAT   AGATTTTTA   AAAATAGTC   ACAAAAATA
      TCACTACTT   CTTTTCCTA   TCTAAAAAT   TTTTATCAG   TGTTTTTAT
        F   N   R     I   N   N     N   L   S     G   G   I     L   L   E
271   TTTAATAGA   ATAAATAAT   AATCTTTCA   GGAGGGATT   TTATTAGAA
      AAATTATCT   TATTTATTA   TTAGAAAGT   CCTCCCTAA   AATAATCTT
        E   L   S     K   A   N     P   Y   L     G   N   D     N   T   P
316   GAACTGTCA   AAAGCTAAT   CCATATTTA   GGGAATGAT   AATACTCCA
      CTTGACAGT   TTTCGATTA   GGTATAAAT   CCCTTACTA   TTATGAGGT
        D   N   Q     F   H   I     G   D   A     S   A   V     E   I   K
361   GATAATCAA   TTCCATATT   GGTGATGCA   TCAGCAGTT   GAGATTAAA
      CTATTAGTT   AAGGTATAA   CCACTACGT   AGTCGTCAA   CTCTAATTT
        F   S   N     G   S   Q     D   I   L     L   P   N     V   I   I
406   TTCTCAAAT   GGTAGCCAA   GACATACTA   TTACCTAAT   GTTATTATA
      AAGAGTTTA   CCATCGGTT   CTGTATGAT   AATGGATTA   CAATAATAT
        M   G   A     E   P   D     L   F   E     T   N   S     S   N   I
451   ATGGGAGCA   GAGCCTGAT   TTATTTGAA   ACTAACAGT   TCCAATATT
      TACCCTCGT   CTCGGACTA   AATAAACTT   TGATTGTCA   AGGTTATAA
        S   L   R     N   N   Y     M   P   S     N   H   G     F   G   S
496   TCTCTAAGA   AATAATTAT   ATGCCAAGC   AATCACGGT   TTTGGATCA
      AGAGATTCT   TTATTAATA   TACGGTTCG   TTAGTGCCA   AAACCTAGT
        I   A   I     V   T   F     S   P   E     Y   S   F     R   F   N
541   ATAGCTATA   GTAACATTC   TCACCTGAA   TATTCTTTT   AGATTTAAT
      TATCGATAT   CATTGTAAG   AGTGGACTT   ATAAGAAAA   TCTAAATTA
        D   N   S     M   N   E     F   I   Q     D   P   A     L   T   L
586   GATAATAGT   ATGAATGAA   TTTATTCAA   GATCCTGCT   CTTACATTA
      CTATTATCA   TACTTACTT   AAATAAGTT   CTAGGACGA   GAATGTAAT
        M   H   E     L   I   H     S   L   H     G   L   Y     G   A   K
631   ATGCATGAA   TTAATACAT   TCATTACAT   GGACTATAT   GGGGCTAAA
      TACGTACTT   AATTATGTA   AGTAATGTA   CCTGATATA   CCCCGATTT
```

Figure 15-b

```
            G   I   T     T   K   Y     T   I   T     Q   K   Q     N   P   L
 676    GGGATTACT   ACAAAGTAT   ACTATAACA   CAAAAACAA   AATCCCCTA
        CCCTAATGA   TGTTTCATA   TGATATTGT   GTTTTTGTT   TTAGGGGAT
            I   T   N     I   R   G     T   N   I     E   E   F     L   T   F
 721    ATAACAAAT   ATAAGAGGT   ACAAATATT   GAAGAATTC   TTAACTTTT
        TATTGTTTA   TATTCTCCA   TGTTTATAA   CTTCTTAAG   AATTGAAAA
            G   G   T     D   L   N     I   I   T     S   A   Q     S   N   D
 766    GGAGGTACT   GATTTAAAC   ATTATTACT   AGTGCTCAG   TCCAATGAT
        CCTCCATGA   CTAAATTTG   TAATAATGA   TCACGAGTC   AGGTTACTA
            I   Y   T     N   L   L     A   D   Y     K   K   I     A   S   K
 811    ATCTATACT   AATCTTCTA   GCTGATTAT   AAAAAAATA   GCGTCTAAA
        TAGATATGA   TTAGAAGAT   CGACTAATA   TTTTTTTAT   CGCAGATTT
            L   S   K     V   Q   V     S   N   P     L   L   N     P   Y   K
 856    CTTAGCAAA   GTACAAGTA   TCTAATCCA   CTACTTAAT   CCTTATAAA
        GAATCGTTT   CATGTTCAT   AGATTAGGT   GATGAATTA   GGAATATTT
            D   V   F     E   A   K     Y   G   L     D   K   D     A   S   G
 901    GATGTTTTT   GAAGCAAAG   TATGGATTA   GATAAAGAT   GCTAGCGGA
        CTACAAAAA   CTTCGTTTC   ATACCTAAT   CTATTTCTA   CGATCGCCT
            I   Y   S     V   N   I     N   K   F     N   D   I     F   K   K
 946    ATTTATTCG   GTAAATATA   AACAAATTT   AATGATATT   TTTAAAAAA
        TAAATAAGC   CATTTATAT   TTGTTTAAA   TTACTATAA   AAATTTTTT
            L   Y   S     F   T   E     F   D   L     A   T   K     F   Q   V
 991    TTATACAGC   TTTACGGAA   TTTGATTTA   GCAACTAAA   TTTCAAGTT
        AATATGTCG   AAATGCCTT   AAACTAAAT   CGTTGATTT   AAAGTTCAA
            K   C   R     Q   T   Y     I   G   Q     Y   K   Y     F   K   L
1036    AAATGTAGG   CAAACTTAT   ATTGGACAG   TATAAATAC   TTCAAACTT
        TTTACATCC   GTTTGAATA   TAACCTGTC   ATATTTATG   AAGTTTGAA
            S   N   L     L   N   D     S   I   Y     N   I   S     E   G   Y
1081    TCAAACTTG   TTAAATGAT   TCTATTTAT   AATATATCA   GAAGGCTAT
        AGTTTGAAC   AATTTACTA   AGATAAATA   TTATATAGT   CTTCCGATA
            N   I   N     N   L   K     V   N   F     R   G   Q     N   A   N
1126    AATATAAAT   AATTTAAAG   GTAAATTTT   AGAGGACAG   AATGCAAAT
        TTATATTTA   TTAAATTTC   CATTTAAAA   TCTCCTGTC   TTACGTTTA
            L   N   P     R   I   I     T   P   I     T   G   R     G   L   V
1171    TTAAATCCT   AGAATTATT   ACACCAATT   ACAGGTAGA   GGACTAGTA
        AATTTAGGA   TCTTAATAA   TGTGGTTAA   TGTCCATCT   CCTGATCAT
            K   K   I     I   R   F     C   K   N     I   V   S     V   K   G
1216    AAAAAAATC   ATTAGATTT   TGTAAAAAT   ATTGTTTCT   GTAAAAGGC
        TTTTTTTAG   TAATCTAAA   ACATTTTTA   TAACAAAGA   CATTTTCCG
            I   R   K     L   R
1261    ATAAGGAAG   CTTCGC
        TATTCCTTC   GAAGCG
```

Figure 16-a: Sequence of chimera LC/E with LC/A di-leucine motif at C-terminus (SEQ ID NO: 140/141)

```
          P   K   I   N   S   F   N   Y   N   D   P   V   N   D   R   T
1       CCA AAAATTAAT AGTTTTAAT TATAATGAT CCTGTTAAT GATAGAACA
        GGT TTTTAATTA TCAAAATTA ATATTACTA GGACAATTA CTATCTTGT
          I   L   Y   I   K   P   G   G   C   Q   E   F   Y   K   S
49          ATTTTATAT ATTAAACCA GGCGGTTGT CAAGAATTT TATAAATCA
            TAAAATATA TAATTTGGT CCGCCAACA GTTCTTAAA ATATTTAGT
          F   N   I   M   K   N   I   W   I   P   E   R   N   V
94          TTTAATATT ATGAAAAAT ATTTGGATA ATTCCAGAG AGAAATGTA
            AAATTATAA TACTTTTTA TAAACCTAT TAAGGTCTC TCTTTACAT
          I   G   T   T   P   Q   D   F   H   P   P   T   S   L   K
139         ATTGGTACA ACCCCCCAA GATTTTCAT CCGCCTACT TCATTAAAA
            TAACCATGT TGGGGGGTT CTAAAAGTA GGCGGATGA AGTAATTTT
          N   G   D   S   S   Y   Y   D   P   N   Y   L   Q   S   D
184         AATGGAGAT AGTAGTTAT TATGACCCT AATTATTTA CAAAGTGAT
            TTACCTCTA TCATCAATA ATACTGGGA TTAATAAAT GTTTCACTA
          E   E   K   D   R   F   L   K   I   V   T   K   I   F   N
229         GAAGAAAAG GATAGATTT TTAAAAATA GTCACAAAA ATATTTAAT
            CTTCTTTTC CTATCTAAA AATTTTTAT CAGTGTTTT TATAAATTA
          R   I   N   N   L   S   G   G   I   L   L   E   E   L
274         AGAATAAAT AATAATCTT TCAGGAGGG ATTTTATTA GAAGAACTG
            TCTTATTTA TTATTAGAA AGTCCTCCC TAAAATAAT CTTCTTGAC
          S   K   A   N   P   Y   L   G   N   D   N   T   P   D   N
319         TCAAAAGCT AATCCATAT TTAGGGAAT GATAATACT CCAGATAAT
            AGTTTTCGA TTAGGTATA AATCCCTTA CTATTATGA GGTCTATTA
          Q   F   H   I   G   D   A   S   A   V   E   I   K   F   S
364         CAATTCCAT ATTGGTGAT GCATCAGCA GTTGAGATT AAATTCTCA
            GTTAAGGTA TAACCACTA CGTAGTCGT CAACTCTAA TTTAAGAGT
          N   G   S   Q   D   I   L   L   P   N   V   I   I   M   G
409         AATGGTAGC CAAGACATA CTATTACCT AATGTTATT ATAATGGGA
            TTACCATCG GTTCTGTAT GATAATGGA TTACAATAA TATTACCCT
          A   E   P   D   L   F   E   T   N   S   S   N   I   S   L
454         GCAGAGCCT GATTTATTT GAAACTAAC AGTTCCAAT ATTTCTCTA
            CGTCTCGGA CTAAATAAA CTTTGATTG TCAAGGTTA TAAAGAGAT
          R   N   N   Y   M   P   S   N   H   G   F   G   S   I   A
499         AGAAATAAT TATATGCCA AGCAATCAC GGTTTTGGA TCAATAGCT
            TCTTTATTA ATATACGGT TCGTTAGTG CCAAAACCT AGTTATCGA
          I   V   T   F   S   P   E   Y   S   F   R   F   N   D   N
544         ATAGTAACA TTCTCACCT GAATATTCT TTTAGATTT AATGATAAT
            TATCATTGT AAGAGTGGA CTTATAAGA AAATCTAAA TTACTATTA
          S   M   N   E   F   I   Q   D   P   A   L   T   L   M   H
589         AGTATGAAT GAATTTATT CAAGATCCT GCTCTTACA TTAATGCAT
            TCATACTTA CTTAAATAA GTTCTAGGA CGAGAATGT AATTACGTA
          E   L   I   H   S   L   H   G   L   Y   G   A   K   G   I
634         GAATTAATA CATTCATTA CATGGACTA TATGGGGCT AAAGGGATT
```

Figure 16-b

```
             CTTAATTAT  GTAAGTAAT  GTACCTGAT  ATACCCCGA  TTTCCCTAA
             T  T  K    Y  T  I    T  Q  K    Q  N  P    L  I  T
    679      ACTACAAAG  TATACTATA  ACACAAAAA  CAAAATCCC  CTAATAACA
             TGATGTTTC  ATATGATAT  TGTGTTTTT  GTTTTAGGG  GATTATTGT
             N  I  R    G  T  N    I  E  E    F  L  T    F  G  G
    724      AATATAAGA  GGTACAAAT  ATTGAAGAA  TTCTTAACT  TTTGGAGGT
             TTATATTCT  CCATGTTTA  TAACTTCTT  AAGAATTGA  AAACCTCCA
             T  D  L    N  I  I    T  S  A    Q  S  N    D  I  Y
    769      ACTGATTTA  AACATTATT  ACTAGTGCT  CAGTCCAAT  GATATCTAT
             TGACTAAAT  TTGTAATAA  TGATCACGA  GTCAGGTTA  CTATAGATA
             T  N  L    L  A  D    Y  K  K    I  A  S    K  L  S
    814      ACTAATCTT  CTAGCTGAT  TATAAAAAA  ATAGCGTCT  AAACTTAGC
             TGATTAGAA  GATCGACTA  ATATTTTTT  TATCGCAGA  TTTGAATCG
             K  V  Q    V  S  N    P  L  L    N  P  Y    K  D  V
    859      AAAGTACAA  GTATCTAAT  CCACTACTT  AATCCTTAT  AAAGATGTT
             TTTCATGTT  CATAGATTA  GGTGATGAA  TTAGGAATA  TTTCTACAA
             F  E  A    K  Y  G    L  D  K    D  A  S    G  I  Y
    904      TTTGAAGCA  AAGTATGGA  TTAGATAAA  GATGCTAGC  GGAATTTAT
             AAACTTCGT  TTCATACCT  AATCTATTT  CTACGATCG  CCTTAAATA
             S  V  N    I  N  K    F  N  D    I  F  K    K  L  Y
    949      TCGGTAAAT  ATAAACAAA  TTTAATGAT  ATTTTTAAA  AAATTATAC
             AGCCATTTA  TATTTGTTT  AAATTACTA  TAAAAATTT  TTTAATATG
             S  F  T    E  F  D    L  A  T    K  F  Q    V  K  C
    994      AGCTTTACG  GAATTTGAT  TTAGCAACT  AAATTTCAA  GTTAAATGT
             TCGAAATGC  CTTAAACTA  AATCGTTGA  TTTAAAGTT  CAATTTACA
             R  Q  T    Y  I  G    Q  Y  K    Y  F  K    L  S  N
   1039      AGGCAAACT  TATATTGGA  CAGTATAAA  TACTTCAAA  CTTTCAAAC
             TCCGTTTGA  ATATAACCT  GTCATATTT  ATGAAGTTT  GAAAGTTTG
             L  L  N    D  S  I    Y  N  I    S  E  G    Y  N  I
   1084      TTGTTAAAT  GATTCTATT  TATAATATA  TCAGAAGGC  TATAATATA
             AACAATTTA  CTAAGATAA  ATATTATAT  AGTCTTCCG  ATATTATAT
             N  N  L    K  V  N    F  R  G    Q  N  A    N  L  N
   1129      AATAATTTA  AAGGTAAAT  TTTAGAGGA  CAGAATGCA  AATTTAAAT
             TTATTAAAT  TTCCATTTA  AAATCTCCT  GTCTTACGT  TTAAATTTA
             P  R  I    I  T  P    I  T  G    R  G  E    V  K  K
   1174      CCTAGAATT  ATTACACCA  ATTACAGGT  AGAGGAGAA  GTAAAAAAA
             GGATCTTAA  TAATGTGGT  TAATGTCCA  TCTCCTCTT  CATTTTTTT
             L  L  R    F  C  K    N  I  V    S  V  K    G  I  R
   1219      CTCCTTAGA  TTTTGTAAA  AATATTGTT  TCTGTAAAA  GGCATAAGG
             GAGGAATCT  AAAACATTT  TTATAACAA  AGACATTTT  CCGTATTCC
             K  L  R
   1265      AAGCTTCGC
             TTCGAAGCG
```

Figure 17-a: Sequence of chimera LC/E with LC/A N-terminus and C-terminal di-leucine motif (SEQ ID NO: 142/143)

```
         P   F   V    N   K   Q    F   N   Y    N   D   P    V   N   D
  1    CCATTTGTT  AATAAACAG  TTTAATTAT  AATGATCCT  GTTAATGAT
       GGTAAACAA  TTATTTGTC  AAATTAATA  TTACTAGGA  CAATTACTA
         R   T   I    L   Y   I    K   P   G    G   C   Q    E   F   Y
 46    AGAACAATT  TTATATATT  AAACCAGGC  GGTTGTCAA  GAATTTTAT
       TCTTGTTAA  AATATATAA  TTTGGTCCG  CCAACAGTT  CTTAAAATA
         K   S   F    N   I   M    K   N   I    W   I   I    P   E   R
 91    AAATCATTT  AATATTATG  AAAAATATT  TGGATAATT  CCAGAGAGA
       TTTAGTAAA  TTATAATAC  TTTTTATAA  ACCTATTAA  GGTCTCTCT
         N   V   I    G   T   T    P   Q   D    F   H   P    P   T   S
136    AATGTAATT  GGTACAACC  CCCCAAGAT  TTTCATCCG  CCTACTTCA
       TTACATTAA  CCATGTTGG  GGGGTTCTA  AAAGTAGGC  GGATGAAGT
         L   K   N    G   D   S    S   Y   Y    D   P   N    Y   L   Q
181    TTAAAAAAT  GGAGATAGT  AGTTATTAT  GACCCTAAT  TATTTACAA
       AATTTTTTA  CCTCTATCA  TCAATAATA  CTGGGATTA  ATAAATGTT
         S   D   E    E   K   D    R   F   L    K   I   V    T   K   I
226    AGTGATGAA  GAAAAGGAT  AGATTTTTA  AAAATAGTC  ACAAAAATA
       TCACTACTT  CTTTTCCTA  TCTAAAAAT  TTTTATCAG  TGTTTTTAT
         F   N   R    I   N   N    N   L   S    G   G   I    L   L   E
271    TTTAATAGA  ATAAATAAT  AATCTTTCA  GGAGGGATT  TTATTAGAA
       AAATTATCT  TATTTATTA  TTAGAAAGT  CCTCCCTAA  AATAATCTT
         E   L   S    K   A   N    P   Y   L    G   N   D    N   T   P
316    GAACTGTCA  AAAGCTAAT  CCATATTTA  GGGAATGAT  AATACTCCA
       CTTGACAGT  TTTCGATTA  GGTATAAAT  CCCTTACTA  TTATGAGGT
         D   N   Q    F   H   I    G   D   A    S   A   V    E   I   K
361    GATAATCAA  TTCCATATT  GGTGATGCA  TCAGCAGTT  GAGATTAAA
       CTATTAGTT  AAGGTATAA  CCACTACGT  AGTCGTCAA  CTCTAATTT
         F   S   N    G   S   Q    D   I   L    L   P   N    V   I   I
406    TTCTCAAAT  GGTAGCCAA  GACATACTA  TTACCTAAT  GTTATTATA
       AAGAGTTTA  CCATCGGTT  CTGTATGAT  AATGGATTA  CAATAATAT
         M   G   A    E   P   D    L   F   E    T   N   S    S   N   I
451    ATGGGAGCA  GAGCCTGAT  TTATTTGAA  ACTAACAGT  TCCAATATT
       TACCCTCGT  CTCGGACTA  AATAAACTT  TGATTGTCA  AGGTTATAA
         S   L   R    N   N   Y    M   P   S    N   H   G    F   G   S
496    TCTCTAAGA  AATAATTAT  ATGCCAAGC  AATCACGGT  TTTGGATCA
       AGAGATTCT  TTATTAATA  TACGGTTCG  TTAGTGCCA  AAACCTAGT
         I   A   I    V   T   F    S   P   E    Y   S   F    R   F   N
541    ATAGCTATA  GTAACATTC  TCACCTGAA  TATTCTTTT  AGATTTAAT
       TATCGATAT  CATTGTAAG  AGTGGACTT  ATAAGAAAA  TCTAAATTA
         D   N   S    M   N   E    F   I   Q    D   P   A    L   T   L
586    GATAATAGT  ATGAATGAA  TTTATTCAA  GATCCTGCT  CTTACATTA
       CTATTATCA  TACTTACTT  AAATAAGTT  CTAGGACGA  GAATGTAAT
         M   H   E    L   I   H    S   L   H    G   L   Y    G   A   K
631    ATGCATGAA  TTAATACAT  TCATTACAT  GGACTATAT  GGGGCTAAA
```

Figure 17-b

```
                  TACGTACTT  AATTATGTA  AGTAATGTA  CCTGATATA  CCCCGATTT
                   G  I  T    T  K  Y    T  I  T    Q  K  Q    N  P  L
         676  GGGATTACT  ACAAAGTAT  ACTATAACA  CAAAAACAA  AATCCCCTA
              CCCTAATGA  TGTTTCATA  TGATATTGT  GTTTTTGTT  TTAGGGGAT
                I  T  N    I  R  G    T  N  I    E  E  F    L  T  F
         721  ATAACAAAT  ATAAGAGGT  ACAAATATT  GAAGAATTC  TTAACTTTT
              TATTGTTTA  TATTCTCCA  TGTTTATAA  CTTCTTAAG  AATTGAAAA
                G  G  T    D  L  N    I  I  T    S  A  Q    S  N  D
         766  GGAGGTACT  GATTTAAAC  ATTATTACT  AGTGCTCAG  TCCAATGAT
              CCTCCATGA  CTAAATTTG  TAATAATGA  TCACGAGTC  AGGTTACTA
                I  Y  T    N  L  L    A  D  Y    K  K  I    A  S  K
         811  ATCTATACT  AATCTTCTA  GCTGATTAT  AAAAAAATA  GCGTCTAAA
              TAGATATGA  TTAGAAGAT  CGACTAATA  TTTTTTTAT  CGCAGATTT
                L  S  K    V  Q  V    S  N  P    L  L  N    P  Y  K
         856  CTTAGCAAA  GTACAAGTA  TCTAATCCA  CTACTTAAT  CCTTATAAA
              GAATCGTTT  CATGTTCAT  AGATTAGGT  GATGAATTA  GGAATATTT
                D  V  F    E  A  K    Y  G  L    D  K  D    A  S  G
         901  GATGTTTTT  GAAGCAAAG  TATGGATTA  GATAAAGAT  GCTAGCGGA
              CTACAAAAA  CTTCGTTTC  ATACCTAAT  CTATTTCTA  CGATCGCCT
                I  Y  S    V  N  I    N  K  F    N  D  I    F  K  K
         946  ATTTATTCG  GTAAATATA  AACAAATTT  AATGATATT  TTTAAAAAA
              TAAATAAGC  CATTTATAT  TTGTTTAAA  TTACTATAA  AAATTTTTT
                L  Y  S    F  T  E    F  D  L    A  T  K    F  Q  V
         991  TTATACAGC  TTTACGGAA  TTTGATTTA  GCAACTAAA  TTTCAAGTT
              AATATGTCG  AAATGCCTT  AAACTAAAT  CGTTGATTT  AAAGTTCAA
                K  C  R    Q  T  Y    I  G  Q    Y  K  Y    F  K  L
        1036  AAATGTAGG  CAAACTTAT  ATTGGACAG  TATAAATAC  TTCAAACTT
              TTTACATCC  GTTTGAATA  TAACCTGTC  ATATTTATG  AAGTTTGAA
                S  N  L    L  N  D    S  I  Y    N  I  S    E  G  Y
        1081  TCAAACTTG  TTAAATGAT  TCTATTTAT  AATATATCA  GAAGGCTAT
              AGTTTGAAC  AATTTACTA  AGATAAATA  TTATATAGT  CTTCCGATA
                N  I  N    N  L  K    V  N  F    R  G  Q    N  A  N
        1126  AATATAAAT  AATTTAAAG  GTAAATTTT  AGAGGACAG  AATGCAAAT
              TTATATTTA  TTAAATTTC  CATTTAAAA  TCTCCTGTC  TTACGTTTA
                L  N  P    R  I  I    T  P  I    T  G  R    G  E  V
        1171  TTAAATCCT  AGAATTATT  ACACCAATT  ACAGGTAGA  GGAGAAGTA
              AATTTAGGA  TCTTAATAA  TGTGGTTAA  TGTCCATCT  CCTCTTCAT
                K  K  L    L  R  F    C  K  N    I  V  S    V  K  G
        1216  AAAAAACTC  CTTAGATTT  TGTAAAAAT  ATTGTTTCT  GTAAAAGGC
              TTTTTTGAG  GAATCTAAA  ACATTTTTA  TAACAAAGA  CATTTTCCG
                I  R  K    L  R
        1261  ATAAGGAAG  CTTCGC
              TATTCCTTC  GAAGCG
```

SEQUENCE LISTING

```
<160> NUMBER OF SEQ ID NOS: 163

<210> SEQ ID NO 1
<211> LENGTH: 7
<212> TYPE: PRT
<213> ORGANISM: Clostridium botulinum serotype A

<400> SEQUENCE: 1

Phe Glu Phe Tyr Lys Leu Leu
1               5

<210> SEQ ID NO 2
<211> LENGTH: 7
<212> TYPE: PRT
<213> ORGANISM: Rattus norvegicus

<400> SEQUENCE: 2

Glu Glu Lys Arg Ala Ile Leu
1               5

<210> SEQ ID NO 3
```

```
<211> LENGTH: 7
<212> TYPE: PRT
<213> ORGANISM: Rattus norvegicus

<400> SEQUENCE: 3

Glu Glu Lys Met Ala Ile Leu
1               5

<210> SEQ ID NO 4
<211> LENGTH: 7
<212> TYPE: PRT
<213> ORGANISM: Rattus norvegicus

<400> SEQUENCE: 4

Ser Glu Arg Asp Val Leu Leu
1               5

<210> SEQ ID NO 5
<211> LENGTH: 7
<212> TYPE: PRT
<213> ORGANISM: Rattus norvegicus

<400> SEQUENCE: 5

Val Asp Thr Gln Val Leu Leu
1               5

<210> SEQ ID NO 6
<211> LENGTH: 7
<212> TYPE: PRT
<213> ORGANISM: Mus musculus

<400> SEQUENCE: 6

Ala Glu Val Gln Ala Leu Leu
1               5

<210> SEQ ID NO 7
<211> LENGTH: 7
<212> TYPE: PRT
<213> ORGANISM: Xenopus laevis

<400> SEQUENCE: 7

Ser Asp Lys Gln Asn Leu Leu
1               5

<210> SEQ ID NO 8
<211> LENGTH: 7
<212> TYPE: PRT
<213> ORGANISM: Gallus gallus

<400> SEQUENCE: 8

Ser Asp Arg Gln Asn Leu Ile
1               5

<210> SEQ ID NO 9
<211> LENGTH: 7
<212> TYPE: PRT
<213> ORGANISM: Ovis aries

<400> SEQUENCE: 9

Ala Asp Thr Gln Val Leu Met
1               5

<210> SEQ ID NO 10
<211> LENGTH: 7
<212> TYPE: PRT
<213> ORGANISM: Homo sapiens
```

```
<400> SEQUENCE: 10

Ser Asp Lys Asn Thr Leu Leu
1               5

<210> SEQ ID NO 11
<211> LENGTH: 7
<212> TYPE: PRT
<213> ORGANISM: Homo sapiens

<400> SEQUENCE: 11

Ser Gln Ile Lys Arg Leu Leu
1               5

<210> SEQ ID NO 12
<211> LENGTH: 7
<212> TYPE: PRT
<213> ORGANISM: Homo sapiens

<400> SEQUENCE: 12

Ala Asp Thr Gln Ala Leu Leu
1               5

<210> SEQ ID NO 13
<211> LENGTH: 7
<212> TYPE: PRT
<213> ORGANISM: Saccharomyces cerevisiae

<400> SEQUENCE: 13

Asn Glu Gln Ser Pro Leu Leu
1               5

<210> SEQ ID NO 14
<211> LENGTH: 30
<212> TYPE: PRT
<213> ORGANISM: Clostridium botulinum serotype A
<220> FEATURE:
<221> NAME/KEY: DOMAIN
<222> LOCATION: (1)...(30)
<223> OTHER INFORMATION: Amino terminal 30 amino acids of light chain

<400> SEQUENCE: 14

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met
            20                  25                  30

<210> SEQ ID NO 15
<211> LENGTH: 50
<212> TYPE: PRT
<213> ORGANISM: Clostridium botulinum serotype A
<220> FEATURE:
<221> NAME/KEY: DOMAIN
<222> LOCATION: (1)...(50)
<223> OTHER INFORMATION: Carboxyl terminal 50 amino acids of light chain

<400> SEQUENCE: 15

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Leu Leu Cys Val Arg Gly Ile Ile Thr
        35                  40                  45

Ser Lys
    50
```

<210> SEQ ID NO 16
<211> LENGTH: 30
<212> TYPE: PRT
<213> ORGANISM: Clostridium botulinum serotype B
<220> FEATURE:
<221> NAME/KEY: DOMAIN
<222> LOCATION: (13)...(30)
<223> OTHER INFORMATION: Amino terminal 30 amino acids of light chain

<400> SEQUENCE: 16

Met Pro Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr
            20                  25                  30

<210> SEQ ID NO 17
<211> LENGTH: 50
<212> TYPE: PRT
<213> ORGANISM: Clostridium botulinum serotype B
<220> FEATURE:
<221> NAME/KEY: DOMAIN
<222> LOCATION: (1)...(50)
<223> OTHER INFORMATION: Carboxyl terminal 50 amino acids of light chain

<400> SEQUENCE: 17

Tyr Thr Ile Glu Glu Gly Phe Asn Ile Ser Asp Lys Asn Met Gly Lys
1               5                   10                  15

Glu Tyr Arg Gly Gln Asn Lys Ala Ile Asn Lys Gln Ala Tyr Glu Glu
            20                  25                  30

Ile Ser Lys Glu His Leu Ala Val Tyr Lys Ile Gln Met Cys Lys Ser
        35                  40                  45

Val Lys
    50

<210> SEQ ID NO 18
<211> LENGTH: 30
<212> TYPE: PRT
<213> ORGANISM: Clostridium botulinum serotype C1
<220> FEATURE:
<221> NAME/KEY: DOMAIN
<222> LOCATION: (1)...(30)
<223> OTHER INFORMATION: Amino terminal 30 amino acids of light chain

<400> SEQUENCE: 18

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala
            20                  25                  30

<210> SEQ ID NO 19
<211> LENGTH: 50
<212> TYPE: PRT
<213> ORGANISM: Clostridium botulinum serotype C1
<220> FEATURE:
<221> NAME/KEY: DOMAIN
<222> LOCATION: (1)...(50)
<223> OTHER INFORMATION: Carboxyl terminal 50 amino acids of light chain

<400> SEQUENCE: 19

Asn Ile Pro Lys Ser Asn Leu Asn Val Leu Phe Met Gly Gln Asn Leu
1               5                   10                  15

Ser Arg Asn Pro Ala Leu Arg Lys Val Asn Pro Glu Asn Met Leu Tyr
            20                  25                  30

Leu Phe Thr Lys Phe Cys His Lys Ala Ile Asp Gly Arg Ser Leu Tyr

```
                35                  40                  45
Asn Lys
    50

<210> SEQ ID NO 20
<211> LENGTH: 30
<212> TYPE: PRT
<213> ORGANISM: Clostridium botulinum serotype D
<220> FEATURE:
<221> NAME/KEY: DOMAIN
<222> LOCATION: (1)...(30)
<223> OTHER INFORMATION: Amino terminal 30 amino acids of light chain

<400> SEQUENCE: 20

Met Thr Trp Pro Val Lys Asp Phe Asn Tyr Ser Asp Pro Val Asn Asp
1               5                  10                  15

Asn Asp Ile Leu Tyr Leu Arg Ile Pro Gln Asn Lys Leu Ile
            20                  25                  30

<210> SEQ ID NO 21
<211> LENGTH: 50
<212> TYPE: PRT
<213> ORGANISM: Clostridium botulinum serotype D
<220> FEATURE:
<221> NAME/KEY: DOMAIN
<222> LOCATION: (1)...(50)
<223> OTHER INFORMATION: Carboxyl terminal 50 amino acids of light chain

<400> SEQUENCE: 21

Tyr Thr Ile Arg Asp Gly Phe Asn Leu Thr Asn Lys Gly Phe Asn Ile
1               5                  10                  15

Glu Asn Ser Gly Gln Asn Ile Glu Arg Asn Pro Ala Leu Gln Lys Leu
            20                  25                  30

Ser Ser Glu Ser Val Val Asp Leu Phe Thr Lys Val Cys Leu Arg Leu
        35                  40                  45

Thr Lys
    50

<210> SEQ ID NO 22
<211> LENGTH: 30
<212> TYPE: PRT
<213> ORGANISM: Clostridium botulinum serotype E
<220> FEATURE:
<221> NAME/KEY: DOMAIN
<222> LOCATION: (1)...(30)
<223> OTHER INFORMATION: Amino terminal 30 amino acid of light chain

<400> SEQUENCE: 22

Met Pro Lys Ile Asn Ser Phe Asn Tyr Asn Asp Pro Val Asn Asp Arg
1               5                  10                  15

Thr Ile Leu Tyr Ile Lys Pro Gly Gly Cys Gln Glu Phe Tyr
            20                  25                  30

<210> SEQ ID NO 23
<211> LENGTH: 50
<212> TYPE: PRT
<213> ORGANISM: Clostridium botulinum serotype E
<220> FEATURE:
<221> NAME/KEY: DOMAIN
<222> LOCATION: (1)...(50)
<223> OTHER INFORMATION: Carboxyl terminal 50 amino acids of light chain

<400> SEQUENCE: 23

Gly Tyr Asn Ile Asn Asn Leu Lys Val Asn Phe Arg Gly Gln Asn Ala
1               5                  10                  15
```

```
Asn Leu Asn Pro Arg Ile Ile Thr Pro Ile Thr Gly Arg Gly Leu Val
            20                  25                  30

Lys Lys Ile Ile Arg Phe Cys Lys Asn Ile Val Ser Val Lys Gly Ile
        35                  40                  45

Arg Lys
    50

<210> SEQ ID NO 24
<211> LENGTH: 30
<212> TYPE: PRT
<213> ORGANISM: Clostridium botulinum serotype F
<220> FEATURE:
<221> NAME/KEY: DOMAIN
<222> LOCATION: (1)...(30)
<223> OTHER INFORMATION: Amino terminal 30 amino acids of light chain

<400> SEQUENCE: 24

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser
            20                  25                  30

<210> SEQ ID NO 25
<211> LENGTH: 50
<212> TYPE: PRT
<213> ORGANISM: Clostridium botulinum serotype F
<220> FEATURE:
<221> NAME/KEY: DOMAIN
<222> LOCATION: (1)...(50)
<223> OTHER INFORMATION: Carboxyl terminal 50 amino acids of light chain

<400> SEQUENCE: 25

Thr Val Ser Glu Gly Phe Asn Ile Gly Asn Leu Ala Val Asn Asn Arg
1               5                   10                  15

Gly Gln Ser Ile Lys Leu Asn Pro Lys Ile Ile Asp Ser Ile Pro Asp
            20                  25                  30

Lys Gly Leu Val Glu Lys Ile Val Lys Phe Cys Lys Ser Val Ile Pro
        35                  40                  45

Arg Lys
    50

<210> SEQ ID NO 26
<211> LENGTH: 30
<212> TYPE: PRT
<213> ORGANISM: Clostridium botulinum serotype G
<220> FEATURE:
<221> NAME/KEY: DOMAIN
<222> LOCATION: (1)...(30)
<223> OTHER INFORMATION: Amino terminal 30 amino acids of light chain

<400> SEQUENCE: 26

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro
            20                  25                  30

<210> SEQ ID NO 27
<211> LENGTH: 50
<212> TYPE: PRT
<213> ORGANISM: Clostridium botulinum serotype G
<220> FEATURE:
<221> NAME/KEY: DOMAIN
<222> LOCATION: (1)...(50)
<223> OTHER INFORMATION: Carboxyl terminal 50 amino acids of light chain

<400> SEQUENCE: 27
```

```
Gln Asn Glu Gly Phe Asn Ile Ala Ser Lys Asn Leu Lys Thr Glu Phe
1               5                   10                  15

Asn Gly Gln Asn Lys Ala Val Asn Lys Glu Ala Tyr Glu Glu Ile Ser
            20                  25                  30

Leu Glu His Leu Val Ile Tyr Arg Ile Ala Met Cys Lys Pro Val Met
        35                  40                  45

Tyr Lys
    50

<210> SEQ ID NO 28
<211> LENGTH: 30
<212> TYPE: PRT
<213> ORGANISM: Clostridium botulinum serotype A
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (4)...(4)
<223> OTHER INFORMATION: Alanine substitution

<400> SEQUENCE: 28

Met Pro Phe Ala Asn Lys Gln Phe Asn Tyr Lys Asp Pro Val Asn Gly
1               5                   10                  15

Val Asp Ile Ala Tyr Ile Lys Ile Pro Asn Ala Gly Gln Met
            20                  25                  30

<210> SEQ ID NO 29
<211> LENGTH: 50
<212> TYPE: PRT
<213> ORGANISM: Clostridium botulinum serotype A
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (25)...(25)
<223> OTHER INFORMATION: Arginine substitution

<400> SEQUENCE: 29

Gly Phe Asn Leu Arg Asn Thr Asn Leu Ala Ala Asn Phe Asn Gly Gln
1               5                   10                  15

Asn Thr Glu Ile Asn Asn Met Asn Arg Thr Lys Leu Lys Asn Phe Thr
            20                  25                  30

Gly Leu Phe Glu Phe Tyr Lys Leu Leu Cys Val Arg Gly Ile Ile Thr
        35                  40                  45

Ser Lys
    50

<210> SEQ ID NO 30
<211> LENGTH: 30
<212> TYPE: PRT
<213> ORGANISM: Clostridium botulinum serotype A
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (10)...(10)
<223> OTHER INFORMATION: Lysine substitution

<400> SEQUENCE: 30

Met Pro Phe Val Asn Lys Gln Phe Asn Lys Lys Asp Pro Val Asn Gly
1               5                   10                  15

Val Asp Ile Ala Tyr Ile Lys Ile Pro Asn Ala Gly Gln Met
```

-continued

```
                20                  25                  30
```

```
<210> SEQ ID NO 31
<211> LENGTH: 50
<212> TYPE: PRT
<213> ORGANISM: Clostridium botulinum serotype A
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (31)...(31)
<223> OTHER INFORMATION: Alanine substitution
<221> NAME/KEY: VARIANT
<222> LOCATION: (32)...(32)
<223> OTHER INFORMATION: Alanine substitution

<400> SEQUENCE: 31

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Ala Ala
            20                  25                  30

Gly Leu Phe Glu Phe Tyr Lys Leu Leu Cys Val Arg Gly Ile Ile Thr
        35                  40                  45

Ser Lys
    50

<210> SEQ ID NO 32
<211> LENGTH: 30
<212> TYPE: PRT
<213> ORGANISM: Clostridium botulinum serotype A
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (21)...(21)
<223> OTHER INFORMATION: Arginine substitution

<400> SEQUENCE: 32

Met Pro Phe Val Asn Lys Gln Phe Asn Tyr Lys Asp Pro Val Asn Gly
1               5                   10                  15

Val Asp Ile Ala Arg Ile Lys Ile Pro Asn Ala Gly Gln Met
            20                  25                  30

<210> SEQ ID NO 33
<211> LENGTH: 50
<212> TYPE: PRT
<213> ORGANISM: Clostridium botulinum serotype A
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (13)...(13)
<223> OTHER INFORMATION: Histidine substitution

<400> SEQUENCE: 33

Gly Phe Asn Leu Arg Asn Thr Asn Leu Ala Ala Asn His Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Leu Leu Cys Val Arg Gly Ile Ile Thr
        35                  40                  45

Ser Lys
    50
```

```
<210> SEQ ID NO 34
<211> LENGTH: 30
<212> TYPE: PRT
<213> ORGANISM: Clostridium botulinum serotype A
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (7)...(7)
<223> OTHER INFORMATION: Histidine substitution

<400> SEQUENCE: 34

Met Pro Phe Val Asn Lys His Phe Asn Tyr Lys Asp Pro Val Asn Gly
1               5                   10                  15

Val Asp Ile Ala Tyr Ile Lys Ile Pro Asn Ala Gly Gln Met
            20                  25                  30

<210> SEQ ID NO 35
<211> LENGTH: 50
<212> TYPE: PRT
<213> ORGANISM: Clostridium botulinum serotype A
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (43)...(43)
<223> OTHER INFORMATION: Alanine substitution

<400> SEQUENCE: 35

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Leu Leu Cys Ala Arg Gly Ile Ile Thr
        35                  40                  45

Ser Lys
    50

<210> SEQ ID NO 36
<211> LENGTH: 30
<212> TYPE: PRT
<213> ORGANISM: Clostridium botulinum serotype B
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (3)...(3)
<223> OTHER INFORMATION: Alanine substitution

<400> SEQUENCE: 36

Met Pro Ala Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr
            20                  25                  30

<210> SEQ ID NO 37
<211> LENGTH: 50
<212> TYPE: PRT
<213> ORGANISM: Clostridium botulinum serotype B
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (44)...(44)
```

<223> OTHER INFORMATION: Arginine substitution

<400> SEQUENCE: 37

Tyr Thr Ile Glu Glu Gly Phe Asn Ile Ser Asp Lys Asn Met Gly Lys
1               5                   10                  15

Glu Tyr Arg Gly Gln Asn Lys Ala Ile Asn Lys Gln Ala Tyr Glu Glu
            20                  25                  30

Ile Ser Lys Glu His Leu Ala Val Tyr Lys Ile Arg Met Cys Lys Ser
        35                  40                  45

Val Lys
    50

<210> SEQ ID NO 38
<211> LENGTH: 30
<212> TYPE: PRT
<213> ORGANISM: Clostridium botulinum serotype B
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (21)...(21)
<223> OTHER INFORMATION: Alanine substitution
<221> NAME/KEY: VARIANT
<222> LOCATION: (22)...(22)
<223> OTHER INFORMATION: Alanine substitution

<400> SEQUENCE: 38

Met Pro Val Thr Ile Asn Asn Phe Asn Tyr Asn Asp Pro Ile Asp Asn
1               5                   10                  15

Asp Asn Ile Ile Ala Ala Glu Pro Pro Phe Ala Arg Gly Thr
            20                  25                  30

<210> SEQ ID NO 39
<211> LENGTH: 50
<212> TYPE: PRT
<213> ORGANISM: Clostridium botulinum serotype B
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (41)...(41)
<223> OTHER INFORMATION: Arginine substitution

<400> SEQUENCE: 39

Tyr Thr Ile Glu Glu Gly Phe Asn Ile Ser Asp Lys Asn Met Gly Lys
1               5                   10                  15

Glu Tyr Arg Gly Gln Asn Lys Ala Ile Asn Lys Gln Ala Tyr Glu Glu
            20                  25                  30

Ile Ser Lys Glu His Leu Ala Val Arg Lys Ile Gln Met Cys Lys Ser
        35                  40                  45

Val Lys
    50

<210> SEQ ID NO 40
<211> LENGTH: 30
<212> TYPE: PRT
<213> ORGANISM: Clostridium botulinum serotype B
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (10)...(10)
<223> OTHER INFORMATION: Arginine substitution

```
<400> SEQUENCE: 40

Met Pro Val Thr Ile Asn Asn Phe Asn Arg Asn Asp Pro Ile Asp Asn
1               5                   10                  15

Asp Asn Ile Ile Met Met Glu Pro Pro Phe Ala Arg Gly Thr
            20                  25                  30

<210> SEQ ID NO 41
<211> LENGTH: 50
<212> TYPE: PRT
<213> ORGANISM: Clostridium botulinum serotype B
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (30)...(30)
<223> OTHER INFORMATION: Lysine substitution

<400> SEQUENCE: 41

Tyr Thr Ile Glu Glu Gly Phe Asn Ile Ser Asp Lys Asn Met Gly Lys
1               5                   10                  15

Glu Tyr Arg Gly Gln Asn Lys Ala Ile Asn Lys Gln Ala Lys Glu Glu
            20                  25                  30

Ile Ser Lys Glu His Leu Ala Val Tyr Lys Ile Gln Met Cys Lys Ser
        35                  40                  45

Val Lys
    50

<210> SEQ ID NO 42
<211> LENGTH: 30
<212> TYPE: PRT
<213> ORGANISM: Clostridium botulinum serotype C1
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (8)...(8)
<223> OTHER INFORMATION: Lysine substitution

<400> SEQUENCE: 42

Met Pro Ile Thr Ile Asn Asn Lys Asn Tyr Ser Asp Pro Val Asp Asn
1               5                   10                  15

Lys Asn Ile Leu Tyr Leu Asp Thr His Leu Asn Thr Leu Ala
            20                  25                  30

<210> SEQ ID NO 43
<211> LENGTH: 50
<212> TYPE: PRT
<213> ORGANISM: Clostridium botulinum serotype C1
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (48)...(48)
<223> OTHER INFORMATION: Arginine substitution

<400> SEQUENCE: 43

Asn Ile Pro Lys Ser Asn Leu Asn Val Leu Phe Met Gly Gln Asn Leu
1               5                   10                  15

Ser Arg Asn Pro Ala Leu Arg Lys Val Asn Pro Glu Asn Met Leu Tyr
            20                  25                  30

Leu Phe Thr Lys Phe Cys His Lys Ala Ile Asp Gly Arg Ser Leu Arg
        35                  40                  45
```

-continued

Asn Lys
    50

<210> SEQ ID NO 44
<211> LENGTH: 30
<212> TYPE: PRT
<213> ORGANISM: Clostridium botulinum serotype D
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (5)...(5)
<223> OTHER INFORMATION: Alanine substitution
<221> NAME/KEY: VARIANT
<222> LOCATION: (14)...(14)
<223> OTHER INFORMATION: Alanine substitution

<400> SEQUENCE: 44

Met Thr Trp Pro Ala Lys Asp Phe Asn Tyr Ser Asp Pro Ala Asn Asp
1               5                   10                  15

Asn Asp Ile Leu Tyr Leu Arg Ile Pro Gln Asn Lys Leu Ile
            20                  25                  30

<210> SEQ ID NO 45
<211> LENGTH: 50
<212> TYPE: PRT
<213> ORGANISM: Clostridium botulinum serotype D
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (44)...(44)
<223> OTHER INFORMATION: Alanine substitution

<400> SEQUENCE: 45

Tyr Thr Ile Arg Asp Gly Phe Asn Leu Thr Asn Lys Gly Phe Asn Ile
1               5                   10                  15

Glu Asn Ser Gly Gln Asn Ile Glu Arg Asn Pro Ala Leu Gln Lys Leu
            20                  25                  30

Ser Ser Glu Ser Val Val Asp Leu Phe Thr Lys Ala Cys Leu Arg Leu
        35                  40                  45

Thr Lys
    50

<210> SEQ ID NO 46
<211> LENGTH: 30
<212> TYPE: PRT
<213> ORGANISM: Clostridium botulinum serotype E
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (13)...(13)
<223> OTHER INFORMATION: Alanine substitution

<400> SEQUENCE: 46

Met Pro Lys Ile Asn Ser Phe Asn Tyr Asn Asp Pro Ala Asn Asp Arg
1               5                   10                  15

Thr Ile Leu Tyr Ile Lys Pro Gly Gly Cys Gln Glu Phe Tyr
            20                  25                  30

<210> SEQ ID NO 47
<211> LENGTH: 50
<212> TYPE: PRT
<213> ORGANISM: Clostridium botulinum serotype E

```
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (31)...(31)
<223> OTHER INFORMATION: Histidine substitution

<400> SEQUENCE: 47

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly His Val
            20                  25                  30

Lys Lys Ile Ile Arg Phe Cys Lys Asn Ile Val Ser Val Lys Gly Ile
        35                  40                  45

Arg Lys
    50

<210> SEQ ID NO 48
<211> LENGTH: 30
<212> TYPE: PRT
<213> ORGANISM: Clostridium botulinum serotype E
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (7)...(7)
<223> OTHER INFORMATION: Arginine substitution

<400> SEQUENCE: 48

Met Pro Lys Ile Asn Ser Arg Asn Tyr Asn Asp Pro Val Asn Asp Arg
1               5                   10                  15

Thr Ile Leu Tyr Ile Lys Pro Gly Gly Cys Gln Glu Phe Tyr
            20                  25                  30

<210> SEQ ID NO 49
<211> LENGTH: 50
<212> TYPE: PRT
<213> ORGANISM: Clostridium botulinum serotype E
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (42)...(42)
<223> OTHER INFORMATION: Alanine substitution
<221> NAME/KEY: VARIANT
<222> LOCATION: (43)...(43)
<223> OTHER INFORMATION: Alanine substitution

<400> SEQUENCE: 49

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

Lys Lys Ile Ile Arg Phe Cys Lys Asn Ala Ala Ser Val Lys Gly Ile
        35                  40                  45

Arg Lys
    50

<210> SEQ ID NO 50
<211> LENGTH: 30
<212> TYPE: PRT
<213> ORGANISM: Clostridium botulinum serotype E
<220> FEATURE:
<221> NAME/KEY: DOMAIN
```

```
<222> LOCATION: (1)...(30)
<223> OTHER INFORMATION: Amino terminal 30 amino acids of light chain
<221> NAME/KEY: VARIANT
<222> LOCATION: (30)...(30)
<223> OTHER INFORMATION: Arginine substitution

<400> SEQUENCE: 50

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Arg
            20                  25                  30

<210> SEQ ID NO 51
<211> LENGTH: 50
<212> TYPE: PRT
<213> ORGANISM: Clostridium botulinum serotype E
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (45)...(45)
<223> OTHER INFORMATION: Alanine substitution

<400> SEQUENCE: 51

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

Lys Lys Ile Ile Arg Phe Cys Lys Asn Ile Val Ser Ala Lys Gly Ile
        35                  40                  45

Arg Lys
    50

<210> SEQ ID NO 52
<211> LENGTH: 30
<212> TYPE: PRT
<213> ORGANISM: Clostridium botulinum serotype F
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (3)...(3)
<223> OTHER INFORMATION: Alanine substitution

<400> SEQUENCE: 52

Met Pro Ala Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser
            20                  25                  30

<210> SEQ ID NO 53
<211> LENGTH: 50
<212> TYPE: PRT
<213> ORGANISM: Clostridium botulinum serotype F
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (46)...(46)
<223> OTHER INFORMATION: Alanine substitution

<400> SEQUENCE: 53

Thr Val Ser Glu Gly Phe Asn Ile Gly Asn Leu Ala Val Asn Asn Arg
1               5                   10                  15
```

```
Gly Gln Ser Ile Lys Leu Asn Pro Lys Ile Ile Asp Ser Ile Pro Asp
                20                  25                  30

Lys Gly Leu Val Glu Lys Ile Val Lys Phe Cys Lys Ser Ala Ile Pro
        35                  40                  45

Arg Lys
    50

<210> SEQ ID NO 54
<211> LENGTH: 30
<212> TYPE: PRT
<213> ORGANISM: Clostridium botulinum serotype G
<220> FEATURE:
<221> NAME/KEY: DOMAIN
<222> LOCATION: (1)...(30)
<223> OTHER INFORMATION: Amino terminal 30 amino acids of light chain
<221> NAME/KEY: VARIANT
<222> LOCATION: (8)...(8)
<223> OTHER INFORMATION: Histidine substitution

<400> SEQUENCE: 54

Met Pro Val Asn Ile Lys Asn His Asn Tyr Asn Asp Pro Ile Asn Asn
1               5                   10                  15

Asp Asp Ile Ile Met Met Glu Pro Phe Asn Asp Pro Gly Pro
                20                  25                  30

<210> SEQ ID NO 55
<211> LENGTH: 50
<212> TYPE: PRT
<213> ORGANISM: Clostridium botulinum serotype G
<220> FEATURE:
<221> NAME/KEY: DOMAIN
<222> LOCATION: (1)...(50)
<223> OTHER INFORMATION: Carboxyl terminal 50 amino acids of light chain
<221> NAME/KEY: VARIANT
<222> LOCATION: (47)...(47)
<223> OTHER INFORMATION: Alanine substitution

<400> SEQUENCE: 55

Gln Asn Glu Gly Phe Asn Ile Ala Ser Lys Asn Leu Lys Thr Glu Phe
1               5                   10                  15

Asn Gly Gln Asn Lys Ala Val Asn Lys Glu Ala Tyr Glu Glu Ile Ser
                20                  25                  30

Leu Glu His Leu Val Ile Tyr Arg Ile Ala Met Cys Lys Pro Ala Met
        35                  40                  45

Tyr Lys
    50

<210> SEQ ID NO 56
<211> LENGTH: 26
<212> TYPE: PRT
<213> ORGANISM: Clostridium botulinum serotype A
<220> FEATURE:
<221> NAME/KEY: VARIANT
<222> LOCATION: (1)...(26)
<223> OTHER INFORMATION: Variant of amino-terminal 30 amino acids of LC

<400> SEQUENCE: 56

Met Pro Phe Val Asn Lys Gln Phe Asn Tyr Lys Asp Pro Val Asn Gly
1               5                   10                  15

Val Asp Ile Ala Tyr Ile Lys Ile Pro His
                20                  25

<210> SEQ ID NO 57
<211> LENGTH: 43
<212> TYPE: PRT
<213> ORGANISM: Clostridium botulinum serotype A
```

```
<220> FEATURE:
<221> NAME/KEY: VARIANT
<222> LOCATION: (1)...(43)
<223> OTHER INFORMATION: Variant of carboxyl-terminal 50 amino acids of
      LC

<400> SEQUENCE: 57

Gly Phe Asn Leu Arg Asn Thr Asn Leu Ala Ala Asn Phe Asn Gly Gln
1               5                   10                  15

Asn Thr Glu Ile Asn Asn Met Asn Ala Ala Ala Ala Ala Ala Ala
            20                  25                  30

Ala Ala Cys Val Arg Gly Ile Ile Thr Ser Lys
        35                  40

<210> SEQ ID NO 58
<211> LENGTH: 26
<212> TYPE: PRT
<213> ORGANISM: Clostridium botulinum serotype A
<220> FEATURE:
<221> NAME/KEY: VARIANT
<222> LOCATION: (1)...(26)
<223> OTHER INFORMATION: Variant of amino-terminal 30 amino acids of LC

<400> SEQUENCE: 58

Met Ala Ala Ala Asn Tyr Lys Asp Pro Val Asn Gly Val Asp Ile Ala
1               5                   10                  15

Tyr Ile Lys Ile Pro Asn Ala Gly Gln Met
            20                  25

<210> SEQ ID NO 59
<211> LENGTH: 48
<212> TYPE: PRT
<213> ORGANISM: Clostridium botulinum serotype A
<220> FEATURE:
<221> NAME/KEY: VARIANT
<222> LOCATION: (1)...(48)
<223> OTHER INFORMATION: Variant of carboxyl-terminal 50 amino acids of
      LC

<400> SEQUENCE: 59

Gly Lys Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys Cys Val Arg Gly Ile Ile Thr Ser Lys
        35                  40                  45

<210> SEQ ID NO 60
<211> LENGTH: 26
<212> TYPE: PRT
<213> ORGANISM: Clostridium botulinum serotype A
<220> FEATURE:
<221> NAME/KEY: VARIANT
<222> LOCATION: (1)...(26)
<223> OTHER INFORMATION: Variant of amino-terminal 30 amino acids of LC

<400> SEQUENCE: 60

Met Pro Phe Val Asn Lys Gln Phe Asn Tyr Lys Asp Pro Val Asn Gly
1               5                   10                  15

Val Asp Ile Ala Arg Asn Ala Gly Gln Met
            20                  25

<210> SEQ ID NO 61
<211> LENGTH: 46
<212> TYPE: PRT
<213> ORGANISM: Clostridium botulinum serotype A
```

-continued

```
<220> FEATURE:
<221> NAME/KEY: VARIANT
<222> LOCATION: (1)...(46)
<223> OTHER INFORMATION: Variant of carboxyl-terminal 50 amino acids of
      LC

<400> SEQUENCE: 61

Gly Phe Asn Leu Arg Asn Thr Asn Leu Ala Ala His Asn Thr Glu Ile
1               5                   10                  15

Asn Asn Met Asn Phe Thr Lys Leu Lys Asn Phe Thr Gly Leu Phe Glu
            20                  25                  30

Phe Tyr Lys Leu Leu Cys Val Arg Gly Ile Ile Thr Ser Lys
        35                  40                  45

<210> SEQ ID NO 62
<211> LENGTH: 26
<212> TYPE: PRT
<213> ORGANISM: Clostridium botulinum serotype A
<220> FEATURE:
<221> NAME/KEY: VARIANT
<222> LOCATION: (1)...(26)
<223> OTHER INFORMATION: Variant of amino-terminal 30 amino acids of LC

<400> SEQUENCE: 62

Met Pro Lys Val Asn Lys Gln Phe Asn Val Asn Gly Val Asp Ile Ala
1               5                   10                  15

Tyr Ile Lys Ile Pro Asn Ala Gly Gln Met
            20                  25

<210> SEQ ID NO 63
<211> LENGTH: 42
<212> TYPE: PRT
<213> ORGANISM: Clostridium botulinum serotype A
<220> FEATURE:
<221> NAME/KEY: VARIANT
<222> LOCATION: (1)...(42)
<223> OTHER INFORMATION: Variant of carboxyl-terminal 50 amino acids of
      LC

<400> SEQUENCE: 63

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Arg Arg Thr Ser Lys
        35                  40

<210> SEQ ID NO 64
<211> LENGTH: 30
<212> TYPE: PRT
<213> ORGANISM: Clostridium botulinum serotype B
<220> FEATURE:
<221> NAME/KEY: VARIANT
<222> LOCATION: (1)...(30)
<223> OTHER INFORMATION: Variant of amino-terminal 30 amino acids of LC

<400> SEQUENCE: 64

Met Pro Val Thr Ile Asn Asn Phe Asn Tyr Asn Asp Pro Ile Asp Asn
1               5                   10                  15

Asp Asn Ile Ile Ala Ala Ala Ala Ala Ala Ala Arg Gly Thr
            20                  25                  30

<210> SEQ ID NO 65
<211> LENGTH: 37
<212> TYPE: PRT
<213> ORGANISM: Clostridium botulinum serotype B
```

-continued

```
<220> FEATURE:
<221> NAME/KEY: VARIANT
<222> LOCATION: (1)...(37)
<223> OTHER INFORMATION: Variant of carboxyl-terminal 50 amino acids of
      LC

<400> SEQUENCE: 65

Tyr Thr Ile Pro Pro Gly Phe Asn Ile Ser Asp Lys Asn Met Gly Lys
1               5                   10                  15

Glu Tyr Arg Gly Gln Asn Lys Ala Ile Asn Lys Gln Ala Tyr Glu Glu
            20                  25                  30

Ile Ser Lys Glu His
        35

<210> SEQ ID NO 66
<211> LENGTH: 26
<212> TYPE: PRT
<213> ORGANISM: Clostridium botulinum serotype B
<220> FEATURE:
<221> NAME/KEY: VARIANT
<222> LOCATION: (1)...(26)
<223> OTHER INFORMATION: Variant of amino-terminal 30 amino acids of LC

<400> SEQUENCE: 66

Met Pro Ala Phe Asn Tyr Asn Asp Pro Ile Asp Asn Asp Asn Ile Ile
1               5                   10                  15

Met Met Glu Pro Pro Phe Ala Arg Gly Thr
            20                  25

<210> SEQ ID NO 67
<211> LENGTH: 50
<212> TYPE: PRT
<213> ORGANISM: Clostridium botulinum serotype B
<220> FEATURE:
<221> NAME/KEY: VARIANT
<222> LOCATION: (1)...(50)
<223> OTHER INFORMATION: Variant of carboxyl-terminal 50 amino acids of
      LC

<400> SEQUENCE: 67

Tyr Thr Ile Glu Glu Gly Phe Asn Ile Ser Asp Lys Asn Met Gly Lys
1               5                   10                  15

Glu Tyr Arg Gly Gln Asn Lys Ala Ala Ala Ala Ala Ala Ala Glu Glu
            20                  25                  30

Ile Ser Lys Glu His Leu Ala Val Tyr Lys Ile Gln Met Cys Lys Ser
        35                  40                  45

Val Lys
    50

<210> SEQ ID NO 68
<211> LENGTH: 20
<212> TYPE: PRT
<213> ORGANISM: Clostridium botulinum serotype B
<220> FEATURE:
<221> NAME/KEY: VARIANT
<222> LOCATION: (1)...(20)
<223> OTHER INFORMATION: Variant of amino-terminal 30 amino acids of LC

<400> SEQUENCE: 68

Met Pro Val Thr Ile Asn Asn Phe Asn Arg Met Met Glu Pro Pro Phe
1               5                   10                  15

Ala Arg Gly Thr
            20

<210> SEQ ID NO 69
```

```
<211> LENGTH: 44
<212> TYPE: PRT
<213> ORGANISM: Clostridium botulinum serotype B
<220> FEATURE:
<221> NAME/KEY: VARIANT
<222> LOCATION: (1)...(44)
<223> OTHER INFORMATION: Variant of carboxyl-terminal 50 amino acids of
      LC

<400> SEQUENCE: 69

Tyr Thr Ile Glu Glu Gly Phe Asn Ile Ser Asp Lys Asn Met Gly Lys
1               5                   10                  15

Glu Tyr Arg Gly Gln Asn Lys Ala Ile Asn Lys Gln Ala Tyr Ala Ala
            20                  25                  30

Ala Ala Ala Ala Ile Gln Met Cys Lys Ser Val Lys
        35                  40

<210> SEQ ID NO 70
<211> LENGTH: 21
<212> TYPE: PRT
<213> ORGANISM: Clostridium botulinum serotype C1
<220> FEATURE:
<221> NAME/KEY: VARIANT
<222> LOCATION: (1)...(21)
<223> OTHER INFORMATION: Variant of amino-terminal 30 amino acids of LC

<400> SEQUENCE: 70

Met Ser Asp Pro Val Asp Asn Lys Asn Ile Leu Tyr Leu Asp Thr His
1               5                   10                  15

Leu Asn Thr Leu Ala
            20

<210> SEQ ID NO 71
<211> LENGTH: 47
<212> TYPE: PRT
<213> ORGANISM: Clostridium botulinum serotype C1
<220> FEATURE:
<221> NAME/KEY: VARIANT
<222> LOCATION: (1)...(47)
<223> OTHER INFORMATION: Variant of carboxyl-terminal 50 amino acids of
      LC

<400> SEQUENCE: 71

Asn Ile Pro Lys Ser Asn Leu Asn Val Leu Phe Met Gly Gln Asn Leu
1               5                   10                  15

Ser Arg Asn Pro Ala Leu Arg Lys Val Asn Pro Glu Asn Met Leu Ala
            20                  25                  30

Ala Ala Cys His Lys Ala Ile Asp Gly Arg Ser Leu Tyr Asn Lys
        35                  40                  45

<210> SEQ ID NO 72
<211> LENGTH: 26
<212> TYPE: PRT
<213> ORGANISM: Clostridium botulinum serotype D
<220> FEATURE:
<221> NAME/KEY: VARIANT
<222> LOCATION: (1)...(26)
<223> OTHER INFORMATION: Variant of amino-terminal 30 amino acids of LC

<400> SEQUENCE: 72

Met Thr Arg Pro Val Lys Asp Asp Pro Val Asn Asp Asn Asp Ile Leu
1               5                   10                  15

Tyr Leu Arg Ile Pro Gln Asn Lys Leu Ile
            20                  25

<210> SEQ ID NO 73
```

```
<211> LENGTH: 44
<212> TYPE: PRT
<213> ORGANISM: Clostridium botulinum serotype D
<220> FEATURE:
<221> NAME/KEY: VARIANT
<222> LOCATION: (1)...(44)
<223> OTHER INFORMATION: Variant of carboxyl-terminal 50 amino acids of
      LC

<400> SEQUENCE: 73

Tyr Thr Ile Arg Asp Gly Phe Asn Leu Thr Asn Lys Gly Phe Asn Ile
1               5                   10                  15

Glu Asn Ser Gly Gln Asn Ile Glu Arg Asn Pro Ala Leu Gln Lys Leu
            20                  25                  30

Asp Leu Pro Pro Lys Val Cys Leu Arg Leu Thr Lys
        35                  40

<210> SEQ ID NO 74
<211> LENGTH: 31
<212> TYPE: PRT
<213> ORGANISM: Clostridium botulinum serotype E
<220> FEATURE:
<221> NAME/KEY: VARIANT
<222> LOCATION: (1)...(31)
<223> OTHER INFORMATION: Variant of amino-terminal 30 amino acids of LC

<400> SEQUENCE: 74

Met Pro Lys Ile Asn Ser Pro Pro Asn Tyr Asn Asp Pro Val Asn Asp
1               5                   10                  15

Arg Thr Ile Leu Tyr Ile Lys Pro Gly Gly Cys Gln Glu Phe Tyr
            20                  25                  30

<210> SEQ ID NO 75
<211> LENGTH: 50
<212> TYPE: PRT
<213> ORGANISM: Clostridium botulinum serotype E
<220> FEATURE:
<221> NAME/KEY: VARIANT
<222> LOCATION: (1)...(50)
<223> OTHER INFORMATION: Variant of carboxyl-terminal 50 amino acids of
      LC

<400> SEQUENCE: 75

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

Lys Lys Ala Ala Ala Ala Cys Lys Asn Ile Val Ser Val Lys Gly Ile
        35                  40                  45

Arg Lys
    50

<210> SEQ ID NO 76
<211> LENGTH: 33
<212> TYPE: PRT
<213> ORGANISM: Clostridium botulinum serotype E
<220> FEATURE:
<221> NAME/KEY: VARIANT
<222> LOCATION: (1)...(33)
<223> OTHER INFORMATION: Variant of amino-terminal 30 amino acids of LC

<400> SEQUENCE: 76

Met Pro Lys Ile Asn Ser Phe Asn Tyr Asn Asp Pro Ala Ala Ala Ala
1               5                   10                  15

Asn Asp Arg Thr Ile Leu Tyr Ile Lys Pro Gly Gly Cys Gln Glu Phe
            20                  25                  30
```

Tyr

<210> SEQ ID NO 77
<211> LENGTH: 47
<212> TYPE: PRT
<213> ORGANISM: Clostridium botulinum serotype E
<220> FEATURE:
<221> NAME/KEY: VARIANT
<222> LOCATION: (1)...(47)
<223> OTHER INFORMATION: Variant of carboxyl-terminal 50 amino acids of
      LC

<400> SEQUENCE: 77

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

His Arg Phe Cys Lys Asn Ile Val Ser Val Lys Gly Ile Arg Lys
        35                  40                  45

<210> SEQ ID NO 78
<211> LENGTH: 30
<212> TYPE: PRT
<213> ORGANISM: Clostridium botulinum serotype E
<220> FEATURE:
<221> NAME/KEY: VARIANT
<222> LOCATION: (1)...(30)
<223> OTHER INFORMATION: Variant of amino-terminal 30 amino acids of LC

<400> SEQUENCE: 78

Met Pro Lys Ile Asn Ser Phe Asn Tyr Asn Asp Pro Val Asn Asp Arg
1               5                   10                  15

Thr Ile Leu Lys Ile Lys Pro Gly Gly Cys Lys Glu Phe Tyr
            20                  25                  30

<210> SEQ ID NO 79
<211> LENGTH: 33
<212> TYPE: PRT
<213> ORGANISM: Clostridium botulinum serotype E
<220> FEATURE:
<221> NAME/KEY: VARIANT
<222> LOCATION: (1)...(33)
<223> OTHER INFORMATION: Variant of carboxyl-terminal 50 amino acids of
      LC

<400> SEQUENCE: 79

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Pro
            20                  25                  30

Pro

<210> SEQ ID NO 80
<211> LENGTH: 24
<212> TYPE: PRT
<213> ORGANISM: Clostridium botulinum serotype F
<220> FEATURE:
<221> NAME/KEY: VARIANT
<222> LOCATION: (1)...(24)
<223> OTHER INFORMATION: Variant of amino-terminal 30 amino acids of LC

<400> SEQUENCE: 80

Met Pro Asn Tyr Asn Asp Pro Val Asn Asp Asp Thr Ile Leu Tyr Met
1               5                   10                  15

Gln Ile Pro Tyr Glu Glu Lys Ser

<210> SEQ ID NO 81
<211> LENGTH: 48
<212> TYPE: PRT
<213> ORGANISM: Clostridium botulinum serotype F
<220> FEATURE:
<221> NAME/KEY: VARIANT
<222> LOCATION: (1)...(48)
<223> OTHER INFORMATION: Variant of carboxyl-terminal 50 amino acids of LC

<400> SEQUENCE: 81

Thr Val Ser Glu Gly Phe Asn Ile Gly Asn Leu Ala Val Asn Asn Arg
1               5                   10                  15

Gly Gln Ser Ile Lys Leu Asn Pro Lys Ile Ile Asp Ser Ile Pro Asp
            20                  25                  30

Lys Gly Ala Ala Ala Ala Ala Ala Cys Lys Ser Val Ile Pro Arg Lys
        35                  40                  45

<210> SEQ ID NO 82
<211> LENGTH: 26
<212> TYPE: PRT
<213> ORGANISM: Clostridium botulinum serotype G
<220> FEATURE:
<221> NAME/KEY: VARIANT
<222> LOCATION: (1)...(26)
<223> OTHER INFORMATION: Variant of amino-terminal 30 amino acids of LC

<400> SEQUENCE: 82

Met Pro Val Asn Ile Pro Pro Asp Pro Ile Asn Asp Asp Ile Ile
1               5                   10                  15

Met Met Glu Pro Phe Asn Asp Pro Gly Pro
            20                  25

<210> SEQ ID NO 83
<211> LENGTH: 35
<212> TYPE: PRT
<213> ORGANISM: Clostridium botulinum serotype G
<220> FEATURE:
<221> NAME/KEY: VARIANT
<222> LOCATION: (1)...(35)
<223> OTHER INFORMATION: Variant of carboxyl-terminal 50 amino acids of LC

<400> SEQUENCE: 83

Gln Asn Glu Gly Phe Asn Ile Ala Ser Lys Asn Leu Lys Thr Glu Phe
1               5                   10                  15

Asn Gly Gln Asn Lys Ala Val Asn Lys Glu Ala Tyr Ala Ala Ala Ala
            20                  25                  30

Ala Ala Ala
        35

<210> SEQ ID NO 84
<211> LENGTH: 22
<212> TYPE: PRT
<213> ORGANISM: Clostridium botulinum serotype A
<220> FEATURE:
<221> NAME/KEY: VARIANT
<222> LOCATION: (1)...(22)
<223> OTHER INFORMATION: Variant of amino-terminal 30 amino acids of LC

<400> SEQUENCE: 84

Met Tyr Lys Asp Pro Val Asn Gly Val Asp Ile Ala Tyr Ile Lys Ile
1               5                   10                  15

Pro Asn Ala Gly Gln Met

```
<210> SEQ ID NO 85
<211> LENGTH: 39
<212> TYPE: PRT
<213> ORGANISM: Clostridium botulinum serotype A
<220> FEATURE:
<221> NAME/KEY: VARIANT
<222> LOCATION: (1)...(39)
<223> OTHER INFORMATION: Variant of carboxyl-terminal 50 amino acids of
      LC

<400> SEQUENCE: 85

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Asn Phe Thr
            20                  25                  30

Gly Leu Phe Glu Phe Tyr Lys
        35

<210> SEQ ID NO 86
<211> LENGTH: 24
<212> TYPE: PRT
<213> ORGANISM: Clostridium botulinum serotype A
<220> FEATURE:
<221> NAME/KEY: VARIANT
<222> LOCATION: (1)...(24)
<223> OTHER INFORMATION: Variant of amino-terminal 30 amino acids of LC

<400> SEQUENCE: 86

Met Pro Phe Val Asn Lys Gln Val Asn Gly Val Asp Ile Ala Tyr Ile
1               5                   10                  15

Lys Ile Pro Asn Ala Gly Gln Met
            20

<210> SEQ ID NO 87
<211> LENGTH: 40
<212> TYPE: PRT
<213> ORGANISM: Clostridium botulinum serotype A
<220> FEATURE:
<221> NAME/KEY: VARIANT
<222> LOCATION: (1)...(40)
<223> OTHER INFORMATION: Variant of carboxyl-terminal 50 amino acids of
      LC

<400> SEQUENCE: 87

Gly Phe Asn Leu Arg Asn Thr Asn Leu Ala Ala Asn Phe Asn Gly Gln
1               5                   10                  15

Asn Thr Glu Ile Asn Asn Met Asn Phe Thr Lys Leu Lys Leu Leu Cys
            20                  25                  30

Val Arg Gly Ile Ile Thr Ser Lys
        35                  40

<210> SEQ ID NO 88
<211> LENGTH: 24
<212> TYPE: PRT
<213> ORGANISM: Clostridium botulinum serotype A
<220> FEATURE:
<221> NAME/KEY: VARIANT
<222> LOCATION: (1)...(24)
<223> OTHER INFORMATION: Variant of amino-terminal 30 amino acids of LC

<400> SEQUENCE: 88

Met Pro Phe Val Asn Lys Gln Phe Asn Tyr Lys Asp Pro Ala Tyr Ile
1               5                   10                  15

Lys Ile Pro Asn Ala Gly Gln Met
```

```
<210> SEQ ID NO 89
<211> LENGTH: 42
<212> TYPE: PRT
<213> ORGANISM: Clostridium botulinum serotype A
<220> FEATURE:
<221> NAME/KEY: VARIANT
<222> LOCATION: (1)...(42)
<223> OTHER INFORMATION: Variant of carboxyl-terminal 50 amino acids of
      LC

<400> SEQUENCE: 89

Gly Phe Asn Leu Arg Asn Thr Asn Leu Ala Ala Asn Phe Asn Gly Gln
1               5                   10                  15

Asn Thr Glu Ile Asn Asn Met Asn Gly Leu Phe Glu Phe Tyr Lys Leu
            20                  25                  30

Leu Cys Val Arg Gly Ile Ile Thr Ser Lys
        35                  40

<210> SEQ ID NO 90
<211> LENGTH: 20
<212> TYPE: PRT
<213> ORGANISM: Clostridium botulinum serotype A
<220> FEATURE:
<221> NAME/KEY: VARIANT
<222> LOCATION: (1)...(20)
<223> OTHER INFORMATION: Variant of amino-terminal 30 amino acids of LC

<400> SEQUENCE: 90

Met Pro Phe Val Asn Lys Gln Phe Asn Tyr Lys Asp Pro Val Asn Gly
1               5                   10                  15

Val Asp Ile Ala
            20

<210> SEQ ID NO 91
<211> LENGTH: 40
<212> TYPE: PRT
<213> ORGANISM: Clostridium botulinum serotype A
<220> FEATURE:
<221> NAME/KEY: VARIANT
<222> LOCATION: (1)...(40)
<223> OTHER INFORMATION: Variant of carboxyl-terminal 50 amino acids of
      LC

<400> SEQUENCE: 91

Gly Phe Asn Leu Arg Asn Asn Thr Glu Ile Asn Asn Met Asn Phe Thr
1               5                   10                  15

Lys Leu Lys Asn Phe Thr Gly Leu Phe Glu Phe Tyr Lys Leu Leu Cys
            20                  25                  30

Val Arg Gly Ile Ile Thr Ser Lys
        35                  40

<210> SEQ ID NO 92
<211> LENGTH: 23
<212> TYPE: PRT
<213> ORGANISM: Clostridium botulinum serotype B
<220> FEATURE:
<221> NAME/KEY: VARIANT
<222> LOCATION: (1)...(23)
<223> OTHER INFORMATION: Variant of amino-terminal 30 amino acids of LC

<400> SEQUENCE: 92

Met Pro Val Thr Ile Asn Asn Phe Asn Tyr Asn Asp Pro Ile Asp Asn
1               5                   10                  15

Asp Asn Ile Ile Met Met Glu
```

```
<210> SEQ ID NO 93
<211> LENGTH: 45
<212> TYPE: PRT
<213> ORGANISM: Clostridium botulinum serotype B
<220> FEATURE:
<221> NAME/KEY: VARIANT
<222> LOCATION: (1)...(45)
<223> OTHER INFORMATION: Variant of carboxyl-terminal 50 amino acids of
      LC

<400> SEQUENCE: 93

Tyr Thr Ile Ile Ser Asp Lys Asn Met Gly Lys Glu Tyr Arg Gly Gln
1               5                   10                  15

Asn Lys Ala Ile Asn Lys Gln Ala Tyr Glu Glu Ile Ser Lys Glu His
            20                  25                  30

Leu Ala Val Tyr Lys Ile Gln Met Cys Lys Ser Val Lys
        35                  40                  45

<210> SEQ ID NO 94
<211> LENGTH: 20
<212> TYPE: PRT
<213> ORGANISM: Clostridium botulinum serotype B
<220> FEATURE:
<221> NAME/KEY: VARIANT
<222> LOCATION: (1)...(20)
<223> OTHER INFORMATION: Variant of amino-terminal 30 amino acids of LC

<400> SEQUENCE: 94

Met Pro Val Thr Ile Asn Asn Phe Asn Tyr Asn Asp Glu Pro Pro Phe
1               5                   10                  15

Ala Arg Gly Thr
            20

<210> SEQ ID NO 95
<211> LENGTH: 42
<212> TYPE: PRT
<213> ORGANISM: Clostridium botulinum serotype B
<220> FEATURE:
<221> NAME/KEY: VARIANT
<222> LOCATION: (1)...(42)
<223> OTHER INFORMATION: Variant of carboxyl-terminal 50 amino acids of
      LC

<400> SEQUENCE: 95

Tyr Thr Ile Glu Glu Gly Phe Asn Ile Ser Asp Gly Gln Asn Lys Ala
1               5                   10                  15

Ile Asn Lys Gln Ala Tyr Glu Glu Ile Ser Lys Glu His Leu Ala Val
            20                  25                  30

Tyr Lys Ile Gln Met Cys Lys Ser Val Lys
        35                  40

<210> SEQ ID NO 96
<211> LENGTH: 22
<212> TYPE: PRT
<213> ORGANISM: Clostridium botulinum serotype B
<220> FEATURE:
<221> NAME/KEY: VARIANT
<222> LOCATION: (1)...(22)
<223> OTHER INFORMATION: Variant of amino-terminal 30 amino acids of LC

<400> SEQUENCE: 96

Met Pro Asn Asp Pro Ile Asp Asn Asp Asn Ile Ile Met Met Glu Pro
1               5                   10                  15

Pro Phe Ala Arg Gly Thr
```

-continued

```
<210> SEQ ID NO 97
<211> LENGTH: 38
<212> TYPE: PRT
<213> ORGANISM: Clostridium botulinum serotype B
<220> FEATURE:
<221> NAME/KEY: VARIANT
<222> LOCATION: (1)...(38)
<223> OTHER INFORMATION: Variant of carboxyl-terminal 50 amino acids of
      LC

<400> SEQUENCE: 97

Tyr Thr Ile Glu Glu Gly Phe Asn Ile Ser Asp Lys Asn Met Gly Lys
1               5                   10                  15

Glu Tyr Arg Gly Gln Asn Lys Ala Ile Asn Lys Gln Ala Lys Ile Gln
            20                  25                  30

Met Cys Lys Ser Val Lys
        35

<210> SEQ ID NO 98
<211> LENGTH: 23
<212> TYPE: PRT
<213> ORGANISM: Clostridium botulinum serotype C1
<220> FEATURE:
<221> NAME/KEY: VARIANT
<222> LOCATION: (1)...(23)
<223> OTHER INFORMATION: Variant of amino-terminal 30 amino acids of LC

<400> SEQUENCE: 98

Met Pro Ile Ser Asp Pro Val Asp Asn Lys Asn Ile Leu Tyr Leu Asp
1               5                   10                  15

Thr His Leu Asn Thr Leu Ala
            20

<210> SEQ ID NO 99
<211> LENGTH: 40
<212> TYPE: PRT
<213> ORGANISM: Clostridium botulinum serotype C1
<220> FEATURE:
<221> NAME/KEY: VARIANT
<222> LOCATION: (1)...(40)
<223> OTHER INFORMATION: Variant of carboxyl-terminal 50 amino acids of
      LC

<400> SEQUENCE: 99

Asn Ile Pro Lys Ser Asn Leu Asn Val Leu Phe Met Gly Gln Asn Leu
1               5                   10                  15

Ser Arg Asn Pro Ala Leu Arg Lys Val Lys Phe Cys His Lys Ala Ile
            20                  25                  30

Asp Gly Arg Ser Leu Tyr Asn Lys
        35                  40

<210> SEQ ID NO 100
<211> LENGTH: 20
<212> TYPE: PRT
<213> ORGANISM: Clostridium botulinum serotype D
<220> FEATURE:
<221> NAME/KEY: VARIANT
<222> LOCATION: (1)...(20)
<223> OTHER INFORMATION:
      Variant of amino-terminal 30 amino acids of LC

<400> SEQUENCE: 100

Met Thr Trp Val Asn Asp Asn Asp Ile Leu Tyr Leu Arg Ile Pro Gln
1               5                   10                  15
```

Asn Lys Leu Ile
        20

<210> SEQ ID NO 101
<211> LENGTH: 40
<212> TYPE: PRT
<213> ORGANISM: Clostridium botulinum serotype D
<220> FEATURE:
<221> NAME/KEY: VARIANT
<222> LOCATION: (1)...(40)
<223> OTHER INFORMATION: Variant of carboxyl-terminal 50 amino acids of
      LC

<400> SEQUENCE: 101

Tyr Thr Ile Arg Asp Gly Phe Asn Leu Thr Asn Lys Gly Phe Asn Ile
1               5                   10                  15

Glu Asn Ser Gly Gln Asn Ile Glu Arg Asn Pro Ala Asp Leu Phe Thr
            20                  25                  30

Lys Val Cys Leu Arg Leu Thr Lys
        35                  40

<210> SEQ ID NO 102
<211> LENGTH: 22
<212> TYPE: PRT
<213> ORGANISM: Clostridium botulinum serotype E
<220> FEATURE:
<221> NAME/KEY: VARIANT
<222> LOCATION: (1)...(22)
<223> OTHER INFORMATION: Variant of amino-terminal 30 amino acids of LC

<400> SEQUENCE: 102

Met Pro Asp Pro Val Asn Asp Arg Thr Ile Leu Tyr Ile Lys Pro Gly
1               5                   10                  15

Gly Cys Gln Glu Phe Tyr
            20

<210> SEQ ID NO 103
<211> LENGTH: 40
<212> TYPE: PRT
<213> ORGANISM: Clostridium botulinum serotype E
<220> FEATURE:
<221> NAME/KEY: VARIANT
<222> LOCATION: (1)...(40)
<223> OTHER INFORMATION:
      Variant of carboxyl-terminal 50 amino acids of LC

<400> SEQUENCE: 103

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Arg Phe Cys Lys Asn Ile
            20                  25                  30

Val Ser Val Lys Gly Ile Arg Lys
        35                  40

<210> SEQ ID NO 104
<211> LENGTH: 20
<212> TYPE: PRT
<213> ORGANISM: Clostridium botulinum serotype E
<220> FEATURE:
<221> NAME/KEY: VARIANT
<222> LOCATION: (1)...(20)
<223> OTHER INFORMATION: Variant of amino-terminal 30 amino acids of LC

<400> SEQUENCE: 104

Met Pro Lys Ile Asn Ser Phe Asn Tyr Asn Ile Lys Pro Gly Gly Cys
1               5                   10                  15

-continued

```
Gln Glu Phe Tyr
            20

<210> SEQ ID NO 105
<211> LENGTH: 44
<212> TYPE: PRT
<213> ORGANISM: Clostridium botulinum serotype E
<220> FEATURE:
<221> NAME/KEY: VARIANT
<222> LOCATION: (1)...(44)
<223> OTHER INFORMATION: Variant of carboxyl-terminal 50 amino acids of
      LC

<400> SEQUENCE: 105

Gly Tyr Asn Ile Asn Asn Gly Gln Asn Ala Asn Leu Asn Pro Arg Ile
1               5                   10                  15

Ile Thr Pro Ile Thr Gly Arg Gly Leu Val Lys Lys Ile Ile Arg Phe
            20                  25                  30

Cys Lys Asn Ile Val Ser Val Lys Gly Ile Arg Lys
        35                  40

<210> SEQ ID NO 106
<211> LENGTH: 22
<212> TYPE: PRT
<213> ORGANISM: Clostridium botulinum serotype E
<220> FEATURE:
<221> NAME/KEY: VARIANT
<222> LOCATION: (1)...(22)
<223> OTHER INFORMATION: Variant of amino-terminal 30 amino acids of LC

<400> SEQUENCE: 106

Met Pro Lys Ile Asn Ser Phe Asn Tyr Asn Asp Pro Val Asn Asp Arg
1               5                   10                  15

Thr Ile Leu Tyr Ile Lys
            20

<210> SEQ ID NO 107
<211> LENGTH: 42
<212> TYPE: PRT
<213> ORGANISM: Clostridium botulinum serotype E
<220> FEATURE:
<221> NAME/KEY: VARIANT
<222> LOCATION: (1)...(42)
<223> OTHER INFORMATION: Variant of carboxyl-terminal 50 amino acids of
      LC

<400> SEQUENCE: 107

Gly Tyr Asn Ile Asn Asn Leu Lys Val Asn Phe Arg Gly Gln Asn Ala
1               5                   10                  15

Asn Leu Asn Pro Arg Ile Ile Thr Pro Ile Thr Gly Arg Gly Leu Val
            20                  25                  30

Lys Lys Ile Ile Arg Lys Gly Ile Arg Lys
        35                  40

<210> SEQ ID NO 108
<211> LENGTH: 25
<212> TYPE: PRT
<213> ORGANISM: Clostridium botulinum serotype F
<220> FEATURE:
<221> NAME/KEY: VARIANT
<222> LOCATION: (1)...(25)
<223> OTHER INFORMATION: Variant of amino-terminal 30 amino acids of LC

<400> SEQUENCE: 108

Met Pro Val Ala Ile Asn Ser Phe Asn Tyr Asn Asp Pro Val Asn Asp
1               5                   10                  15
```

```
Asp Thr Ile Leu Tyr Met Gln Ile Pro
            20                  25

<210> SEQ ID NO 109
<211> LENGTH: 42
<212> TYPE: PRT
<213> ORGANISM: Clostridium botulinum serotype F
<220> FEATURE:
<221> NAME/KEY: VARIANT
<222> LOCATION: (1)...(42)
<223> OTHER INFORMATION: Variant of carboxyl-terminal 50 amino acids of
      LC

<400> SEQUENCE: 109

Thr Val Ser Glu Gly Phe Asn Ile Gly Asn Leu Ala Val Asn Asn Arg
1               5                   10                  15

Gly Gln Ser Ile Lys Leu Asn Pro Lys Ile Ile Asp Ser Ile Pro Asp
            20                  25                  30

Lys Phe Cys Lys Ser Val Ile Pro Arg Lys
        35                  40

<210> SEQ ID NO 110
<211> LENGTH: 38
<212> TYPE: PRT
<213> ORGANISM: Clostridium botulinum serotype G
<220> FEATURE:
<221> NAME/KEY: VARIANT
<222> LOCATION: (1)...(38)
<223> OTHER INFORMATION: Variant of carboxyl-terminal 50 amino acids of
      LC

<400> SEQUENCE: 110

Gln Asn Glu Gly Phe Asn Ile Ala Ser Lys Asn Leu Lys Thr Glu Phe
1               5                   10                  15

Asn Gly Gln Asn Lys Ala Val Asn Lys Glu Ala Arg Ile Ala Met Cys
            20                  25                  30

Lys Pro Val Met Tyr Lys
        35

<210> SEQ ID NO 111
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 111

Xaa Asp Xaa Xaa Xaa Leu Leu
1               5

<210> SEQ ID NO 112
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
```

```
<221> NAME/KEY: VARIANT
<222> LOCATION: (3)...(5)
<223> OTHER INFORMATION: Xaa is any amino acid.

<400> SEQUENCE: 112

Xaa Glu Xaa Xaa Xaa Leu Leu
1               5

<210> SEQ ID NO 113
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 113

Xaa Asp Xaa Xaa Xaa Leu Ile
1               5

<210> SEQ ID NO 114
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 114

Xaa Asp Xaa Xaa Xaa Leu Met
1               5

<210> SEQ ID NO 115
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 115

Xaa Glu Xaa Xaa Xaa Leu Ile
1               5

<210> SEQ ID NO 116
<211> LENGTH: 7
<212> TYPE: PRT
<213> ORGANISM: Artificial Sequence
<220> FEATURE:
<221> NAME/KEY: SITE
<222> LOCATION: (1)...(7)
```

```
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 116

Xaa Glu Xaa Xaa Xaa Ile Leu
1               5

<210> SEQ ID NO 117
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (1)...(1)
<223> OTHER INFORMATION: Xaa is any amino acid.
<221> NAME/KEY: VARIANT
<222> LOCATION: (3)...(5)
<223> OTHER INFORMATION: Xaa is any amino acid.

<400> SEQUENCE: 117

Xaa Glu Xaa Xaa Xaa Leu Met
1               5

<210> SEQ ID NO 118
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Leucine-based motif from BoNT/A light chain.

<400> SEQUENCE: 118

Phe Glu Phe Tyr Lys Leu Leu
1               5

<210> SEQ ID NO 119
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Consensus sequence for Tyrosine-based motif.
<221> NAME/KEY: VARIANT
<222> LOCATION: (2)...(3)
<223> OTHER INFORMATION: Xaa is any amino acid.
<221> NAME/KEY: VARIANT
<222> LOCATION: (4)...(4)
<223> OTHER INFORMATION: Xaa is any hydrophobic amino acid.

<400> SEQUENCE: 119

Tyr Xaa Xaa Xaa
1

<210> SEQ ID NO 120
<211> LENGTH: 8
<212> TYPE: PRT
<213> ORGANISM: Artificial Sequence
<220> FEATURE:
<221> NAME/KEY: SITE
<222> LOCATION: (1)...(8)
<223> OTHER INFORMATION: N-terminal 8 amino acid sequence deletion from
      BoNT/A light chain
```

<400> SEQUENCE: 120

Pro Phe Val Asn Lys Gln Phe Asn
1               5

<210> SEQ ID NO 121
<211> LENGTH: 22
<212> TYPE: PRT
<213> ORGANISM: Artificial Sequence
<220> FEATURE:
<221> NAME/KEY: SITE
<222> LOCATION: (1)...(22)
<223> OTHER INFORMATION: 22 amino acid region containing Leucine-based
      motif region from BoNT/A light chain

<400> SEQUENCE: 121

Lys Asn Phe Thr Gly Leu Phe Glu Phe Tyr Lys Leu Leu Cys Val Arg
1               5                   10                  15

Gly Ile Ile Thr Ser Lys
            20

<210> SEQ ID NO 122
<211> LENGTH: 424
<212> TYPE: PRT
<213> ORGANISM: Artificial Sequence
<220> FEATURE:
<221> NAME/KEY: PEPTIDE
<222> LOCATION: (1)...(424)
<223> OTHER INFORMATION: Chimeric LC/E (ExxxII)

<400> SEQUENCE: 122

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
            20                  25                  30

Asn Ile Met Lys Asn Ile Trp Ile Ile Pro Glu Arg Asn Val Ile Gly
        35                  40                  45

Thr Thr Pro Gln Asp Phe His Pro Pro Thr Ser Leu Lys Asn Gly Asp
    50                  55                  60

Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln Asp Ile Leu Leu
    130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
                165                 170                 175

Phe Gly Ser Ile Ala Ile Val Thr Phe Ser Pro Glu Tyr Ser Phe Arg
            180                 185                 190

Phe Asn Asp Asn Ser Met Asn Glu Phe Ile Gln Asp Pro Ala Leu Thr
        195                 200                 205

Leu Met His Glu Leu Ile His Ser Leu His Gly Leu Tyr Gly Ala Lys
    210                 215                 220

Gly Ile Thr Thr Lys Tyr Thr Ile Thr Gln Lys Gln Asn Pro Leu Ile

```
                        225                 230                 235                 240
Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
        275                 280                 285

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Ala Thr Lys Phe Gln Val Lys Cys Arg Gln Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
    370                 375                 380

Gly Gln Asn Ala Asn Leu Asn Pro Arg Ile Ile Thr Pro Ile Thr Gly
385                 390                 395                 400

Arg Gly Glu Val Lys Lys Ile Ile Arg Phe Cys Lys Asn Ile Val Ser
                405                 410                 415

Val Lys Gly Ile Arg Lys Leu Arg
            420
```

<210> SEQ ID NO 123
<211> LENGTH: 425
<212> TYPE: PRT
<213> ORGANISM: Artificial Sequence
<220> FEATURE:
<221> NAME/KEY: PEPTIDE
<222> LOCATION: (1)...(425)
<223> OTHER INFORMATION: Chimeric LC/E (NLCA/ExxxII)

<400> SEQUENCE: 123

```
Pro Phe Val Asn Lys Gln Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20

```
Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Gly Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Glu Val Lys Lys Ile Ile Arg Phe Cys Lys Asn Ile Val
                405                 410                 415

Ser Val Lys Gly Ile Arg Lys Leu Arg
            420                 425

<210> SEQ ID NO 124
<211> LENGTH: 423
<212> TYPE: PRT
<213> ORGANISM: Artificial Sequence
<220> FEATURE:
<221> NAME/KEY: DOMAIN
<222> LOCATION: (1)...(423)
<223> OTHER INFORMATION: BoNT/A-BoNT/E chimeric LC

<400> SEQUENCE: 124

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95
```

```
Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Lys Asn Phe Thr Gly Leu Phe Glu Phe Tyr Lys Leu Leu Cys Val
                405                 410                 415

Arg Gly Ile Ile Thr Ser Lys
            420

<210> SEQ ID NO 125
<211> LENGTH: 441
<212> TYPE: PRT
<213> ORGANISM: Artificial Sequence
<220> FEATURE:
<221> NAME/KEY: DOMAIN
<222> LOCATION: (1)...(441)
<223> OTHER INFORMATION: BoNT/A-BoNT/B chimeric LC

<400> SEQUENCE: 125

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gly Arg
```

```
                    20                  25                  30
Tyr Tyr Lys Ala Phe Lys Ile Thr Asp Arg Ile Trp Ile Pro Glu
                35                  40                  45
Arg Tyr Thr Phe Gly Tyr Lys Pro Glu Asp Phe Asn Lys Ser Ser Gly
                50                  55                  60
Ile Phe Asn Arg Asp Val Cys Glu Tyr Tyr Asp Pro Asp Tyr Leu Asn
65                  70                  75                  80
Thr Asn Asp Lys Lys Asn Ile Phe Phe Gln Thr Leu Ile Lys Leu Phe
                85                  90                  95
Asn Arg Ile Lys Ser Lys Pro Leu Gly Glu Lys Leu Leu Glu Met Ile
                100                 105                 110
Ile Asn Gly Ile Pro Tyr Leu Gly Asp Arg Arg Val Pro Leu Glu Glu
                115                 120                 125
Phe Asn Thr Asn Ile Ala Ser Val Thr Val Asn Lys Leu Ile Ser Asn
130                 135                 140
Pro Gly Glu Val Glu Arg Lys Lys Gly Ile Phe Ala Asn Leu Ile Ile
145                 150                 155                 160
Phe Gly Pro Gly Pro Val Leu Asn Glu Asn Glu Thr Ile Asp Ile Gly
                165                 170                 175
Ile Gln Asn His Phe Ala Ser Arg Glu Gly Phe Gly Gly Ile Met Gln
                180                 185                 190
Met Lys Phe Cys Pro Glu Tyr Val Ser Val Phe Asn Asn Val Gln Glu
                195                 200                 205
Asn Lys Gly Ala Ser Ile Phe Asn Arg Arg Gly Tyr Phe Ser Asp Pro
                210                 215                 220
Ala Leu Ile Leu Met His Glu Leu Ile His Val Leu His Gly Leu Tyr
225                 230                 235                 240
Gly Ile Lys Val Asp Asp Leu Pro Ile Val Pro Asn Glu Lys Lys Phe
                245                 250                 255
Phe Met Gln Ser Thr Asp Thr Ile Gln Ala Glu Glu Leu Tyr Thr Phe
                260                 265                 270
Gly Gly Gln Asp Pro Ser Ile Ile Ser Pro Ser Thr Asp Lys Ser Ile
                275                 280                 285
Tyr Asp Lys Val Leu Gln Asn Phe Arg Gly Ile Val Asp Arg Leu Asn
                290                 295                 300
Lys Val Leu Val Cys Ile Ser Asp Pro Asn Ile Asn Ile Asn Ile Tyr
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asn Lys Leu Tyr Lys Ser Leu
                340                 345                 350
Met Leu Gly Phe Thr Glu Ile Asn Ile Ala Glu Asn Tyr Lys Ile Lys
                355                 360                 365
Thr Arg Ala Ser Tyr Phe Ser Asp Ser Leu Pro Pro Val Lys Ile Lys
                370                 375                 380
Asn Leu Leu Asp Asn Glu Ile Tyr Thr Ile Glu Glu Gly Phe Asn Ile
385                 390                 395                 400
Ser Asp Lys Asn Met Gly Lys Glu Tyr Arg Gly Gln Asn Lys Ala Ile
                405                 410                 415
Asn Lys Gln Ala Tyr Glu Glu Ile Ser Lys Glu His Leu Ala Val Tyr
                420                 425                 430
Lys Ile Gln Met Cys Lys Ser Val Lys
                435                 440
```

<210> SEQ ID NO 126
<211> LENGTH: 423
<212> TYPE: PRT
<213> ORGANISM: Artificial Sequence
<220> FEATURE:
<221> NAME/KEY: DOMAIN
<222> LOCATION: (1)...(423)
<223> OTHER INFORMATION: BoNT/A-BoNT/E chimeric LC

<400> SEQUENCE: 126

```
Met Pro Phe Val Asn Lys Gln Phe Asn Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365
```

```
Tyr Asn Ile Ser Glu Gly Tyr Asn Ile Asn Asn Leu Lys Val Asn Phe
        370                 375                 380

Arg Gly Gln Asn Ala Asn Leu Asn Pro Arg Ile Ile Thr Pro Ile Thr
385                 390                 395                 400

Gly Lys Asn Phe Thr Gly Leu Phe Glu Phe Tyr Lys Leu Leu Cys Val
                405                 410                 415

Arg Gly Ile Ile Thr Ser Lys
            420

<210> SEQ ID NO 127
<211> LENGTH: 441
<212> TYPE: PRT
<213> ORGANISM: Artificial Sequence
<220> FEATURE:
<221> NAME/KEY: DOMAIN
<222> LOCATION: (1)...(441)
<223> OTHER INFORMATION: BoNT/A-BoNT/B chimeric LC

<400> SEQUENCE: 127

Met Pro Phe Val Asn Lys Gln Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Phe Gln Thr Leu Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
```

```
                290                 295                 300
Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asn Lys Leu Tyr Lys Ser Leu
                340                 345                 350

Met Leu Gly Phe Thr Glu Ile Asn Ile Ala Glu Asn Tyr Lys Ile Lys
                355                 360                 365

Thr Arg Ala Ser Tyr Phe Ser Asp Ser Leu Pro Pro Val Lys Ile Lys
                370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
                405                 410                 415

Asn Lys Gln Lys Asn Phe Thr Gly Leu Phe Glu Phe Tyr Lys Leu Leu
                420                 425                 430

Cys Val Arg Gly Ile Ile Thr Ser Lys
                435                 440

<210> SEQ ID NO 128
<211> LENGTH: 436
<212> TYPE: PRT
<213> ORGANISM: Artificial Sequence
<220> FEATURE:
<221> NAME/KEY: DOMAIN
<222> LOCATION: (1)...(436)
<223> OTHER INFORMATION: BoNT/A-BoNT/F chimeric LC

<400> SEQUENCE: 128

Met Pro Phe Val Asn Lys Gln Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asn Pro Ser Asp Phe Asp Pro Pro Ala Ser
50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205
```

```
Gly His Asn Ser Ser Thr Glu Ser Phe Ile Ala Asp Pro Ala Ile Ser
            210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                    245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
            275                 280                 285

Asn Leu Leu Ala Asn Tyr Glu Lys Ile Ala Thr Arg Leu Ser Glu Val
            290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                    325                 330                 335

Asn Glu Asn Lys Phe Asn Glu Ile Tyr Lys Lys Leu Tyr Ser Phe Thr
                340                 345                 350

Glu Ser Asp Leu Ala Asn Lys Phe Lys Val Lys Cys Arg Asn Thr Tyr
            355                 360                 365

Phe Ile Lys Tyr Glu Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Lys Asn
                    405                 410                 415

Phe Thr Gly Leu Phe Glu Phe Tyr Lys Leu Leu Cys Val Arg Gly Ile
                420                 425                 430

Ile Thr Ser Lys
            435

<210> SEQ ID NO 129
<211> LENGTH: 483
<212> TYPE: PRT
<213> ORGANISM: Artificial Sequence
<220> FEATURE:
<221> NAME/KEY: DOMAIN
<222> LOCATION: (1)...(483)
<223> OTHER INFORMATION: BoNT/A-BoNT/B chimeric LC

<400> SEQUENCE: 129

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Tyr Asn Asp Pro Ile Asp Asn Asn Ile Ile Met Met
    50                  55                  60

Glu Pro Pro Phe Ala Arg Gly Thr Gly Arg Tyr Tyr Lys Ala Phe Lys
65                  70                  75                  80

Ile Thr Asp Arg Ile Trp Ile Ile Pro Glu Arg Tyr Thr Phe Gly Tyr
                85                  90                  95

Lys Pro Glu Asp Phe Asn Lys Ser Ser Gly Ile Phe Asn Arg Asp Val
            100                 105                 110

Cys Glu Tyr Tyr Asp Pro Asp Tyr Leu Asn Thr Asn Asp Lys Lys Asn
        115                 120                 125
```

```
Ile Phe Phe Gln Thr Leu Ile Lys Leu Phe Asn Arg Ile Lys Ser Lys
    130                 135                 140
Pro Leu Gly Glu Lys Leu Leu Glu Met Ile Ile Asn Gly Ile Pro Tyr
145                 150                 155                 160
Leu Gly Asp Arg Arg Val Pro Leu Glu Glu Phe Asn Thr Asn Ile Ala
                165                 170                 175
Ser Val Thr Val Asn Lys Leu Ile Ser Asn Pro Gly Glu Val Glu Arg
                180                 185                 190
Lys Lys Gly Ile Phe Ala Asn Leu Ile Ile Phe Gly Pro Gly Pro Val
            195                 200                 205
Leu Asn Glu Asn Glu Thr Ile Asp Ile Gly Ile Gln Asn His Phe Ala
    210                 215                 220
Ser Arg Glu Gly Phe Gly Gly Ile Met Gln Met Lys Phe Cys Pro Glu
225                 230                 235                 240
Tyr Val Ser Val Phe Asn Asn Val Gln Glu Asn Lys Gly Ala Ser Ile
                245                 250                 255
Phe Asn Arg Arg Gly Tyr Phe Ser Asp Pro Ala Leu Ile Leu Met His
                260                 265                 270
Glu Leu Ile His Val Leu His Gly Leu Tyr Gly Ile Lys Val Asp Asp
    275                 280                 285
Leu Pro Ile Val Pro Asn Glu Lys Lys Phe Phe Met Gln Ser Thr Asp
    290                 295                 300
Thr Ile Gln Ala Glu Glu Leu Tyr Thr Phe Gly Gly Gln Asp Pro Ser
305                 310                 315                 320
Ile Ile Ser Pro Ser Thr Asp Lys Ser Ile Tyr Asp Lys Val Leu Gln
                325                 330                 335
Asn Phe Arg Gly Ile Val Asp Arg Leu Asn Lys Val Leu Val Cys Ile
                340                 345                 350
Ser Asp Pro Asn Ile Asn Ile Asn Ile Tyr Lys Asn Lys Phe Lys Asp
                355                 360                 365
Lys Tyr Lys Phe Val Glu Asp Ser Glu Gly Lys Tyr Ser Ile Asp Val
    370                 375                 380
Glu Ser Phe Asn Lys Leu Tyr Lys Ser Leu Met Leu Gly Phe Thr Glu
385                 390                 395                 400
Ile Asn Ile Ala Glu Asn Tyr Lys Ile Lys Thr Arg Ala Ser Tyr Phe
                405                 410                 415
Ser Asp Ser Leu Pro Pro Val Lys Ile Lys Asn Leu Leu Asp Asn Glu
                420                 425                 430
Ile Tyr Thr Ile Glu Glu Gly Phe Asn Ile Ser Asp Lys Asn Met Gly
            435                 440                 445
Lys Glu Tyr Arg Gly Gln Asn Lys Ala Ile Asn Lys Gln Ala Tyr Glu
    450                 455                 460
Glu Ile Ser Lys Glu His Leu Ala Val Tyr Lys Ile Gln Met Cys Lys
465                 470                 475                 480
Ser Val Lys
```

<210> SEQ ID NO 130
<211> LENGTH: 458
<212> TYPE: PRT
<213> ORGANISM: Artificial Sequence
<220> FEATURE:
<221> NAME/KEY: DOMAIN
<222> LOCATION: (1)...(458)
<223> OTHER INFORMATION: BoNT/A-BoNT/E chimeric LC

<400> SEQUENCE: 130

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Gly Phe
385                 390                 395                 400

Asn Leu Arg Asn Thr Asn Leu Ala Ala Asn Phe Asn Gly Gln Asn Thr
                405                 410                 415

Glu Ile Asn Asn Met Asn Phe Thr Lys Leu Lys Asn Phe Thr Gly Leu
```

```
                  420              425              430
Phe Glu Phe Tyr Lys Leu Leu Cys Val Arg Gly Ile Ile Thr Ser Lys
            435              440              445
Asn Ile Val Ser Val Lys Gly Ile Arg Lys
        450              455

<210> SEQ ID NO 131
<211> LENGTH: 443
<212> TYPE: PRT
<213> ORGANISM: Artificial Sequence
<220> FEATURE:
<221> NAME/KEY: DOMAIN
<222> LOCATION: (1)...(443)
<223> OTHER INFORMATION: BoNT/A

```
Asp Val Phe Glu Ala Lys Tyr Gly Leu Asp Lys Asp Ala Ser Gly Ile
                325                 330                 335

Tyr Ser Val Asn Ile Asn Lys Phe Asn Asp Ile Phe Lys Lys Leu Tyr
            340                 345                 350

Ser Phe Thr Glu Phe Asp Leu Ala Thr Lys Phe Gln Val Lys Cys Arg
        355                 360                 365

Gln Thr Tyr Ile Gly Gln Tyr Lys Tyr Phe Lys Leu Ser Asn Leu Leu
    370                 375                 380

Asn Asp Ser Ile Tyr Asn Ile Ser Glu Gly Phe Asn Leu Arg Asn Thr
385                 390                 395                 400

Asn Leu Ala Ala Asn Phe Asn Gly Gln Asn Thr Glu Ile Asn Asn Met
                405                 410                 415

Asn Phe Thr Lys Leu Lys Asn Phe Thr Gly Leu Phe Glu Phe Tyr Lys
            420                 425                 430

Leu Leu Cys Val Arg Gly Ile Ile Thr Ser Lys
        435                 440

<210> SEQ ID NO 132
<211> LENGTH: 461
<212> TYPE: PRT
<213> ORGANISM: Artificial Sequence
<220> FEATURE:
<221> NAME/KEY: DOMAIN
<222> LOCATION: (1)...(461)
<223> OTHER INFORMATION: BoNT/A-BoNT/B chimeric LC

<400> SEQUENCE: 132

Met Pro Val Thr Ile Asn Asn Phe Asn Met Pro Phe Val Asn Lys Gln
1               5                   10                  15

Phe Asn Tyr Lys Asp Pro Val Asn Gly Val Asp Ile Ala Tyr Ile Lys
            20                  25                  30

Ile Pro Asn Ala Gly Gln Met Ile Met Met Glu Pro Pro Phe Ala Arg
        35                  40                  45

Gly Thr Gly Arg Tyr Tyr Lys Ala Phe Lys Ile Thr Asp Arg Ile Trp
    50                  55                  60

Ile Ile Pro Glu Arg Tyr Thr Phe Gly Tyr Lys Pro Glu Asp Phe Asn
65                  70                  75                  80

Lys Ser Ser Gly Ile Phe Asn Arg Asp Val Cys Glu Tyr Tyr Asp Pro
                85                  90                  95

Asp Tyr Leu Asn Thr Asn Asp Lys Lys Asn Ile Phe Phe Gln Thr Leu
            100                 105                 110

Ile Lys Leu Phe Asn Arg Ile Lys Ser Lys Pro Leu Gly Glu Lys Leu
        115                 120                 125

Leu Glu Met Ile Ile Asn Gly Ile Pro Tyr Leu Gly Asp Arg Arg Val
    130                 135                 140

Pro Leu Glu Glu Phe Asn Thr Asn Ile Ala Ser Val Thr Val Asn Lys
145                 150                 155                 160

Leu Ile Ser Asn Pro Gly Glu Val Glu Arg Lys Lys Gly Ile Phe Ala
                165                 170                 175

Asn Leu Ile Ile Phe Gly Pro Gly Pro Val Leu Asn Glu Asn Glu Thr
            180                 185                 190

Ile Asp Ile Gly Ile Gln Asn His Phe Ala Ser Arg Glu Gly Phe Gly
        195                 200                 205

Gly Ile Met Gln Met Lys Phe Cys Pro Glu Tyr Val Ser Val Phe Asn
    210                 215                 220

Asn Val Gln Glu Asn Lys Gly Ala Ser Ile Phe Asn Arg Arg Gly Tyr
225                 230                 235                 240
```

```
Phe Ser Asp Pro Ala Leu Ile Leu Met His Glu Leu Ile His Val Leu
                245                 250                 255

His Gly Leu Tyr Gly Ile Lys Val Asp Asp Leu Pro Ile Val Pro Asn
            260                 265                 270

Glu Lys Lys Phe Phe Met Gln Ser Thr Asp Thr Ile Gln Ala Glu Glu
            275                 280                 285

Leu Tyr Thr Phe Gly Gly Gln Asp Pro Ser Ile Ile Ser Pro Ser Thr
    290                 295                 300

Asp Lys Ser Ile Tyr Asp Lys Val Leu Gln Asn Phe Arg Gly Ile Val
305                 310                 315                 320

Asp Arg Leu Asn Lys Val Leu Val Cys Ile Ser Asp Pro Asn Ile Asn
                325                 330                 335

Ile Asn Ile Tyr Lys Asn Lys Phe Lys Asp Lys Tyr Lys Phe Val Glu
                340                 345                 350

Asp Ser Glu Gly Lys Tyr Ser Ile Asp Val Glu Ser Phe Asn Lys Leu
            355                 360                 365

Tyr Lys Ser Leu Met Leu Gly Phe Thr Glu Ile Asn Ile Ala Glu Asn
    370                 375                 380

Tyr Lys Ile Lys Thr Arg Ala Ser Tyr Phe Ser Asp Ser Leu Pro Pro
385                 390                 395                 400

Val Lys Ile Lys Asn Leu Leu Asp Asn Glu Ile Gly Phe Asn Leu Arg
                405                 410                 415

Asn Thr Asn Leu Ala Ala Asn Phe Asn Gly Gln Asn Thr Glu Ile Asn
                420                 425                 430

Asn Met Asn Phe Thr Lys Leu Lys Asn Phe Thr Gly Leu Phe Glu Phe
            435                 440                 445

Tyr Lys Leu Leu Cys Val Arg Gly Ile Ile Thr Ser Lys
    450                 455                 460

<210> SEQ ID NO 133
<211> LENGTH: 456
<212> TYPE: PRT
<213> ORGANISM: Artificial Sequence
<220> FEATURE:
<221> NAME/KEY: DOMAIN
<222> LOCATION: (1)...(456)
<223> OTHER INFORMATION: BoNT/A-BoNT/F chimeric LC

<400> SEQUENCE: 133

Met Pro Val Ala Ile Asn Ser Phe Asn Met Pro Phe Val Asn Lys Gln
1               5                   10                  15

Phe Asn Tyr Lys Asp Pro Val Asn Gly Val Asp Ile Ala Tyr Ile Lys
            20                  25                  30

Ile Pro Asn Ala Gly Gln Met Leu Tyr Met Gln Ile Pro Tyr Glu Glu
        35                  40                  45

Lys Ser Lys Lys Tyr Tyr Lys Ala Phe Glu Ile Met Arg Asn Val Trp
    50                  55                  60

Ile Ile Pro Glu Arg Asn Thr Ile Gly Thr Asn Pro Ser Asp Phe Asp
65                  70                  75                  80

Pro Pro Ala Ser Leu Lys Asn Gly Ser Ser Ala Tyr Tyr Asp Pro Asn
                85                  90                  95

Tyr Leu Thr Thr Asp Ala Glu Lys Asp Arg Tyr Leu Lys Thr Thr Ile
            100                 105                 110

Lys Leu Phe Lys Arg Ile Asn Ser Asn Pro Ala Gly Lys Val Leu Leu
        115                 120                 125

Gln Glu Ile Ser Tyr Ala Lys Pro Tyr Leu Gly Asn Asp His Thr Pro
```

-continued

```
    130                 135                 140

Ile Asp Glu Phe Ser Pro Val Thr Arg Thr Thr Ser Val Asn Ile Lys
145                 150                 155                 160

Leu Ser Thr Asn Val Glu Ser Ser Met Leu Leu Asn Leu Leu Val Leu
                165                 170                 175

Gly Ala Gly Pro Asp Ile Phe Glu Ser Cys Cys Tyr Pro Val Arg Lys
            180                 185                 190

Leu Ile Asp Pro Asp Val Val Tyr Asp Pro Ser Asn Tyr Gly Phe Gly
        195                 200                 205

Ser Ile Asn Ile Val Thr Phe Ser Pro Glu Tyr Glu Tyr Thr Phe Asn
    210                 215                 220

Asp Ile Ser Gly Gly His Asn Ser Ser Thr Glu Ser Phe Ile Ala Asp
225                 230                 235                 240

Pro Ala Ile Ser Leu Ala His Glu Leu Ile His Ala Leu His Gly Leu
                245                 250                 255

Tyr Gly Ala Arg Gly Val Thr Tyr Glu Glu Thr Ile Glu Val Lys Gln
            260                 265                 270

Ala Pro Leu Met Ile Ala Glu Lys Pro Ile Arg Leu Glu Glu Phe Leu
        275                 280                 285

Thr Phe Gly Gly Gln Asp Leu Asn Ile Ile Thr Ser Ala Met Lys Glu
    290                 295                 300

Lys Ile Tyr Asn Asn Leu Leu Ala Asn Tyr Glu Lys Ile Ala Thr Arg
305                 310                 315                 320

Leu Ser Glu Val Asn Ser Ala Pro Pro Glu Tyr Asp Ile Asn Glu Tyr
                325                 330                 335

Lys Asp Tyr Phe Gln Trp Lys Tyr Gly Leu Asp Lys Asn Ala Asp Gly
            340                 345                 350

Ser Tyr Thr Val Asn Glu Asn Lys Phe Asn Glu Ile Tyr Lys Lys Leu
        355                 360                 365

Tyr Ser Phe Thr Glu Ser Asp Leu Ala Asn Lys Phe Lys Val Lys Cys
    370                 375                 380

Arg Asn Thr Tyr Phe Ile Lys Tyr Glu Phe Leu Lys Val Pro Asn Leu
385                 390                 395                 400

Leu Asp Asp Asp Ile Tyr Gly Phe Asn Leu Arg Asn Thr Asn Leu Ala
                405                 410                 415

Ala Asn Phe Asn Gly Gln Asn Thr Glu Ile Asn Asn Met Asn Phe Thr
            420                 425                 430

Lys Leu Lys Asn Phe Thr Gly Leu Phe Glu Phe Tyr Lys Leu Leu Cys
        435                 440                 445

Val Arg Gly Ile Ile Thr Ser Lys
    450                 455
```

<210> SEQ ID NO 134
<211> LENGTH: 449
<212> TYPE: PRT
<213> ORGANISM: Artificial Sequence
<220> FEATURE:
<221> NAME/KEY: DOMAIN
<222> LOCATION: (1)...(449)
<223> OTHER INFORMATION: BoNT/A-BoNT/E chimeric LC

<400> SEQUENCE: 134

```
Met Pro Lys Ile Asn Ser Phe Asn Tyr Asn Asp Pro Val Thr Ile Asn
1               5                   10                  15

Asn Phe Asn Tyr Asp Arg Thr Ile Leu Tyr Ile Lys Pro Gly Gly Cys
            20                  25                  30
```

```
Gln Glu Phe Tyr Lys Ser Phe Asn Ile Met Lys Asn Ile Trp Ile Ile
         35                  40                  45

Pro Glu Arg Asn Val Ile Gly Thr Thr Pro Gln Asp Phe His Pro Pro
 50                  55                  60

Thr Ser Leu Lys Asn Gly Asp Ser Ser Tyr Tyr Asp Pro Asn Tyr Leu
 65                  70                  75                  80

Gln Ser Asp Glu Glu Lys Asp Arg Phe Leu Lys Ile Val Thr Lys Ile
                 85                  90                  95

Phe Asn Arg Ile Asn Asn Asn Leu Ser Gly Gly Ile Leu Leu Glu Glu
                100                 105                 110

Leu Ser Lys Ala Asn Pro Tyr Leu Gly Asn Asp Asn Thr Pro Asp Asn
            115                 120                 125

Gln Phe His Ile Gly Asp Ala Ser Ala Val Glu Ile Lys Phe Ser Asn
        130                 135                 140

Gly Ser Gln Asp Ile Leu Leu Pro Asn Val Ile Met Gly Ala Glu
145                 150                 155                 160

Pro Asp Leu Phe Glu Thr Asn Ser Ser Asn Ile Ser Leu Arg Asn Asn
                165                 170                 175

Tyr Met Pro Ser Asn His Gly Phe Gly Ser Ile Ala Ile Val Thr Phe
                180                 185                 190

Ser Pro Glu Tyr Ser Phe Arg Phe Asn Asp Asn Ser Met Asn Glu Phe
            195                 200                 205

Ile Gln Asp Pro Ala Leu Thr Leu Met His Glu Leu Ile His Ser Leu
210                 215                 220

His Gly Leu Tyr Gly Ala Lys Gly Ile Thr Thr Lys Tyr Thr Ile Thr
225                 230                 235                 240

Gln Lys Gln Asn Pro Leu Ile Thr Asn Ile Arg Gly Thr Asn Ile Glu
                245                 250                 255

Glu Phe Leu Thr Phe Gly Gly Thr Asp Leu Asn Ile Ile Thr Ser Ala
            260                 265                 270

Gln Ser Asn Asp Ile Tyr Thr Asn Leu Leu Ala Asp Tyr Lys Lys Ile
        275                 280                 285

Ala Ser Lys Leu Ser Lys Val Gln Val Ser Asn Pro Leu Leu Asn Pro
290                 295                 300

Tyr Lys Asp Val Phe Glu Ala Lys Tyr Gly Leu Asp Lys Asp Ala Ser
305                 310                 315                 320

Gly Ile Tyr Ser Val Asn Ile Asn Lys Phe Asn Asp Ile Phe Lys Lys
                325                 330                 335

Leu Tyr Ser Phe Thr Glu Phe Asp Leu Ala Thr Lys Phe Gln Val Lys
            340                 345                 350

Cys Arg Gln Thr Tyr Ile Gly Gln Tyr Lys Tyr Phe Lys Leu Ser Asn
        355                 360                 365

Leu Leu Asn Asp Ser Ile Tyr Asn Ile Ser Glu Gly Tyr Asn Ile Asn
370                 375                 380

Asn Leu Lys Val Asn Phe Arg Gly Gln Asn Ala Asn Leu Asn Pro Arg
385                 390                 395                 400

Ile Ile Thr Pro Ile Thr Gly Arg Gly Leu Val Lys Lys Ile Ile Arg
                405                 410                 415

Phe Cys Lys Asn Asn Met Asn Phe Thr Lys Leu Lys Asn Phe Thr Gly
            420                 425                 430

Leu Phe Glu Phe Tyr Lys Leu Leu Cys Val Arg Gly Ile Ile Thr Ser
        435                 440                 445

Lys
```

<210> SEQ ID NO 135
<211> LENGTH: 459
<212> TYPE: PRT
<213> ORGANISM: Artificial Sequence
<220> FEATURE:
<221> NAME/KEY: DOMAIN
<222> LOCATION: (1)...(459)
<223> OTHER INFORMATION: BoNT/A-BoNT/B-BoNT/F chimeric LC

<400> SEQUENCE: 135

```
Met Pro Val Ala Ile Asn Ser Phe Asn Tyr Asn Asp Val Thr Ile Asn
1               5                   10                  15

Asn Phe Asn Tyr Thr Ile Leu Tyr Met Gln Ile Pro Tyr Glu Glu Lys
            20                  25                  30

Ser Lys Lys Tyr Tyr Lys Ala Phe Glu Ile Met Arg Asn Val Trp Ile
        35                  40                  45

Ile Pro Glu Arg Asn Thr Ile Gly Thr Asn Pro Ser Asp Phe Asp Pro
    50                  55                  60

Pro Ala Ser Leu Lys Asn Gly Ser Ser Ala Tyr Tyr Asp Pro Asn Tyr
65                  70                  75                  80

Leu Thr Thr Asp Ala Glu Lys Asp Arg Tyr Leu Lys Thr Thr Ile Lys
                85                  90                  95

Leu Phe Lys Arg Ile Asn Ser Asn Pro Ala Gly Lys Val Leu Leu Gln
            100                 105                 110

Glu Ile Ser Tyr Ala Lys Pro Tyr Leu Gly Asn Asp His Thr Pro Ile
        115                 120                 125

Asp Glu Phe Ser Pro Val Thr Arg Thr Thr Ser Val Asn Ile Lys Leu
    130                 135                 140

Ser Thr Asn Val Glu Ser Ser Met Leu Leu Asn Leu Leu Val Leu Gly
145                 150                 155                 160

Ala Gly Pro Asp Ile Phe Glu Ser Cys Cys Tyr Pro Val Arg Lys Leu
                165                 170                 175

Ile Asp Pro Asp Val Val Tyr Asp Pro Ser Asn Tyr Gly Phe Gly Ser
            180                 185                 190

Ile Asn Ile Val Thr Phe Ser Pro Glu Tyr Glu Tyr Thr Phe Asn Asp
        195                 200                 205

Ile Ser Gly Gly His Asn Ser Ser Thr Glu Ser Phe Ile Ala Asp Pro
    210                 215                 220

Ala Ile Ser Leu Ala His Glu Leu Ile His Ala Leu His Gly Leu Tyr
225                 230                 235                 240

Gly Ala Arg Gly Val Thr Tyr Glu Glu Thr Ile Glu Val Lys Gln Ala
                245                 250                 255

Pro Leu Met Ile Ala Glu Lys Pro Ile Arg Leu Glu Glu Phe Leu Thr
            260                 265                 270

Phe Gly Gly Gln Asp Leu Asn Ile Ile Thr Ser Ala Met Lys Glu Lys
        275                 280                 285

Ile Tyr Asn Asn Leu Leu Ala Asn Tyr Glu Lys Ile Ala Thr Arg Leu
    290                 295                 300

Ser Glu Val Asn Ser Ala Pro Pro Glu Tyr Asp Ile Asn Glu Tyr Lys
305                 310                 315                 320

Asp Tyr Phe Gln Trp Lys Tyr Gly Leu Asp Lys Asn Ala Asp Gly Ser
                325                 330                 335

Tyr Thr Val Asn Glu Asn Lys Phe Asn Glu Ile Tyr Lys Lys Leu Tyr
            340                 345                 350

Ser Phe Thr Glu Ser Asp Leu Ala Asn Lys Phe Lys Val Lys Cys Arg
        355                 360                 365
```

```
Asn Thr Tyr Phe Ile Lys Tyr Glu Phe Leu Lys Val Pro Asn Leu Leu
    370                 375                 380

Asp Asp Asp Ile Tyr Thr Val Ser Glu Gly Phe Asn Ile Gly Asn Leu
385                 390                 395                 400

Ala Val Asn Asn Arg Gly Gln Ser Ile Lys Leu Asn Pro Lys Ile Ile
                405                 410                 415

Asp Ser Ile Pro Asp Lys Gly Leu Val Glu Lys Asn Asn Met Asn Phe
            420                 425                 430

Thr Lys Leu Lys Asn Phe Thr Gly Leu Phe Glu Phe Tyr Lys Leu Leu
                435                 440                 445

Cys Val Arg Gly Ile Ile Thr Ser Lys Arg Lys
    450                 455

<210> SEQ ID NO 136
<211> LENGTH: 424
<212> TYPE: PRT
<213> ORGANISM: Clostridium botulinum serotype E (Beluga)

<400> SEQUENCE: 136

Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
                20                  25                  30

Asn Ile Met Lys Asn Ile Trp Ile Ile Pro Glu Arg Asn Val Ile Gly
            35                  40                  45

Thr Thr Pro Gln Asp Phe His Pro Pro Thr Ser Leu Lys Asn Gly Asp
        50                  55                  60

Ser Ser Tyr Tyr Asp Pro Asn Tyr Leu Gln Ser Asp Glu Glu Lys Asp
65                  70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
        115                 120                 125

Ser Ala Val Glu Ile Lys Phe Ser Asn Gly Ser Gln Asp Ile Leu Leu
130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
                165                 170                 175

Phe Gly Ser Ile Ala Ile Val Thr Phe Ser Pro Glu Tyr Ser Phe Arg
            180                 185                 190

Phe Asn Asp Asn Ser Met Asn Glu Phe Ile Gln Asp Pro Ala Leu Thr
        195                 200                 205

Leu Met His Glu Leu Ile His Ser Leu His Gly Leu Tyr Gly Ala Lys
    210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
                245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
        275                 280                 285
```

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Ala Thr Lys Phe Gln Val Lys Cys Arg Gln Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
370                 375                 380

Gly Gln Asn Ala Asn Leu Asn Pro Arg Ile Ile Thr Pro Ile Thr Gly
385                 390                 395                 400

Arg Gly Leu Val Lys Lys Ile Ile Arg Phe Cys Lys Asn Ile Val Ser
                405                 410                 415

Val Lys Gly Ile Arg Lys Leu Arg
            420

<210> SEQ ID NO 137
<211> LENGTH: 2453
<212> TYPE: DNA
<213> ORGANISM: Clostridium botulinum serotype E (Beluga)

<400> SEQUENCE: 137
ccaaaaatta atagttttaa ttataatgat cctgttaatg atagaacagg tttttaatta      60
tcaaaattaa tattactagg acaattacta tcttgtattt tatatattaa accaggcggt     120
tgtcaagaat tttataaatc ataaaatata taatttggtc cgccaacagt tcttaaaata     180
tttagtttta atattatgaa aaatatttgg ataattccag agagaaatgt aaaattataa     240
tactttttat aaacctatta aggtctctct ttacatattg gtacaacccc ccaagatttt     300
catccgccta cttcattaaa ataaccatgt tgggggttc taaaagtagc ggatgaagta     360
attttaatgg agatagtagt tattatgacc ctaattattt acaaagtgat ttacctctat     420
catcaataat actgggatta taaatgtttt cactagaaga aaaggataga ttttttaaaaa     480 tagtcacaaa atatttaat cttctttttcc tatctaaaaa ttttttatcag tgttttata     540 aattaagaat aaataataat ctttcaggag ggattttatt agaagaactg tcttatttat     600
tattagaaag tcctccctaa ataatcttc ttgactcaaa agctaatcca tatttaggga     660
atgataatac tccagataat agttttcgat taggtataaa tcccttacta ttatgaggtc     720
tattacaatt ccatattggt gatgcatcag cagttgagat taaattctca gttaaggtat     780
aaccactacg tagtcgtcaa ctctaattta agagtaatgg tagccaagac atactattac     840
ctaatgttat tataatggga ttaccatcgg ttctgtatga taatggatta caataatatt     900
accctgcaga gcctgattta tttgaaacta acagttccaa tatttctcta cgtctcggac     960
taaataaact ttgattgtca aggttataaa gagatagaaa taattatatg ccaagcaatc    1020
acggttttgg atcaatagct tctttattaa tatacggttc gttagtgcca aaacctagtt    1080
atcgaatagt aacattctca cctgaatatt cttttagatt taatgataat tatcattgta    1140
agagtggact tataagaaaa tctaaattac tattaagtat gaatgaattt attcaagatc    1200
ctgctcttac attaatgcat tcatacttac ttaaataagt tctaggacga gaatgtaatt    1260
acgtagaatt aatacattca ttacatggac tatatggggc taaagggatt cttaattatg    1320

```
taagtaatgt acctgatata ccccgatttc cctaaactac aaagtatact ataacacaaa    1380
aacaaaatcc cctaataaca tgatgtttca tatgatattg tgtttttgtt ttaggggatt    1440
attgtaatat aagaggtaca aatattgaag aattcttaac ttttggaggt ttatattctc    1500 catgttttata acttcttaag aattgaaaac ctccaactga tttaaacatt attactagtg    1560
ctcagtccaa tgatatctat tgactaaatt tgtaataatg atcacgagtc aggttactat    1620
agataactaa tcttctagct gattataaaa aaatagcgtc taaacttagc tgattagaag    1680
atcgactaat attttttttat cgcagatttg aatcgaaagt acaagtatct aatccactac    1740
ttaatcctta taaagatgtt tttcatgttc atagattagg tgatgaatta ggaatatttc    1800
tacaatcggt aaatataaac aaatttaatg atatttttaa aaaattatac agccatttat    1860
atttgtttaa attactataa aaattttttta atatgagctt tacggaattt gatttagcaa    1920
ctaaatttca agttaaatgt tcgaaatgcc ttaaactaaa tcgttgattt aaagttcaat    1980
ttacaaggca aacttatatt ggacagtata aatacttcaa actttcaaac tccgtttgaa    2040
tataacctgt catatttatg aagtttgaaa gtttgttgtt aaatgattct atttataata    2100
tatcagaagg ctataatata aacaatttac taagataaat attatatagt cttccgatat    2160
tatataataa tttaaaggta aattttagag gacagaatgc aaatttaaat ttattaaatt    2220
tccatttaaa atctcctgtc ttacgtttaa atttacctag aattattaca ccaattacag    2280
gtagaggact agtaaaaaaa ggatcttaat aatgtggtta atgtccatct cctgatcatt    2340
tttttatcat tagattttgt aaaaatattg tttctgtaaa aggcataagg tagtaatcta    2400 aaacatttttt ataacaaaga catttttccgt attccaagct tcgcttcgaa gcg          2453
```

<210> SEQ ID NO 138
<211> LENGTH: 425
<212> TYPE: PRT
<213> ORGANISM: Artificial Sequence
<220> FEATURE:
<221> NAME/KEY: PEPTIDE
<222> LOCATION: (1)...(425)
<223> OTHER INFORMATION: Chimeric BoNT/E (NLCA)

<400> SEQUENCE: 138

```
Pro Phe Val Asn Lys Gln Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160
```

```
Asn Ser Ser Asn Ile Ser Leu Arg Asn Asn Tyr Met Pro Ser Asn His
            165                 170                 175
Gly Phe Gly Ser Ile Ala Ile Val Thr Phe Ser Pro Glu Tyr Ser Phe
        180                 185                 190
Arg Phe Asn Asp Asn Ser Met Asn Glu Phe Ile Gln Asp Pro Ala Leu
        195                 200                 205
Thr Leu Met His Glu Leu Ile His Ser Leu His Gly Leu Tyr Gly Ala
210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
            245                 250                 255
Gly Thr Asp Leu Asn Ile Ile Thr Ser Ala Gln Ser Asn Asp Ile Tyr
        260                 265                 270
Thr Asn Leu Leu Ala Asp Tyr Lys Lys Ile Ala Ser Lys Leu Ser Lys
        275                 280                 285
Val Gln Val Ser Asn Pro Leu Leu Asn Pro Tyr Lys Asp Val Phe Glu
    290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
            325                 330                 335
Phe Asp Leu Ala Thr Lys Phe Gln Val Lys Cys Arg Gln Thr Tyr Ile
        340                 345                 350
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Asn Asn Leu Lys Val Asn Phe
370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
            405                 410                 415
Ser Val Lys Gly Ile Arg Lys Leu Arg
        420                 425

<210> SEQ ID NO 139
<211> LENGTH: 2550
<212> TYPE: DNA
<213> ORGANISM: Artificial Sequence
<220> FEATURE:
<221> NAME/KEY: mat_peptide
<222> LOCATION: (1)...(2550)
<223> OTHER INFORMATION: Chimeric BoNT/E (NLCA)

<400> SEQUENCE: 139
ccatttgtta ataaacagtt taattataat gatcctgtta atgatggtaa acaattattt      60
gtcaaattaa tattactagg acaattacta agaacaattt tatatattaa accaggcggt    120
tgtcaagaat ttattccttg ttaaaatata taatttggtc cgccaacagt tcttaaaata    180
aaatcattta atattatgaa aaatatttgg ataattccag agagatttag taaattataa    240 tacttttat aaacctatta aggtctctct aatgtaattg gtacaacccc ccaagatttt    300
catccgccta cttcattaca ttaaccatgt tgggggttc taaagtagg cggatgaagt    360 ttaaaaaatg gagatagtag ttattatgac cctaattatt tacaaaattt tttacctcta    420
tcatcaataa tactgggatt aataaatgtt agtgatgaag aaaaggatag atttttaaaa    480
atagtcacaa aaatatcact acttcttttc ctatctaaaa attttttatca gtgttttat    540
```

```
tttaatagaa taaataataa tctttcagga gggattttat tagaaaaatt atcttattta    600
ttattagaaa gtcctcccta aaataatctt gaactgtcaa aagctaatcc atatttaggg    660
aatgataata ctccacttga cagttttcga ttaggtataa atcccttact attatgaggt    720
gataatcaat tccatattgg tgatgcatca gcagttgaga ttaaactatt agttaaggta    780
taaccactac gtagtcgtca actctaattt ttctcaaatg gtagccaaga catactatta   840
cctaatgtta ttataaagag tttaccatcg gttctgtatg ataatggatt acaataatat    900
atgggagcag agcctgattt atttgaaact aacagttcca atatttaccc tcgtctcgga    960
ctaaataaac tttgattgtc aaggttataa tctctaagaa ataattatat gccaagcaat   1020
cacggttttg gatcaagaga ttctttatta atatacggtt cgttagtgcc aaaacctagt   1080
atagctatag taacattctc acctgaatat tcttttagat ttaattatcg atatcattgt   1140
aagagtggac ttataagaaa atctaaatta gataatagta tgaatgaatt tattcaagat   1200
cctgctctta cattactatt atcatactta cttaaataag ttctaggacg agaatgtaat   1260
atgcatgaat taatacattc attacatgga ctatatgggg ctaaatacgt acttaattat   1320
gtaagtaatg tacctgatat accccgattt gggattacta caaagtatac tataacacaa   1380
aaacaaaatc ccctacccta atgatgtttc atatgatatt gtgttttttgt tttagggggat   1440
ataacaaata taagaggtac aaatattgaa gaattcttaa cttttattg tttatattct   1500
ccatgtttat aacttcttaa gaattgaaaa ggaggtactg atttaaacat tattactagt   1560
gctcagtcca atgatcctcc atgactaaat ttgtaataat gatcacgagt caggttacta   1620
atctatacta atcttctagc tgattataaa aaaatagcgt ctaaatagat atgattagaa   1680
gatcgactaa tatttttta tcgcagattt cttagcaaag tacaagtatc taatccacta   1740
cttaatcctt ataagaatc gtttcatgtt catagattag gtgatgaatt aggaatattt   1800
gatgttttg aagcaaagta tggattagat aaagatgcta gcggactaca aaaacttcgt   1860
ttcatacta atctatttct acgatcgcct atttattcgg taaatataaa caaatttaat   1920
gatatttta aaaaataaat aagccattta tatttgttta aattactata aaaatttttt   1980
ttatacagct ttacggaatt tgatttagca actaaatttc aagttaatat gtcgaaatgc   2040
cttaaactaa atcgttgatt taaagttcaa aaatgtaggc aaactatat tggacagtat    2100
aaatacttca aacttttttac atccgtttga atataacctg tcatatttat gaagtttgaa   2160
tcaaacttgt taaatgattc tatttataat atatcagaag gctatagttt gaacaattta   2220
ctaagataaa tattatatag tcttccgata atataaata atttaaaggt aaattttaga   2280
ggacagaatg caaatttata tttattaaat ttccatttaa aatctcctgt cttacgttta   2340
ttaaatccta gaattattac accaattaca ggtagaggac tagtaaattt aggatcttaa   2400
taatgtggtt aatgtccatc tcctgatcat aaaaaaatca ttagattttg taaaaatatt   2460
gtttctgtaa aaggcttttt ttagtaatct aaaacatttt tataacaaag acattttccg   2520
ataaggaagc ttcgctattc cttcgaagcg                                    2550
```

<210> SEQ ID NO 140
<211> LENGTH: 424
<212> TYPE: PRT
<213> ORGANISM: Artificial Sequence
<220> FEATURE:
<221> NAME/KEY: PEPTIDE
<222> LOCATION: (1)...(424)
<223> OTHER INFORMATION: Chimeric BoNT/E (ExxxLL)

<400> SEQUENCE: 140

```
Pro Lys Ile Asn Ser Phe Asn Tyr Asn Asp Pro Val Asn Asp Arg Thr
1               5                   10                  15

Ile Leu Tyr Ile Lys Pro Gly Gly Cys Gln Glu Phe Tyr Lys Ser Phe
            20                  25                  30

Asn Ile Met Lys Asn Ile Trp Ile Pro Glu Arg Asn Val Ile Gly
        35                  40                  45

Thr Thr Pro Gln Asp Phe His Pro Pro Thr Ser Leu Lys Asn Gly Asp
        50                  55                  60

Ser Ser Tyr Tyr Asp Pro Asn Tyr Leu Gln Ser Asp Glu Glu Lys Asp
65              70                  75                  80

Arg Phe Leu Lys Ile Val Thr Lys Ile Phe Asn Arg Ile Asn Asn Asn
                85                  90                  95

Leu Ser Gly Gly Ile Leu Leu Glu Glu Leu Ser Lys Ala Asn Pro Tyr
            100                 105                 110

Leu Gly Asn Asp Asn Thr Pro Asp Asn Gln Phe His Ile Gly Asp Ala
            115                 120                 125

Ser Ala Val Glu Ile Lys Phe Ser Asn Gly Ser Gln Asp Ile Leu Leu
130                 135                 140

Pro Asn Val Ile Ile Met Gly Ala Glu Pro Asp Leu Phe Glu Thr Asn
145                 150                 155                 160

Ser Ser Asn Ile Ser Leu Arg Asn Asn Tyr Met Pro Ser Asn His Gly
                165                 170                 175

Phe Gly Ser Ile Ala Ile Val Thr Phe Ser Pro Glu Tyr Ser Phe Arg
            180                 185                 190

Phe Asn Asp Asn Ser Met Asn Glu Phe Ile Gln Asp Pro Ala Leu Thr
            195                 200                 205

Leu Met His Glu Leu Ile His Ser Leu His Gly Leu Tyr Gly Ala Lys
        210                 215                 220

Gly Ile Thr Thr Lys Tyr Thr Ile Thr Gln Lys Gln Asn Pro Leu Ile
225                 230                 235                 240

Thr Asn Ile Arg Gly Thr Asn Ile Glu Glu Phe Leu Thr Phe Gly Gly
            245                 250                 255

Thr Asp Leu Asn Ile Ile Thr Ser Ala Gln Ser Asn Asp Ile Tyr Thr
            260                 265                 270

Asn Leu Leu Ala Asp Tyr Lys Lys Ile Ala Ser Lys Leu Ser Lys Val
            275                 280                 285

Gln Val Ser Asn Pro Leu Leu Asn Pro Tyr Lys Asp Val Phe Glu Ala
    290                 295                 300

Lys Tyr Gly Leu Asp Lys Asp Ala Ser Gly Ile Tyr Ser Val Asn Ile
305                 310                 315                 320

Asn Lys Phe Asn Asp Ile Phe Lys Lys Leu Tyr Ser Phe Thr Glu Phe
                325                 330                 335

Asp Leu Ala Thr Lys Phe Gln Val Lys Cys Arg Gln Thr Tyr Ile Gly
            340                 345                 350

Gln Tyr Lys Tyr Phe Lys Leu Ser Asn Leu Leu Asn Asp Ser Ile Tyr
        355                 360                 365

Asn Ile Ser Glu Gly Tyr Asn Ile Asn Asn Leu Lys Val Asn Phe Arg
        370                 375                 380

Gly Gln Asn Ala Asn Leu Asn Pro Arg Ile Ile Thr Pro Ile Thr Gly
385                 390                 395                 400

Arg Gly Glu Val Lys Lys Leu Leu Arg Phe Cys Lys Asn Ile Val Ser
                405                 410                 415

Val Lys Gly Ile Arg Lys Leu Arg
```

<210> SEQ ID NO 141
<211> LENGTH: 2544
<212> TYPE: DNA
<213> ORGANISM: Artificial Sequence
<220> FEATURE:
<221> NAME/KEY: mat_peptide
<222> LOCATION: (1)...(2544)
<223> OTHER INFORMATION: Chimeric BoNT/E (ExxxLL)

<400> SEQUENCE: 141

| | | | | | |
|---|---|---|---|---|---|
| ccaaaaatta | atagtttttaa | ttataatgat | cctgttaatg | atagaacagg | ttttttaatta | 60 |
| tcaaaattaa | tattactagg | acaattacta | tcttgtattt | tatatattaa | accaggcggt | 120 |
| tgtcaagaat | tttataaatc | ataaaatata | taatttggtc | cgccaacagt | tcttaaaata | 180 |
| tttagtttta | atattatgaa | aaatatttgg | ataattccag | agagaaatgt | aaaattataa | 240 |
| tacttttat | aaacctatta | aggtctctct | ttacatattg | gtacaacccc | ccaagatttt | 300 |
| catccgccta | cttcattaaa | ataaccatgt | tgggggttc | taaaagtagg | cggatgaagt | 360 |
| aatttttaatg | gagatagtag | ttattatgac | cctaattatt | tacaaagtga | tttacctcta | 420 |
| tcatcaataa | tactgggatt | aataaatgtt | tcactagaag | aaaaggatag | attttttaaaa | 480 |
| atagtcacaa | aaatatttaa | tcttcttttc | ctatctaaaa | atttttatca | gtgttttttat | 540 |
| aaattaagaa | taaataataa | tcttttcagga | gggatttttat | tagaagaact | gtcttatta | 600 |
| ttattagaaa | gtcctcccta | aaataatctt | cttgactcaa | aagctaatcc | atatttaggg | 660 |
| aatgataata | ctccagataa | tagttttcga | ttaggtataa | atcccttact | attatgaggt | 720 |
| ctattacaat | tccatattgg | tgatgcatca | gcagttgaga | ttaaattctc | agttaaggta | 780 |
| taaccactac | gtagtcgtca | actctaattt | aagagtaatg | gtagccaaga | catactatta | 840 |
| cctaatgtta | ttataatggg | attaccatcg | gttctgtatg | ataatggatt | acaataaatat | 900 |
| taccctgcag | agcctgattt | atttgaaact | aacagttcca | atatttctct | acgtctcgga | 960 |
| ctaaataaac | tttgattgtc | aaggttataa | agagatagaa | ataattatat | gccaagcaat | 1020 |
| cacggttttg | gatcaatagc | ttctttatta | atatacggtt | cgttagtgcc | aaaacctagt | 1080 |
| tatcgaatag | taacattctc | acctgaatat | tcttttagat | ttaatgataa | ttatcattgt | 1140 |
| aagagtggac | ttataagaaa | atctaaatta | ctattaagta | tgaatgaatt | tattcaagat | 1200 |
| cctgctctta | cattaatgca | ttcatactta | cttaaataag | ttctaggacg | agaatgtaat | 1260 |
| tacgtagaat | taatacattc | attacatgga | ctatatgggg | ctaaagggat | tcttaattat | 1320 |
| gtaagtaatg | tacctgatat | accccgattt | ccctaaacta | caaagtatac | tataacacaa | 1380 |
| aaacaaaatc | ccctaataac | atgatgtttc | atatgatatt | gtgttttttgt | tttaggggat | 1440 |
| tattgtaata | taagaggtac | aaatattgaa | gaattcttaa | cttttggagg | tttatattct | 1500 |
| ccatgtttat | aacttcttaa | gaattgaaaa | cctccaactg | atttaaacat | tattactagt | 1560 |
| gctcagtcca | atgatatcta | ttgactaaat | ttgtaataat | gatcacgagt | caggttacta | 1620 |
| tagataacta | atcttctagc | tgattataaa | aaaatagcgt | ctaaacttag | ctgattagaa | 1680 |
| gatcgactaa | tattttttta | tcgcagattt | gaatcgaaag | tacaagtatc | taatccacta | 1740 |
| cttaatcctt | ataaagatgt | ttttcatgtt | catagattag | gtgatgaatt | aggaatattt | 1800 |
| ctacaatttg | aagcaaagta | tggattagat | aaagatgcta | gcggaattta | taaacttcgt | 1860 |
| ttcataccta | atctatttct | acgatcgcct | taaatatcgg | taaatataaa | caaatttaat | 1920 |
| gatattttta | aaaaattata | cagccattta | tatttgttta | aattactata | aaaattttttt | 1980 |

```
aatatgagct ttacggaatt tgatttagca actaaatttc aagttaaatg ttcgaaatgc    2040
cttaaactaa atcgttgatt taaagttcaa tttacaaggc aaacttatat tggacagtat    2100
aaatacttca aactttcaaa ctccgtttga atataacctg tcatatttat gaagtttgaa    2160
agtttgttgt taaatgattc tatttataat atatcagaag gctataatat aaacaattta    2220
ctaagataaa tattatatag tcttccgata ttatataata atttaaaggt aaattttaga    2280
ggacagaatg caaatttaaa tttattaaat ttccatttaa aatctcctgt cttacgttta    2340
aatttaccta gaattattac accaattaca ggtagaggag aagtaaaaaa aggatcttaa    2400
taatgtggtt aatgtccatc tcctcttcat ttttttctcc ttagattttg taaaaatatt    2460
gtttctgtaa aaggcataag ggaggaatct aaaacatttt tataacaaag acattttccg    2520
tattccaagc ttcgcttcga agcg                                           2544
```

<210> SEQ ID NO 142
<211> LENGTH: 425
<212> TYPE: PRT
<213> ORGANISM: Artificial Sequence
<220> FEATURE:
<221> NAME/KEY: PEPTIDE
<222> LOCATION: (1)...(425)
<223> OTHER INFORMATION: Chimeric BoNT/E (NCLA/ExxxLL)

<400> SEQUENCE: 142

```
Pro Phe Val Asn Lys Gln Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255
```

```
Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Glu Val Lys Lys Leu Leu Arg Phe Cys Lys Asn Ile Val
                405                 410                 415

Ser Val Lys Gly Ile Arg Lys Leu Arg
            420                 425
```

<210> SEQ ID NO 143
<211> LENGTH: 2550
<212> TYPE: DNA
<213> ORGANISM: Artificial Sequence
<220> FEATURE:
<221> NAME/KEY: mat_peptide
<222> LOCATION: (1)...(2550)
<223> OTHER INFORMATION: Chimeric BoNT/E (NCLA/ExxxLL)

<400> SEQUENCE: 143

```
ccatttgtta ataaacagtt taattataat gatcctgtta atgatggtaa acaattattt      60
gtcaaattaa tattactagg acaattacta agaacaattt tatatattaa accaggcggt     120
tgtcaagaat tttattcttg ttaaaatata taatttggtc cgccaacagt tcttaaaata     180
aaatcattta atattatgaa aaatatttgg ataattccag agagatttag taaattataa     240
tactttttat aaacctatta aggtctctct aatgtaattg gtacaacccc ccaagatttt     300
catccgccta cttcattaca ttaaccatgt tggggggttc taaaagtagg cggatgaagt     360
ttaaaaaatg gagatagtag ttattatgac cctaattatt tacaaaattt tttacctcta     420
tcatcaataa tactgggatt aataaatgtt agtgatgaag aaaaggatag atttttaaaa     480
atagtcacaa aaatatcact acttcttttc ctatctaaaa atttttatca gtgtttttat     540
tttaatagaa taaataataa tctttcagga gggattttat tagaaaaatt atcttattta     600
ttattagaaa gtcctcccta aaataatctt gaactgtcaa aagctaatcc atatttaggg     660
aatgataata ctccacttga cagttttcga ttaggtataa atcccttact attatgaggt     720
gataatcaat tccatattgg tgatgcatca gcagttgaga ttaaactatt agttaaggta     780
taaccactac gtagtcgtca actctaattt ttctcaaatg gtagccaaga catactatta     840
cctaatgtta ttataaagag tttaccatcg gttctgtatg ataatggatt acaataatat     900
atgggagcag agcctgattt atttgaaact aacagttcca atatttaccc tcgtctcgga     960
ctaaataaac tttgattgtc aaggttataa tctctaagaa ataattatat gccaagcaat    1020
cacggttttg gatcaagaga ttctttatta atatacggtt cgttagtgcc aaaacctagt    1080
```

```
atagctatag taacattctc acctgaatat tcttttagat ttaattatcg atatcattgt   1140
aagagtggac ttataagaaa atctaaatta gataatagta tgaatgaatt tattcaagat   1200
cctgctctta cattactatt atcatactta cttaaataag ttctaggacg agaatgtaat   1260
atgcatgaat taatacattc attacatgga ctatatgggg ctaaatacgt acttaattat   1320
gtaagtaatg tacctgatat accccgattt gggattacta caaagtatac tataacacaa   1380
aaacaaaatc ccctacccta atgatgtttc atatgatatt gtgtttttgt tttaggggat   1440
ataacaaata taagaggtac aaatattgaa gaattcttaa cttttttattg tttatattct   1500 ccatgtttat aacttcttaa gaattgaaaa ggaggtactg atttaaacat tattactagt   1560
gctcagtcca atgatcctcc atgactaaat ttgtaataat gatcacgagt caggttacta   1620
atctatacta atcttctagc tgattataaa aaaatagcgt ctaaatagat atgattagaa   1680
gatcgactaa tattttttta tcgcagattt cttagcaaag tacaagtatc taatccacta   1740 cttaatccctt ataagaatc gtttcatgtt catagattag gtgatgaatt aggaatattt   1800
gatgtttttg aagcaaagta tggattagat aaagatgcta gcggactaca aaaacttcgt   1860
ttcataccta atctatttct acgatcgcct atttattcgg taaatataaa caaatttaat   1920
gatattttta aaaataaat aagccattta tatttgttta aattactata aaattttttt   1980
ttatacagct ttacggaatt tgatttagca actaaatttc aagttaatat gtcgaaatgc   2040
cttaaactaa atcgttgatt taaagttcaa aaatgtaggc aaacttatat tggacagtat   2100
aaatacttca aacttttttac atccgtttga atataacctg tcatatttat gaagtttgaa   2160
tcaaacttgt taaatgattc tatttataat atatcagaag gctatagttt gaacaattta   2220
ctaagataaa tattatatag tcttccgata aatataaata atttaaaggt aaattttaga   2280
ggacagaatg caaatttata tttattaaat ttccatttaa aatctcctgt cttacgttta   2340
ttaaatccta gaattattac accaattaca ggtagaggag aagtaaattt aggatcttaa   2400
taatgtggtt aatgtccatc tcctcttcat aaaaaactcc ttagattttg taaaaatatt   2460
gtttctgtaa aaggcttttt tgaggaatct aaaacatttt tataacaaag acattttccg   2520
ataaggaagc ttcgctattc cttcgaagcg                                   2550

<210> SEQ ID NO 144
<211> LENGTH: 6
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif
<221> NAME/KEY: VARIANT
<222> LOCATION: (2)...(4)
<223> OTHER INFORMATION: Xaa is any amino acid.

<400> SEQUENCE: 144

Glu Xaa Xaa Xaa Ile Ile
1               5

<210> SEQ ID NO 145
<211> LENGTH: 6
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif.
<221> NAME/KEY: VARIANT
<222> LOCATION: (2)...(4)
```

<223> OTHER INFORMATION: Xaa is any amino acid.

<400> SEQUENCE: 145

Glu Xaa Xaa Xaa Leu Leu
1               5

<210> SEQ ID NO 146
<211> LENGTH: 41
<212> TYPE: DNA
<213> ORGANISM: Artificial Sequence
<220> FEATURE:
<221> NAME/KEY: primer_bind
<222> LOCATION: (1)...(41)
<223> OTHER INFORMATION: N-ter LC/A forward oligonucleotide

<400> SEQUENCE: 146
accggatccc catttgttaa taaacagttt aattataatg a                 41

<210> SEQ ID NO 147
<211> LENGTH: 42
<212> TYPE: DNA
<213> ORGANISM: Artificial Sequence
<220> FEATURE:
<221> NAME/KEY: primer_bind
<222> LOCATION: (1)...(42)
<223> OTHER INFORMATION: N-ter LC/A reverse oligonucleotide

<400> SEQUENCE: 147
cgcgaagctt ccttatgcct tttacagaaa caatattttt ac                42

<210> SEQ ID NO 148
<211> LENGTH: 45
<212> TYPE: DNA
<213> ORGANISM: Artificial Sequence
<220> FEATURE:
<221> NAME/KEY: primer_bind
<222> LOCATION: (1)...(45)
<223> OTHER INFORMATION: LC/E PKI/PFV oligonucleotide

<400> SEQUENCE: 148
ccggttaccg gtaccggatc cccatttgtt aatagtttta attat            45

<210> SEQ ID NO 149
<211> LENGTH: 43
<212> TYPE: DNA
<213> ORGANISM: Artificial Sequence
<220> FEATURE:
<221> NAME/KEY: primer_bind
<222> LOCATION: (1)...(43)
<223> OTHER INFORMATION: LC/E PFVNS/PFVNK oligonucleotide

<400> SEQUENCE: 149
cggatcccca tttgttaata aatttaatta taatgatcct gtt              43

<210> SEQ ID NO 150
<211> LENGTH: 44
<212> TYPE: DNA
<213> ORGANISM: Artificial Sequence
<220> FEATURE:
<223> OTHER INFORMATION: LC/E insE oligonucleotide

<400> SEQUENCE: 150
gatccccatt tcttaataaa cagtttaatt ataatgatcc tgtt             44

<210> SEQ ID NO 151
<211> LENGTH: 44
<212> TYPE: PRT
<213> ORGANISM: Clostridial botulinum serotype A (Hall A)

<400> SEQUENCE: 151

Thr Asn Leu Ala Ala Asn Phe Asn Gly Gln Asn Thr Glu Ile Asn Asn
1               5                   10                  15

Met Asn Phe Thr Lys Leu Lys Asn Phe Thr Gly Leu Phe Glu Phe Tyr
            20                  25                  30

Lys Leu Leu Cys Val Arg Gly Ile Ile Thr Ser Lys
        35                  40

<210> SEQ ID NO 152
<211> LENGTH: 41
<212> TYPE: PRT
<213> ORGANISM: Clostridial botulinum serotype E (NTP genomic)

<400> SEQUENCE: 152

Asn Leu Lys Val Asn Phe Arg Gly Gln Asn Ala Asn Leu Asn Pro Arg
1               5                   10                  15

Ile Ile Lys Pro Ile Thr Gly Arg Gly Leu Val Lys Lys Ile Ile Arg
            20                  25                  30

Phe Cys Lys Asn Ile Val Ser Val Lys
        35                  40

<210> SEQ ID NO 153
<211> LENGTH: 41
<212> TYPE: PRT
<213> ORGANISM: Clostridial botulinum serotype E (Beluga)

<400> SEQUENCE: 153

Asn Leu Lys Val Asn Phe Arg Gly Asn Ala Asn Leu Asn Pro Arg Ile
1               5                   10                  15

Ile Thr Pro Ile Thr Gly Arg Gly Leu Val Lys Lys Ile Ile Arg Phe
            20                  25                  30

Cys Lys Asn Ile Val Ser Val Lys Gly
        35                  40

<210> SEQ ID NO 154
<211> LENGTH: 42
<212> TYPE: PRT
<213> ORGANISM: Clostridial botulinum serotype E (synth LC/E)

<400> SEQUENCE: 154

Asn Leu Lys Val Asn Phe Arg Gly Gln Asn Ala Asn Leu Asn Pro Arg
1               5                   10                  15

Ile Ile Thr Pro Ile Thr Gly Arg Gly Leu Val Lys Lys Ile Ile Arg
            20                  25                  30

Phe Cys Lys Asn Ile Val Ser Val Lys Gly
        35                  40

<210> SEQ ID NO 155
<211> LENGTH: 41
<212> TYPE: PRT
<213> ORGANISM: Clostridial botulinum serotype E (NCTC-11219)

<400> SEQUENCE: 155

Asn Leu Lys Val Asn Phe Arg Gly Asn Ala Asn Leu Asn Pro Arg Ile
1               5                   10                  15

Ile Thr Pro Ile Thr Gly Arg Gly Leu Val Lys Lys Ile Ile Arg Phe
            20                  25                  30

Cys Lys Asn Ile Val Ser Val Lys Gly
        35                  40

<210> SEQ ID NO 156
<211> LENGTH: 42
<212> TYPE: PRT
<213> ORGANISM: Clostridial botulinum serotype E (Dolly LC/E)

<400> SEQUENCE: 156

Asn Leu Lys Val Asn Phe Arg Gly Gln Asn Ala Asn Leu Asn Pro Arg
1               5                   10                  15

Ile Ile Thr Pro Ile Thr Gly Arg Gly Leu Val Lys Lys Ile Ile Arg
            20                  25                  30

Phe Cys Lys Asn Ile Val Ser Val Lys Gly
        35                  40

<210> SEQ ID NO 157
<211> LENGTH: 42
<212> TYPE: PRT
<213> ORGANISM: Artificial Sequence
<220> FEATURE:
<223> OTHER INFORMATION: Consensus sequence of C-terminal region of
      BoNT/A and BoNT/E light chains.

<400> SEQUENCE: 157

Asn Leu Lys Val Asn Phe Arg Gly Gln Asn Ala Asn Leu Asn Pro Arg
1               5                   10                  15

Ile Ile Thr Pro Ile Thr Gly Arg Gly Leu Val Lys Lys Ile Ile Arg
            20                  25                  30

Phe Cys Lys Asn Ile Val Ser Val Lys Gly
        35                  40

<210> SEQ ID NO 158
<211> LENGTH: 16
<212> TYPE: PRT
<213> ORGANISM: Clostridial botulinum serotype A

<400> SEQUENCE: 158

Met Pro Phe Val Asn Lys Gln Phe Asn Tyr Lys Asp Pro Val Asn Gly
1               5                   10                  15

<210> SEQ ID NO 159
<211> LENGTH: 11
<212> TYPE: PRT
<213> ORGANISM: Clostridial botulinum serotype A (DelN)

<400> SEQUENCE: 159

Met Tyr Lys Asp Pro Val Asn Gly Val Asp Ile
1               5                   10

<210> SEQ ID NO 160
<211> LENGTH: 16
<212> TYPE: PRT
<213> ORGANISM: Clostridial botulinum serotype B

<400> SEQUENCE: 160

Met Pro Val Thr Ile Asn Asn Phe Asn Tyr Asn Asp Pro Ile Asp Asn
1               5                   10                  15

<210> SEQ ID NO 161
<211> LENGTH: 16
<212> TYPE: PRT
<213> ORGANISM: Clostridial botulinum serotype E

<400> SEQUENCE: 161

Met Pro Lys Ile Asn Ser Phe Asn Tyr Asn Asp Pro Val Asn Asp Arg
1               5                   10                  15

```
<210> SEQ ID NO 162
<211> LENGTH: 16
<212> TYPE: PRT
<213> ORGANISM: Artificial Sequence
<220> FEATURE:
<223> OTHER INFORMATION: Consensus sequence of N-terminal region of
      BoNT/A, BoNT/B and BoNT/E light chains.

<400> SEQUENCE: 162

Met Pro Ile Asn Asn Phe Asn Tyr Asn Asp Pro Val Asn Gly Val Asp
1               5                   10                  15

<210> SEQ ID NO 163
<211> LENGTH: 6
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for Leucine-based motif of
      BoNT/E
<221> NAME/KEY: VARIANT
<222> LOCATION: (2)...(4)
<223> OTHER INFORMATION: Xaa is any amino acid

<400> SEQUENCE: 163

Leu Xaa Xaa Xaa Ile Ile
1               5
```

US 8,008,465 B2

NUCLEIC ACIDS ENCODING CHIMERA BOTULINUM TOXIN TYPE E

CROSS REFERENCE

This application is a divisional that claims priority pursuant to 35 U.S.C. §120 to U.S. patent application Ser. No. 11/036,532, filed Jan. 14, 2005 now U.S. Pat. No. 7,691,983, a continuation-in-part application which claims priority pursuant to 35 U.S.C. §120 to U.S. patent application Ser. No. 10/757,077, filed Jan. 14, 2004 now U.S. Pat. No. 7,491,799, a continuation-in-part of application which claims priority pursuant to 35 U.S.C. §120 to U.S. patent application Ser. No. 10/163,106, filed Jun. 4, 2002 now abandoned, a continuation-in-part of application which claims priority pursuant to 35 U.S.C. §120 to U.S. patent application Ser. No. 09/910,346, filed Jul. 20, 2001 now abandoned; a continuation-in-part of application which claims priority pursuant to 35 U.S.C. §120 to U.S. patent application Ser. No. 09/620,840, filed Jul. 21, 2000 now U.S. Pat. No. 6,903,187. All prior applications are incorporated herein by reference in their entireties.

BACKGROUND

The present invention relates to modified neurotoxins, particularly modified Clostridial neurotoxins, and use thereof to treat various conditions, including conditions that have been treated using naturally occurring botulinum toxins. For example, botulinum toxin type A has been used in the treatment of numerous conditions including pain, skeletal muscle conditions, smooth muscle conditions and glandular conditions. Botulinum toxins are also used for cosmetic purposes.

Numerous examples exist for treatment using botulinum toxin. For examples of treating pain see Aoki, et al., U.S. Pat. No. 6,113,915 and Aoki, et al., U.S. Pat. No. 5,721,215. For an example of treating a neuromuscular disorder, see U.S. Pat. No. 5,053,005, which suggests treating curvature of the juvenile spine, i.e., scoliosis, with an acetylcholine release inhibitor, preferably botulinum toxin A. For the treatment of strabismus with botulinum toxin type A, see Elston, J. S., et al., British Journal of Ophthalmology, 1985, 69, 718-724 and 891-896. For the treatment of blepharospasm with botulinum toxin type A, see Adenis, J. P., et al., J. Fr. Ophthalmol., 1990, 13 (5) at pages 259-264. For treating spasmodic and oromandibular dystonia torticollis, see Jankovic et al., Neurology, 1987, 37, 616-623. Spasmodic dysphonia has also been treated with botulinum toxin type A. See Blitzer et al., Ann. Otol. Rhino. Laryngol, 1985, 94, 591-594. Lingual dystonia was treated with botulinum toxin type A according to Brin et al., Adv. Neurol. (1987) 50, 599-608. Cohen et al., Neurology (1987) 37 (Suppl. 1), 123-4, discloses the treatment of writers cramp with botulinum toxin type A.

It would be beneficial to have botulinum toxins with enhanced biological persistence and/or enhanced biological activity.

SUMMARY

The present invention relates to a modified toxin comprising a modified light chain of a botulinum toxin type E, wherein the modified light chain comprises an amino acid sequence of SEQ ID NO: 120 (PFVNKQFN) at the N-terminus, and an amino acid sequence SEQ ID NO: 112 (xE-xxxLL) at the C-terminus, wherein x is any amino acid.

DEFINITIONS

Before proceeding to describe the present invention, the following definitions are provided and apply herein.

"Heavy chain" means the heavy chain of a Clostridial neurotoxin. It has a molecular weight of about 100 kDa and can be referred to herein as Heavy chain or as H.

"$H_N$" means a fragment (having a molecular weight of about 50 kDa) derived from the Heavy chain of a Clostridial neurotoxin which is approximately equivalent to the amino terminal segment of the Heavy chain, or the portion corresponding to that fragment in the intact Heavy chain. It is believed to contain the portion of the natural or wild-type Clostridial neurotoxin involved in the translocation of the light chain across an intracellular endosomal membrane.

"$H_C$" means a fragment (about 50 kDa) derived from the Heavy chain of a Clostridial neurotoxin which is approximately equivalent to the carboxyl terminal segment of the Heavy chain, or the portion corresponding to that fragment in the intact Heavy chain. It is believed to be immunogenic and to contain the portion of the natural or wild-type Clostridial neurotoxin involved in high affinity binding to various neurons (including motor neurons), and other types of target cells.

"Light chain" means the light chain of a Clostridial neurotoxin. It has a molecular weight of about 50 kDa, and can be referred to as light chain, L or as the proteolytic domain (amino acid sequence) of a Clostridial neurotoxin. The light chain is believed to be effective as an inhibitor of exocytosis, including as an inhibitor of neurotransmitter (i.e. acetylcholine) release when the light chain is present in the cytoplasm of a target cell.

"Neurotoxin" means a molecule that is capable of interfering with the functions of a cell, including a neuron. The "neurotoxin" can be naturally occurring or man-made. The interfered with function can be exocytosis.

"Modified neurotoxin" (or "modified toxin") means a neurotoxin which includes a structural modification. In other words, a "modified neurotoxin" is a neurotoxin which has been modified by a structural modification. The structural modification changes the biological persistence, such as the biological half-life (i.e. the duration of action of the neurotoxin) and/or the biological activity of the modified neurotoxin relative to the neurotoxin from which the modified neurotoxin is made or derived. The modified neurotoxin is structurally different from a naturally existing neurotoxin.

"Mutation" means a structural modification of a naturally occurring protein or nucleic acid sequence. For example, in the case of nucleic acid mutations, a mutation can be a deletion, addition or substitution of one or more nucleotides in the DNA sequence. In the case of a protein sequence mutation, the mutation can be a deletion, addition or substitution of one or more amino acids in a protein sequence. For example, a specific amino acid comprising a protein sequence can be substituted for another amino acid, for example, an amino acid selected from a group which includes the amino acids alanine, aspargine, cysteine, aspartic acid, glutamic acid, phenylalanine, glycine, histidine, isoleucine, lysine, leucine, methionine, proline, glutamine, arginine, serine, threonine, valine, tryptophan, tyrosine or any other natural or non-naturally occurring amino acid or chemically modified amino acids. Mutations to a protein sequence can be the result of mutations to DNA sequences that when transcribed, and the resulting mRNA translated, produce the mutated protein sequence. Mutations to a protein sequence can also be created by fusing a peptide sequence containing the desired mutation to a desired protein sequence.

"Structural modification" means any change to a neurotoxin that makes it physically or chemically different from an identical neurotoxin without the structural modification.

"Biological persistence" or "persistence" means the time duration of interference or influence caused by a neurotoxin or a modified neurotoxin with a cellular (such as a neuronal) function, including the temporal duration of an inhibition of exocytosis (such as exocytosis of neurotransmitter, for example, acetylcholine) from a cell, such as a neuron.

"Biological half-life" or "half-life" means the time that the concentration of a neurotoxin or a modified neurotoxin, preferably the active portion of the neurotoxin or modified neurotoxin, for example, the light chain of Clostridial toxins, is reduced to half of the original concentration in a mammalian cell, such as in a mammalian neuron.

"Biological activity" or "activity" means the amount of cellular exocytosis inhibited from a cell per unit of time, such as exocytosis of a neurotransmitter from a neuron.

"Target cell" means a cell (including a neuron) with a binding affinity for a neurotoxin or for a modified neurotoxin.

"PURE A" means a purified botulinum toxin type A, that is the 150 kDa toxin molecule.

BRIEF DESCRIPTION OF THE DRAWINGS

FIG. 1: Comparison of the N-terminal sequence of LC/A (Allergan Hall A), LC/B, and LC/E. dN-LC/A shows the amino acids truncated in our N-terminus deletion mutant. SEQ IDS NOs for the N-terminal sequences are as follows: rLC/A is SEQ ID NO: 158, dN-LC/A is SEQ ID NO: 159, LC/B is SEQ ID NO: 160, LC/E is SEQ ID NO: 161 and the consensus sequence is SEQ ID NO: 162.

FIG. 2: Sequence comparison of the C-terminus of the Allergan Hall A LC/A with the C-terminus of different strains of LC/E. The box contains the di-leucine motif present on the LC/A. The sequence in that area is very well conserved in all the LC/Es and contains two Isoleucines instead of the Leucines. SEQ IDS NOs for the C-terminal sequences are as follows: BoNT/A (Hall A) is SEQ ID NO: 151, LCE (NTP genomic) is SEQ ID NO: 152, BoNT/E (Beluga) is SEQ ID NO: 153, BoNT/E (synth LC/E) is SEQ ID NO: 154, BoNT/E (NCTC-11219) is SEQ ID NO: 155 and the consensus sequence is SEQ ID NO: 156.

Figure 14:
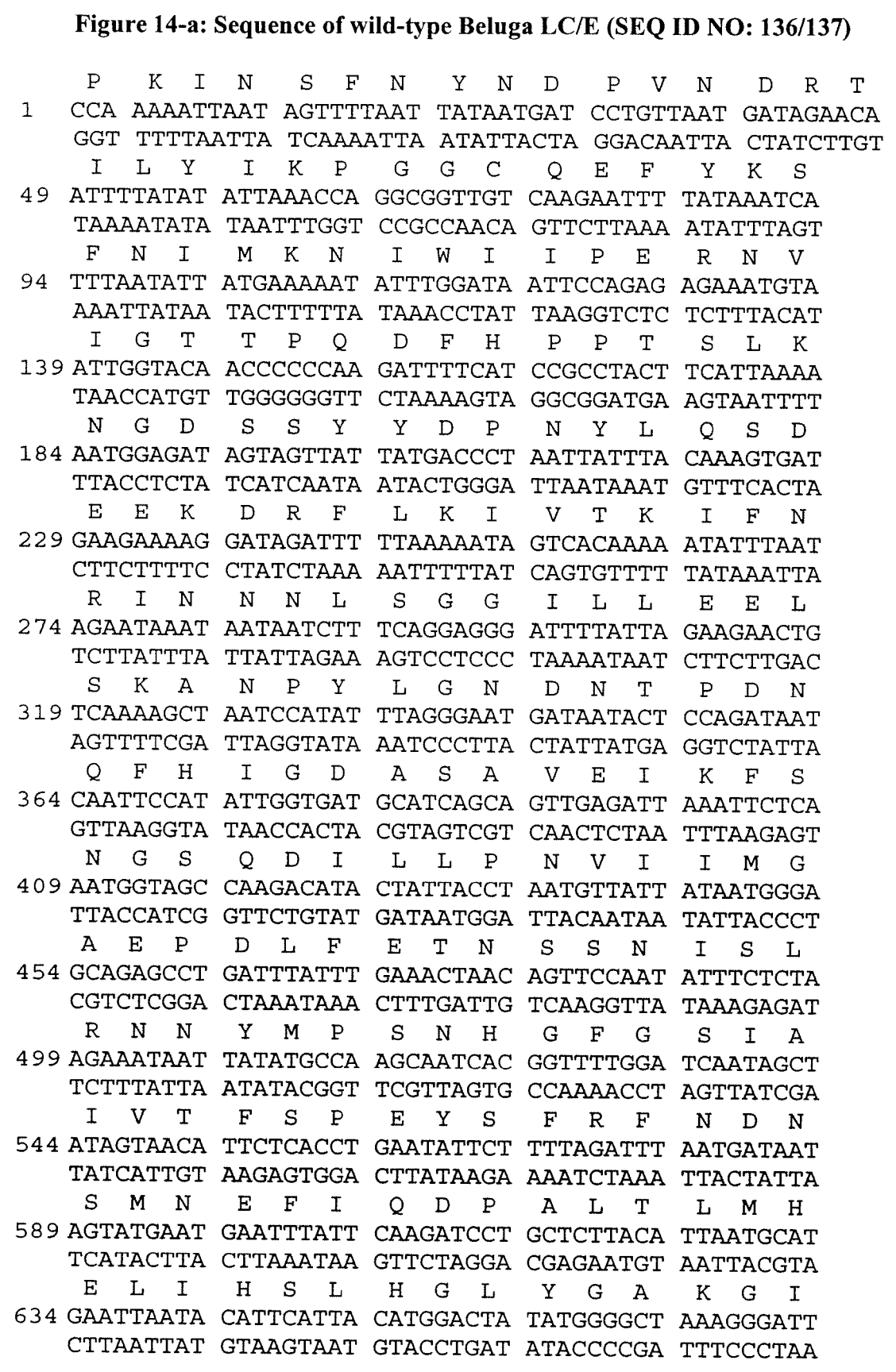

FIG. 14-a & b: Sequence of wild-type Beluga LC/E. SEQ ID NO: 136 and SEQ ID NO: 137 correspond to the amino acid sequence and the nucleic acid sequence, respectively.

FIG. 15-a & b: Sequence of chimera LC/E with N-terminus of LC/A. SEQ ID NO: 138 and SEQ ID NO: 139 correspond to the amino acid sequence and the nucleic acid sequence, respectively.

FIG. 16-a & b: Sequence of chimera LC/E with LC/A di-leucine motif at C-terminus. SEQ ID NO: 140 and SEQ ID NO: 141 correspond to the amino acid sequence and the nucleic acid sequence, respectively.

FIG. 17-a & b: Sequence of chimera LC/E with LC/A N-terminus and C-terminal di-leucine motif. SEQ ID NO: 142 and SEQ ID NO: 143 correspond to the amino acid sequence and the nucleic acid sequence, respectively.

DETAILED DESCRIPTION

Figure 3:
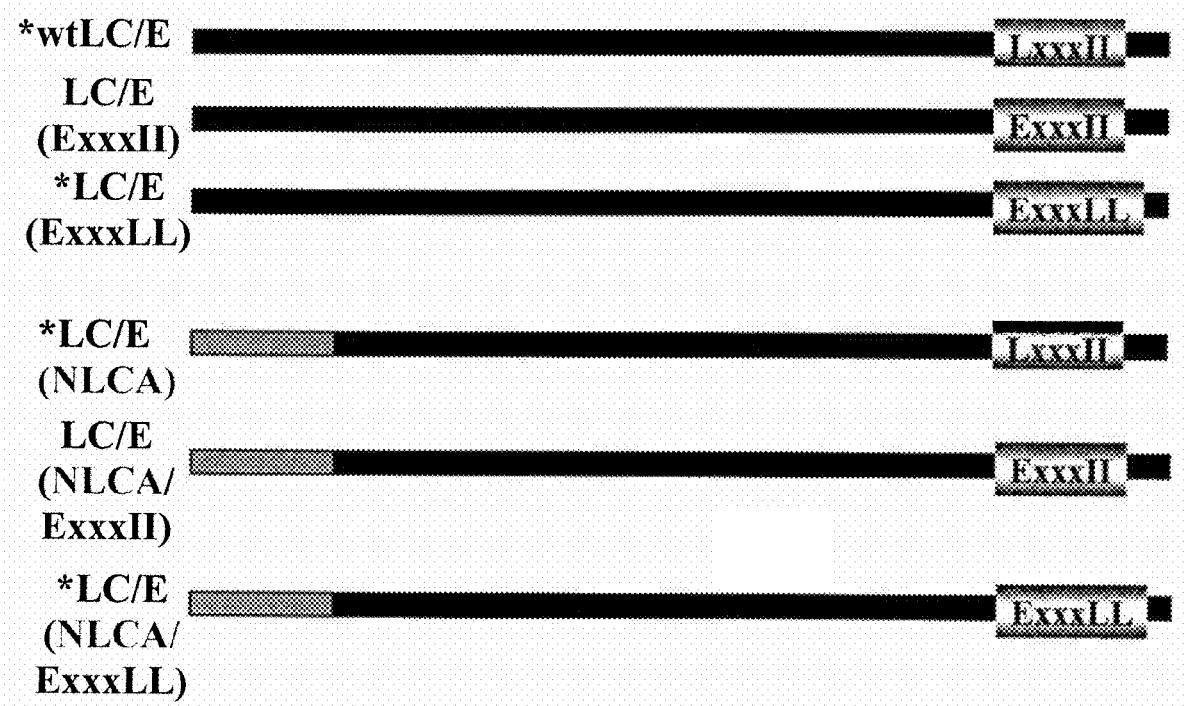
FIG. 3: LC/E chimeras generated by adding the localization signals of the LC/A into the LC/E. Constructs were generated by site-directed mutagenesis of the di-leucine motif SEQ ID NO: 163 at the C-terminus of the LC/E, and by the addition of SEQ ID NO: 120 from the LC/A to the N-terminus of the LC/E. wtLC/E includes the di-leucine motif of SEQ ID NO: 163; LC/E (ExxxII) includes the di-leucine motif of SEQ ID NO: 144; LC/E (ExxxLL) includes the di-leucine motif of SEQ ID NO: 145; LC/E (NLCA) includes SEQ ID NO: 120 and di-leucine motif of SEQ ID NO: 163; LC/E (NLCA/ExxxII) includes SEQ ID NO: 120 and di-leucine motif of SEQ ID NO: 144; and LC/E (NLCA/ExxxLL) includes SEQ ID NO: 120 and di-leucine motif of SEQ ID NO: 145.
Figure 4:
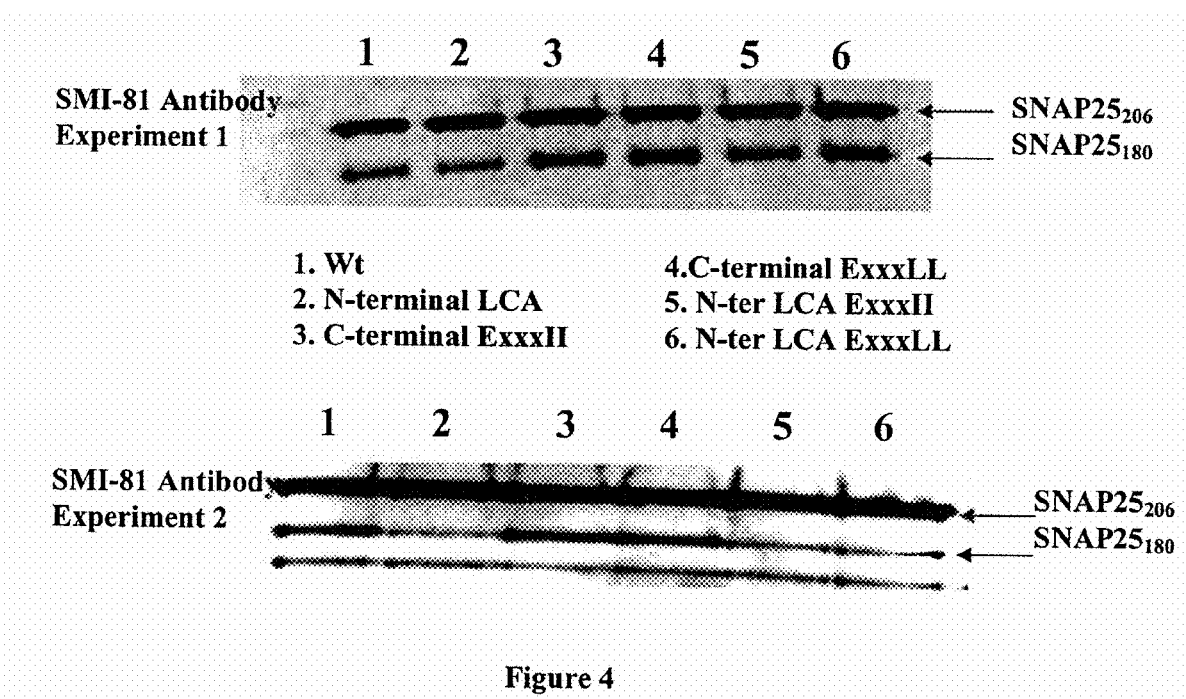
FIG. 4: Catalytic activity towards the cleavage of SNAP25 of the LC/E chimeras containing the localization signals from the LC/A and expressed in SH-SY5Y cells. Two separate transfections were performed and the western blot data from both experiments are shown in the figure. Blots were probed with antibody SMI-81 to the N-terminus of SNAP25.
Figure 5:
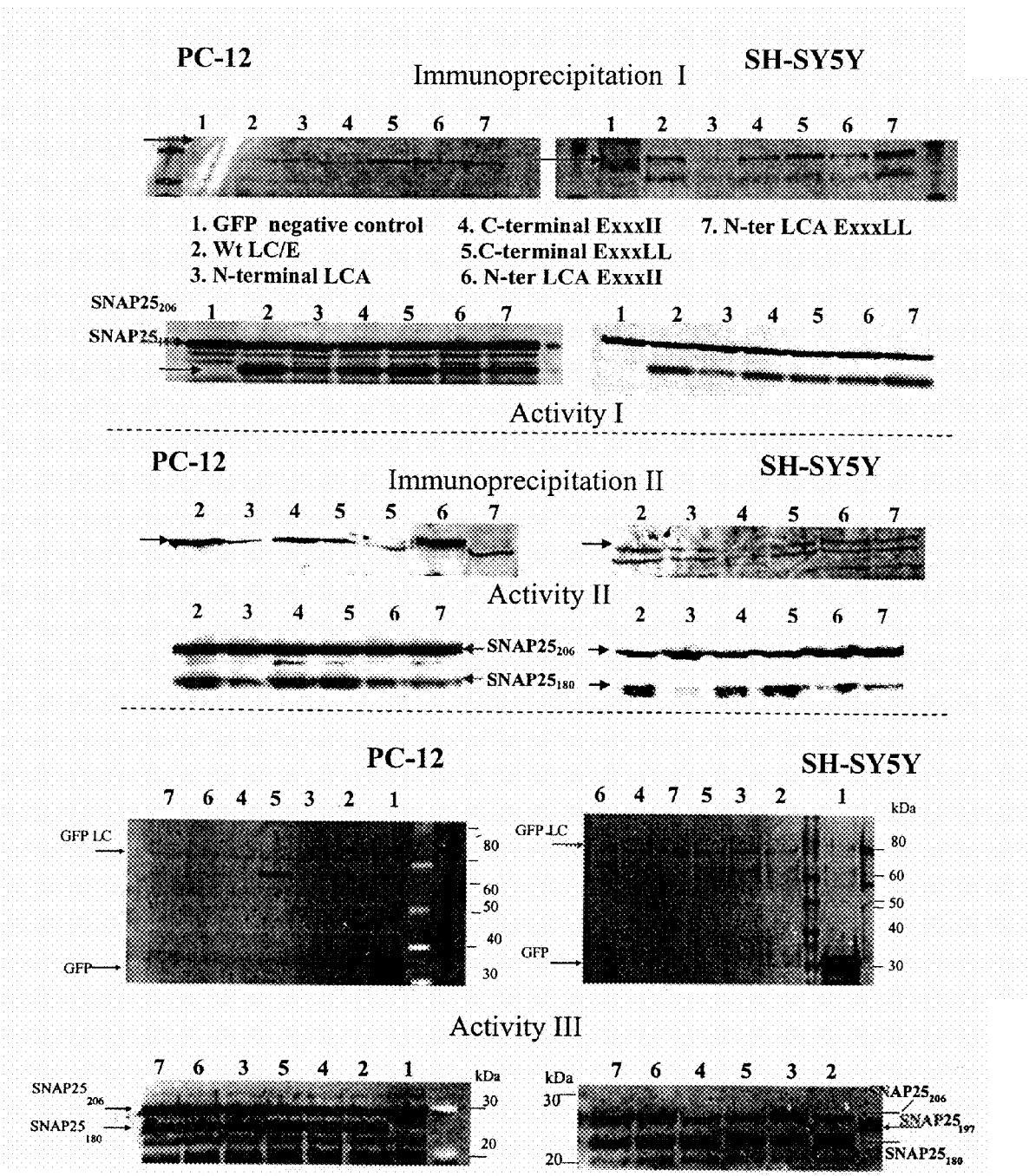
FIG. 5: Plasmids encoding for the GFP-LC/E chimeras were transfected into PC-12 and SH-SY5Y cells. Three separate experiments were performed. Experiment number one is the top panel, experiment number two is the middle panel, and experiment number three is the bottom panel. Cell lysates were prepared and subjected to immunoprecipitation (top gels in each panel) with an antibody to GFP to detect the expressed protein. Part of the lysate was used for western blots to detect catalytic activity (bottom gels in each panel) of the chimeras expressed in cells. Each lane is numbered according to the table shown in the first panel, and reads as follow: 1. GFP negative control, 2. Wt LC/E, 3. LC/E (NLCA) 4. LC/E (ExxxII) 5. LC/E (ExxxLL) 6. LC/E (NLCA/ExxxII) 7. LC/E (NLCA/ExxxLL).

The present invention is based upon the discovery that the biological persistence and/or the biological activity of a neurotoxin can be altered by structurally modifying the neurotoxin. In other words, a modified neurotoxin with an altered biological persistence and/or biological activity can be formed from a neurotoxin containing or including a structural modification. In some embodiments, the structural modification includes the fusing of a biological persistence enhancing component to the primary structure of a neurotoxin to enhance its biological persistence. In some embodiments, the biological persistence enhancing component is a leucine-based motif. Even more preferably, the biological half-life and/or the biological activity of the modified neurotoxin is enhanced by about 100%. Generally speaking, the modified neurotoxin has a biological persistence of about 20% to 300% more than an identical neurotoxin without the structural modification. That is, for example, the modified neurotoxin including the biological persistence enhancing component is able to cause a substantial inhibition of neurotransmitter release for example, acetylcholine from a nerve terminal for about 20% to about 300% longer than a neurotoxin that is not modified.

The present invention also includes within its scope a modified neurotoxin with a biological activity altered as compared to the biological activity of the native or unmodified neurotoxin. For example, the modified neurotoxin can exhibit a reduced or an enhanced inhibition of exocytosis (such as exocytosis of a neurotransmitter) from a target cell with or without any alteration in the biological persistence of the modified neurotoxin.

In a broad embodiment of the present invention, a leucine-based motif is a run of seven amino acids. The run is organized into two groups. The first five amino acids starting from the amino terminal of the leucine-based motif form a "quintet of amino acids." The two amino acids immediately following the quintet of amino acids form a "duplet of amino acids." In some embodiments, the duplet of amino acids is located at the carboxyl terminal region of the leucine-based motif. In some embodiments, the quintet of amino acids includes at least one acidic amino acid selected from a group consisting of a glutamate and an aspartate.

The duplet of amino acid includes at least one hydrophobic amino acid, for example leucine, isoleucine, methionine, alanine, phenylalanine, tryptophan, valine or tyrosine. Preferably, the duplet of amino acid is a leucine-leucine, a leucine-isoleucine, an isoleucine-leucine or an isoleucine-isoleucine, leucine-methionine. Even more preferably, the duplet is a leucine-leucine.

In some embodiments, the leucine-based motif is xDxxxLL, (SEQ ID NO:111) wherein x can be any amino acids. In some embodiments, the leucine-based motif is xExxxLL, (SEQ ID NO:112) wherein E is glutamic acid. In some embodiments, the duplet of amino acids can include an isoleucine or a methionine, forming xDxxxLI (SEQ ID NO:113) or xDxxxLM, (SEQ ID NO:114) respectively. Additionally, the aspartic acid, D, can be replaced by a glutamic acid, E, to form xExxxLI, (SEQ ID NO:115) xExxxIL (SEQ ID NO:116) and xExxxLM (SEQ ID NO:117). In some embodiments, the leucine-based motif is phenylalanine-glutamate-phenylalanine-tyrosine-lysine-leucine-leucine, SEQ ID NO:118.

In some embodiments, the quintet of amino acids comprises at least one hydroxyl containing amino acid, for example, a serine, a threonine or a tyrosine. Preferably, the hydroxyl containing amino acid can be phosphorylated. More preferably, the hydroxyl containing amino acid is a serine which can be phosphorylated to allow for the binding of adapter proteins.

Although non-modified amino acids are provided as examples, a modified amino acid is also contemplated to be within the scope of this invention. For example, leucine-based motif can include a halogenated, preferably, fluorinated leucine.

Various leucine-based motif are found in various species. A list of possible leucine-based motif derived from the various species that can be used in accordance with this invention is shown in Table 1. This list is not intended to be limiting.

TABLE 1

| Species | Sequence | SEQ ID NO: |
| --- | --- | --- |
| Botulinum type A | FEFYKLL | 1 |
| Rat VMAT1 | EEKRAIL | 2 |
| Rat VMAT 2 | EEKMAIL | 3 |
| Rat VAChT | SERDVLL | 4 |
| Rat δ | VDTQVLL | 5 |
| Mouse δ | AEVQALL | 6 |
| Frog γ/δ | SDKQNLL | 7 |
| Chicken γ/δ | SDRQNLI | 8 |
| Sheep δ | ADTQVLM | 9 |
| Human CD3γ | SDKQTLL | 10 |
| Human CD4 | SQIKRLL | 11 |
| Human δ | ADTQALL | 12 |
| *S. cerevisiae* Vam3p | NEQSPLL | 13 |

VMAT is vesicular monoamine transporter; VACht is vesicular acetylcholine transporter and *S. cerevisiae* Vam3p is a yeast homologue of synaptobrevin. Italicized serine residues are potential sites of phosphorylation.

The modified neurotoxin can be formed from any neurotoxin. Also, the modified neurotoxin can be formed from a fragment of a neurotoxin, for example, a botulinum toxin with a portion of the light chain and/or heavy chain removed. Preferably, the neurotoxin used is a Clostridial neurotoxin. A Clostridial neurotoxin comprises a polypeptide having three amino acid sequence regions. The first amino acid sequence region can include a target cell (i.e. a neuron) binding moiety which is substantially completely derived from a neurotoxin selected from a group consisting of baratti toxin; butyricum toxin; tetanus toxin; botulinum type A, B, $C_1$, D, E, F, and G. Preferably, the first amino acid sequence region is derived from the carboxyl terminal region of a toxin heavy chain, $H_C$. Also, the first amino acid sequence region can comprise a targeting moiety which can comprise a molecule (such as an amino acid sequence) that can bind to a receptor, such as a cell surface protein or other biological component on a target cell.

The second amino acid sequence region is effective to translocate the polypeptide or a part thereof across an endosome membrane into the cytoplasm of a neuron. In some embodiments, the second amino acid sequence region of the polypeptide comprises an amine terminal of a heavy chain, $H_N$, derived from a neurotoxin selected from a group consisting of baratti toxin; butyricum toxin; tetanus toxin; botulinum type A, B, $C_1$, D, E, F, and G.

The third amino acid sequence region has therapeutic activity when it is released into the cytoplasm of a target cell, such as a neuron. In some embodiments, the third amino acid sequence region of the polypeptide comprises a toxin light chain, L, derived from a neurotoxin selected from a group consisting of baratti toxin; butyricum toxin; tetanus toxin; botulinum type A, B, $C_1$, D, E, F, and G.

The Clostridial neurotoxin can be a hybrid neurotoxin. For example, each of the neurotoxin's amino acid sequence regions can be derived from a different Clostridial neurotoxin serotype. For example, in one embodiment, the polypeptide comprises a first amino acid sequence region derived from the H$_C$ of the tetanus toxin, a second amino acid sequence region derived from the H$_N$ of botulinum type B, and a third amino acid sequence region derived from the light chain of botulinum serotype E. All other possible combinations are included within the scope of the present invention.

Alternatively, all three of the amino acid sequence regions of the Clostridial neurotoxin can be from the same species and same serotype. If all three amino acid sequence regions of the neurotoxin are from the same Clostridial neurotoxin species and serotype, the neurotoxin will be referred to by the species and serotype name. For example, a neurotoxin polypeptide can have its first, second and third amino acid sequence regions derived from Botulinum type E. In which case, the neurotoxin is referred as Botulinum type E.

Additionally, each of the three amino acid sequence regions can be modified from the naturally occurring sequence from which they are derived. For example, the amino acid sequence region can have at least one or more amino acids added or deleted as compared to the naturally occurring sequence.

A biological persistence enhancing component or a biological activity enhancing component, for example a leucine-based motif, can be fused with any of the above described neurotoxins to form a modified neurotoxin with an enhanced biological persistence and/or an enhanced biological activity. "Fusing" as used in the context of this invention includes covalently adding to or covalently inserting in between a primary structure of a neurotoxin. For example, a biological persistence enhancing component and/or a biological activity enhancing component can be added to a Clostridial neurotoxin which does not have a leucine-based motif in its primary structure. In some embodiments, a leucine-based motif is fused with a hybrid neurotoxin, wherein the third amino acid sequence is derived from botulinum serotype A, B, C$_1$, C$_2$, D, E, F, or G. In some embodiments, the leucine-based motif is fused with a botulinum type E.

In some embodiments, a biological persistence enhancing component and/or a biological activity enhancing component is added to a neurotoxin by altering a cloned DNA sequence encoding the neurotoxin. For example, a DNA sequence encoding a biological persistence enhancing component and/or a biological activity enhancing component is added to a cloned DNA sequence encoding the neurotoxin into which the biological persistence enhancing component and/or a biological activity enhancing component is to be added. This can be done in a number of ways which are familiar to a molecular biologist of ordinary skill. For example, site directed mutagenesis or PCR cloning can be used to produce the desired change to the neurotoxin encoding DNA sequence. The DNA sequence can then be reintroduced into a native host strain. In the case of botulinum toxins the native host strain would be a *Clostridium botulinum* strain. Preferably, this host strain will be lacking the native botulinum toxin gene. In an alternative method, the altered DNA can be introduced into a heterologous host system such as *E. coli* or other prokaryotes, yeast, insect cell lines or mammalian cell lines. Once the altered DNA has been introduced into its host, the recombinant toxin containing the added biological persistence enhancing component and/or a biological activity enhancing component can be produced by, for example, standard fermentation methodologies.

Similarly, a biological persistence enhancing component can be removed from a neurotoxin. For example, site directed mutagenesis can be used to eliminate biological persistence enhancing components, for example, a leucine-based motif.

Standard molecular biology techniques that can be used to accomplish these and other genetic manipulations are found in Sambrook et al. (1989) which is incorporated in its entirety herein by reference.

In some embodiments, the leucine-based motif is fused with, or added to, the third amino acid sequence region of the neurotoxin. In some embodiments, the leucine-based motif is fused with, or added to, the region towards the carboxylic terminal of the third amino acid sequence region. More preferably, the leucine-based motif is fused with, or added to, the carboxylic terminal of the third region of a neurotoxin. Even more preferably, the leucine-based motif is fused with, or added to the carboxylic terminal of the third region of botulinum type E. The third amino acid sequence to which the leucine-based motif is fused or added can be a component of a hybrid or chimeric modified neurotoxin. For example, the leucine-based motif can be fused to or added to the third amino acid sequence region (or a part thereof) of one botulinum toxin type (i.e. a botulinum toxin type A), where the leucine-based motif-third amino acid sequence region has itself been fused to or conjugated to first and second amino acid sequence regions from another type (or types) of a botulinum toxin (such as botulinum toxin type B and/or E).

In some embodiments, a structural modification of a neurotoxin which has a pre-existing biological persistence enhancing component and/or a biological activity enhancing component, for example, a leucine-based motif includes deleting or substituting one or more amino acids of the leucine-based motif. In addition, a modified neurotoxin includes a structural modification which results in a neurotoxin with one or more amino acids deleted or substituted in the leucine-based motif. The removal or substitution of one or more amino acids from the preexisting leucine-based motif is effective to reduce the biological persistence and/or a biological activity of a modified neurotoxin. For example, the deletion or substitution of one or more amino acids of the leucine-based motif of botulinum type A reduces the biological half-life and/or the biological activity of the modified neurotoxin.

Amino acids that can be substituted for amino acids contained in a biological persistence enhancing component include alanine, asparagine, cysteine, aspartic acid, glutamic acid, phenylalanine, glycine, histidine, isoleucine, lysine, leucine, methionine, proline, glutamine, arginine, serine, threonine, valine, tryptophan, tyrosine and other naturally occurring amino acids as well as non-standard amino acids.

In the present invention the native botulinum type A light chain has been shown to localize to differentiated PC12 cell membranes in a characteristic pattern. Biological persistence enhancing components are shown to substantially contribute to this localization.

The data of the present invention demonstrates that when the botulinum toxin type A light chain is truncated or when the leucine-based motif is mutated, the light chain substantially loses its ability to localize to the membrane in its characteristic pattern. Localization to the cellular membrane is believed to be a key factor in determining the biological persistence and/or the biological activity of a botulinum toxin. This is because localization to a cell membrane can protect the localized protein from intracellular protein degradation.

The deletion of the leucine-based motif from the light chain of botulinum type A can change membrane localization of the type A light chain. GFP fusion proteins were produced and visualized in differentiated PC12 cells using methods well known to those skilled in the art, for example, as described in Galli et al (1998) Mol Biol Cell 9:1437-1448, incorporated in its entirety herein by reference; also, for example, as described in Martinez-Arca et al (2000) J Cell Biol 149:889-899, also incorporated in its entirety herein by reference.

Further studies have been done in the present invention to analyze the effect of specific amino acid substitutions within the leucine-based motif. For example, in one study both leucine residues contained in the leucine-based motif were substituted for alanine residues. The substitution of alanine for leucine at positions 427 and 428 in the botulinum type A light chain substantially changes the localization characteristic of the light chain.

It is within the scope of this invention that a leucine-based motif, or any other persistence enhancing component and/or a biological activity enhancing component present on a light chain, can be used to protect the heavy chain as well. A random coil belt extends from the botulinum type A translocation domain and encircles the light chain. It is possible that this belt keeps the two subunits in proximity to each other inside the cell while the light chain is localized to the cell membrane.

In addition, the data of the present invention shows that the leucine-based motif can be valuable in localizing the botulinum A toxin in close proximity to the SNAP-25 substrate within the cell. This can mean that the leucine-based motif is important not only for determining the half-life of the toxin but for determining the activity of the toxin as well. That is, the toxin will have a greater activity if it is maintained in close proximity to the SNAP-25 substrate inside the cell. Dong et al., PNAS, 101(41): 14701-14706, 2004.

The data of the present invention clearly shows that truncation of the light chain, thereby deleting the leucine-based motif, or amino acid substitution within the leucine-based motif substantially changes membrane localization of the botulinum type A light chain in nerve cells. In both truncation and substitution a percentage of the altered light chain can localize to the cell membrane in a pattern unlike that of the native type A light chain. This data supports the presence of biological persistence enhancing components other than a leucine-based motif such as tyrosine motifs and amino acid derivatives. Use of these other biological persistence enhancing components and/or a biological activity enhancing components in modified neurotoxins is also within the scope of the present invention.

Also within the scope of the present invention is more than one biological persistence enhancing component used in combination in a modified neurotoxin to alter biological persistence of the neurotoxin that is modified. The present invention also includes use of more than one biological activity enhancing or biological activity reducing components used in combination in a modified neurotoxin to alter the biological activity of the neurotoxin that is modified.

Tyrosine-based motifs are within the scope of the present invention as biological persistence and/or a biological activity altering components. Tyrosine-based motifs comprise the sequence Y-X-X-Hy (SEQ ID NO:119) where Y is tyrosine, X is any amino acid and Hy is a hydrophobic amino acid. Tyrosine-based motifs can act in a manner that is similar to that of leucine-based motifs.

Also within the scope of the present invention are modified neurotoxins which comprise one or more biological persistence altering components and/or a biological activity enhancing components which occur naturally in both botulinum toxin types A and B.

Amino acid derivatives are also within the scope of the present invention as biological persistence enhancing components and/or as biological activity enhancing components. Examples of amino acid derivatives that act to effect biological persistence and/or biological activity are phosphorylated amino acids. These amino acids include, for example, amino acids phosphorylated by tyrosine kinase, protein kinase C or casein kinase II. Other amino acid derivatives within the scope of the present invention as biological persistence enhancing components and/or as biological activity enhancing components are myristylated amino acids and N-glycosylated amino acids.

The present invention also contemplates compositions which include a botulinum light chain component interacting with a cellular structure component, for example, an intracellular structure component. The structure component may include lipid, carbohydrate, protein or nucleic acid or any combination thereof.

The structure component may include a cell membrane, for example, a plasma membrane. In certain embodiments, the structure component comprises all or part of one or more organelles, for example, the nucleus, endoplasmic reticulum, golgi apparatus, mitochondria, lysosomes or secretory vesicles or combinations thereof. The structure component may include any portion of an organelle, for example, the membrane of an organelle. The structure component may also include any substance which is included in the cytoplasm of a cell.

The structure component may include one or more proteins. In some embodiments, the structure component includes one or more cellular proteins. One or more of these cellular proteins may be membrane associated proteins, for example, plasma membrane associated proteins. In some embodiments of the invention, the structure component includes adaptor proteins. Examples of adaptor proteins are AP-1, AP-2 and AP-3. Adaptor proteins and their characteristics are well known in the art and are discussed in, for example, Darsow et al., J. Cell Bio., 142, 913 (1998) which is incorporated in its entirety herein by reference. The one or more proteins may also include the substrate which is cleaved by the proteolytic domain of a botulinum toxin light chain component. For example, a protein included in the structure component may be SNAP-25.

The interaction between the light chain of botulinum type A and the structure component may contribute to localization of the toxin in a certain pattern. Therefore, the interaction may act to facilitate proteolysis by, for example, increasing the biological persistence and/or biological activity of the light chain.

A botulinum toxin heavy chain or portion thereof may also be associated with the light chain component when the light chain is interacting with the structure component.

In some embodiments, a botulinum toxin light chain component, when interacting with the structure component in a cell, may localize in the cell in a particular pattern. For example, localization of a botulinum toxin type A light chain component may be in a unctuate or spotted pattern. For example, a botulinum type A light chain component may be localized in a unctuate pattern on a cell membrane, for example, a plasma membrane. Botulinum type B light chain may localize in the cytoplasm. Botulinum type E may localize to the plasma membrane but to a lesser degree than type A. Botulinum type E may also localize in the cytoplasm.

Methodologies to produce an isolated composition of the invention are available to those skilled in the art. For example, a composition may be isolated by isolating the plasma membrane from a cell after introduction of a light chain component, for example, light chain A, into a cell. The light chain may be introduced into the cell by, for example, electroporation or by endocytosis. In the case of introduction into the cell by endocytosis, a heavy chain component may be included with the light chain component to facilitate the endocytosis, for example, receptor mediated endocytosis, of the light chain. In such preparation process, the heavy chain component may also be isolated and be included in the composition.

After introduction into the cell, the light chain component associates or interacts with the substrate component forming a composition. The composition may be isolated by purification of the light chain component-structure component from the cell. Standard purification techniques known to those skilled in the art may be used to isolate a membrane and/or membrane associated protein(s) which is included in the structure component which interacts with the light chain component. Examples of conventional techniques for isolation and purification of the light chain component/structure component include immunoprecipitation and/or membrane purification techniques.

The light chain component may be crosslinked to a portion of the structure component before isolation. The technical procedures for cross linking of biomolecules using agents such as DTBP are well known to those skilled in the art.

In some embodiments, a composition of the invention may be prepared by mixing together a purified or a partially purified light chain component and a purified or a partially purified intracellular structure component under conditions which are effective to form the composition. Conditions important in forming the composition may include Ph, ionic concentration and temperature.

The botulinum toxin light chain component of a composition, may be a modified botulinum toxin light chain. Modifications may be mutations and/or deletions as described elsewhere herein.

A modified light chain component may include a light chain A modified to remove a leucine based motif or other structure(s) which contributes to localization of the type A light chain to the plasma membrane thereby resulting in a light chain with a reduced ability to localize to a plasma membrane. This may result in a reduction in the biological activity and/or biological persistence of the light chain A. The biological persistence and/or activity of the modified light chain may be about 10% to about 90% that of an unmodified type A light chain.

Another modified light chain component may include a light chain A modified by adding one or more leucine based motifs, or other structure(s) which contributes to localization of the type A light chain to the plasma membrane, thereby resulting in a light chain with an increased ability to localize to a plasma membrane. This may result in an increase in the biological activity and/or biological persistence of the light chain A. The biological persistence and/or activity of the modified light chain may be about 1.5 to about 5 times that of an unmodified type A light chain.

A modified light chain component may include a light chain E modified by adding one or more leucine based motifs, or other structure(s) which contribute to localization of the type A light chain to the plasma membrane, thereby resulting in a light chain with an increased ability to localize to a plasma membrane. This may result in an increase in the biological activity and/or biological persistence of the light chain E. The biological persistence and/or activity of the modified light chain may be about 2 to about 20 times that of an unmodified type E light chain.

Compositions of the invention have many uses and applications, for example, in research science and medicine. Other uses and applications will be readily apparent to those skilled in the art.

In one broad aspect of the present invention, a method is provided for treating a condition using a modified neurotoxin. The conditions can include, for example, skeletal muscle conditions, smooth muscle conditions, pain and glandular conditions. The modified neurotoxin can also be used for cosmetics, for example, to treat brow furrows.

The neuromuscular disorders and conditions that can be treated with a modified neurotoxin include: for example, spasmodic dysphonia, laryngeal dystonia, oromandibular and lingual dystonia, cervical dystonia, focal hand dystonia, blepharospasm, strabismus, hemifacial spasm, eyelid disorders, spasmodic torticolis, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups can be treated using the present methods of administration. Other examples of conditions that can be treated using the present methods and compositions are lacrimation, hyperhydrosis, excessive salivation and excessive gastrointestinal secretions, as well as other secretory disorders. In addition, the present invention can be used to treat dermatological conditions, for example, reduction of brow furrows, reduction of skin wrinkles. The present invention can also be used in the treatment of sports injuries.

Borodic U.S. Pat. No. 5,053,005 discloses methods for treating juvenile spinal curvature, i.e. scoliosis, using botulinum type A. The disclosure of Borodic is incorporated in its entirety herein by reference. In some embodiments, using substantially similar methods as disclosed by Borodic, a modified neurotoxin can be administered to a mammal, preferably a human, to treat spinal curvature. In some embodiments, a modified neurotoxin comprising botulinum type E fused with a leucine-based motif is administered. Even more preferably, a modified neurotoxin comprising botulinum type A-E with a leucine-based motif fused to the carboxyl terminal of its light chain is administered to the mammal, preferably a human, to treat spinal curvature.

In addition, the modified neurotoxin can be administered to treat other neuromuscular disorders using well known techniques that are commonly performed with botulinum type A. For example, the present invention can be used to treat pain, for example, headache pain, pain from muscle spasms and various forms of inflammatory pain. For example, Aoki U.S. Pat. No. 5,721,215 and Aoki U.S. Pat. No. 6,113,915 disclose methods of using botulinum toxin type A for treating pain. The disclosure of these two patents is incorporated in its entirety herein by reference.

Autonomic nervous system disorders can also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. disclose methods for treating the autonomic nervous system; for example, treating autonomic nervous system disorders such as excessive sweating, excessive salivation, asthma, etc., using naturally existing botulinum toxins. The disclosure of Sander et al. is incorporated in its entirety by reference herein. In some embodiments, substantially similar methods to that of Sanders et al. can be employed, but using a modified neurotoxin, to treat autonomic nervous system disorders such as the ones discussed above. For example, a modified neurotoxin can be locally applied to the nasal cavity of the mammal in an amount sufficient to degenerate cholinergic neurons of the autonomic nervous system that control the mucous secretion in the nasal cavity.

Pain that can be treated by a modified neurotoxin includes pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy can be treated with a naturally occurring botulinum toxin, for example Botulinum type A. The disclosures of Binder are incorporated in its entirety herein by reference. In some embodiments, substantially similar methods to that of Binder can be employed, but using a modified neurotoxin, to treat headache, especially the ones caused by vascular disturbances, muscular tension, neuralgia and neuropathy. Pain caused by muscle spasm can also be treated by an administration of a modified neurotoxin. For example, a botulinum type E fused with a leucine-based motif, preferably at the carboxyl terminal of the botulinum type E light chain, can be administered intramuscularly at the pain/spasm location to alleviate pain.

Furthermore, a modified neurotoxin can be administered to a mammal to treat pain that is not associated with a muscular disorder, such as spasm. In one broad embodiment, methods of the present invention to treat non-spasm related pain include central administration or peripheral administration of the modified neurotoxin.

For example, Foster et al. in U.S. Pat. No. 5,989,545 discloses that a botulinum toxin conjugated with a targeting moiety can be administered centrally (intrathecally) to alleviate pain. The disclosures of Foster et al. are incorporated in its entirety by reference herein. In some embodiments, substantially similar methods to that of Foster et al. can be employed, but using the modified neurotoxin according to this invention, to treat pain. The pain to be treated can be an acute pain, or preferably, chronic pain.

An acute or chronic pain that is not associated with a muscle spasm can also be alleviated with a local, peripheral administration of the modified neurotoxin to an actual or a perceived pain location on the mammal. In some embodiments, the modified neurotoxin is administered subcutaneously at or near the location of pain, for example, at or near a cut. In some embodiments, the modified neurotoxin is administered intramuscularly at or near the location of pain, for example, at or near a bruise location on the mammal. In some embodiments, the modified neurotoxin is injected directly into a joint of a mammal, for treating or alleviating pain caused by arthritic conditions. Also, frequent repeated injection or infusion of the modified neurotoxin to a peripheral pain location is within the scope of the present invention. However, given the long lasting therapeutic effects of the present invention, frequent injection or infusion of the neurotoxin can not be necessary. For example, practice of the present invention can provide an analgesic effect, per injection, for 2 months or longer, for example 27 months, in humans.

Without wishing to limit the invention to any mechanism or theory of operation, it is believed that when the modified neurotoxin is administered locally to a peripheral location, it inhibits the release of Neuro-substances, for example substance P, from the peripheral primary sensory terminal by inhibiting SNARE-dependent exocytosis. Since the release of substance P by the peripheral primary sensory terminal can cause or at least amplify pain transmission process, inhibition of its release at the peripheral primary sensory terminal will dampen the transmission of pain signals from reaching the brain.

The amount of the modified neurotoxin administered can vary widely according to the particular disorder being treated, its severity and other various patient variables including size, weight, age, and responsiveness to therapy. Generally, the dose of modified neurotoxin to be administered will vary with the age, presenting condition and weight of the mammal, preferably a human, to be treated. The potency of the modified neurotoxin will also be considered.

Assuming a potency (for a botulinum toxin type A) which is substantially equivalent to $LD_{50}$=2,730 U in a human patient and an average person is 75 kg, a lethal dose (for a botulinum toxin type A) would be about 36 U/kg of a modified neurotoxin. Therefore, when a modified neurotoxin with such an $LD_{50}$ is administered, it would be appropriate to administer less than 36 U/kg of the modified neurotoxin into human subjects. Preferably, about 0.01 U/kg to 30 U/kg of the modified neurotoxin is administered. More preferably, about 1 U/kg to about 15 U/kg of the modified neurotoxin is administered. Even more preferably, about 5 U/kg to about 10 U/kg modified neurotoxin is administered. Generally, the modified neurotoxin will be administered as a composition at a dosage that is proportionally equivalent to about 2.5 cc/100 U. Those of ordinary skill in the art will know, or can readily ascertain, how to adjust these dosages for neurotoxin of greater or lesser potency. It is known that botulinum toxin type B can be administered at a level about fifty times higher that that used for a botulinum toxin type A for similar therapeutic effect. Thus, the units amounts set forth above can be multiplied by a factor of about fifty for a botulinum toxin type B.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., $14^{th}$ edition, published by McGraw Hill). For example, the route and dosage for administration of a modified neurotoxin according to the present disclosed invention can be selected based upon criteria such as the solubility characteristics of the modified neurotoxin chosen as well as the types of disorder being treated.

The modified neurotoxin can be produced by chemically linking the leucine-based motif to a neurotoxin using conventional chemical methods well known in the art. For example, botulinum type E can be obtained by establishing and growing cultures of *Clostridium botulinum* in a fermenter, and then harvesting and purifying the fermented mixture in accordance with known procedures.

The modified neurotoxin can also be produced by recombinant techniques. Recombinant techniques are preferable for producing a neurotoxin having amino acid sequence regions from different Clostridial species or having modified amino acid sequence regions. Also, the recombinant technique is preferable in producing botulinum type A with the leucine-based motif being modified by deletion. The technique includes steps of obtaining genetic materials from natural sources, or synthetic sources, which have codes for a cellular binding moiety, an amino acid sequence effective to translocate the neurotoxin or a part thereof, and an amino acid sequence having therapeutic activity when released into a cytoplasm of a target cell, preferably a neuron. In some embodiments, the genetic materials have codes for the biological persistence enhancing component, preferably the leucine-based motif, the $H_C$, the $H_N$ and the light chain of the Clostridial neurotoxins and fragments thereof. The genetic constructs are incorporated into host cells for amplification by first fusing the genetic constructs with a cloning vectors, such as phages or plasmids. Then the cloning vectors are inserted into a host, for example, *Clostridium* sp., *E. coli* or other prokaryotes, yeast, insect cell line or mammalian cell lines. Following the expressions of the recombinant genes in host cells, the resultant proteins can be isolated using conventional techniques.

There are many advantages to producing these modified neurotoxins recombinantly. For example, to form a modified neurotoxin, a modifying fragment, or component must be attached or inserted into a neurotoxin. The production of neurotoxin from anaerobic *Clostridium* cultures is a cumbersome and time-consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL-3). During the fermentation process, the folded single-chain neurotoxins are activated by endogenous Clostridial proteases through a process termed nicking to create a dichain. Sometimes, the process of nicking involves the removal of approximately 10 amino acid residues from the single-chain to create the dichain form in which the two chains remain covalently linked through the intrachain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the serotype and amounts of proteolytic activity produced by a given strain. For example, greater than 99% of *Clostridial botulinum* serotype A single-chain neurotoxin is activated by the Hall A *Clostridial botulinum* strain, whereas serotype B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered Clostridial toxins is, therefore, an important consideration for manufacture of these materials. It would be a major advantage if neurotoxins such as botulinum toxin and tetanus toxin could be expressed, recombinantly, in high yield in rapidly-growing bacteria (such as heterologous *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and light chains of tetanus and botulinum toxins; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and light chains can be combined by oxidative disulphide linkage to form the neuroparalytic di-chains.

EXAMPLES

The following non-limiting examples provide those of ordinary skill in the art with specific suitable methods to treat non-spasm related pain within the scope of the present invention and are not intended to limit the scope of the invention.

Example 1

Treatment of Pain Associated with Muscle Disorder

An unfortunate 36 year old woman has a 15 year history of temporomandibular joint disease and chronic pain along the masseter and temporalis muscles. Fifteen years prior to evaluation she noted increased immobility of the jaw associated with pain and jaw opening and closing and tenderness along each side of her face. The left side is originally thought to be worse than the right. She is diagnosed as having temporomandibular joint (TMJ) dysfunction with subluxation of the joint and is treated with surgical orthoplasty meniscusectomy and condyle resection.

She continues to have difficulty with opening and closing her jaw after the surgical procedures and for this reason, several years later, a surgical procedure to replace prosthetic joints on both sides is performed. After the surgical procedure progressive spasms and deviation of the jaw ensues. Further surgical revision is performed subsequent to the original operation to correct prosthetic joint loosening. The jaw continues to exhibit considerable pain and immobility after these surgical procedures. The TMJ remained tender as well as the muscle itself. There are tender points over the temporomandibular joint as well as increased tone in the entire muscle. She is diagnosed as having post-surgical myofascial pain syndrome and is injected with the modified neurotoxin into the masseter and temporalis muscles; the modified neurotoxin is botulinum type E comprising a leucine-based motif. The particular dose as well as the frequency of administrations depends upon a variety of factors within the skill of the treating physician.

Several days after the injections she noted substantial improvement in her pain and reports that her jaw feels looser. This gradually improves over a 2 to 3 week period in which she notes increased ability to open the jaw and diminishing pain. The patient states that the pain is better than at any time in the last 4 years. The improved condition persists for up to 27 months after the original injection of the modified neurotoxin.

Example 2

Treatment of Pain Subsequent to Spinal Cord Injury

A patient, age 39, experiencing pain subsequent to spinal cord injury is treated by intrathecal administration, for example, by spinal tap or by catherization (for infusion) to the spinal cord, with the modified neurotoxin; the modified neurotoxin is botulinum type E comprising a leucine-based motif. The particular toxin dose and site of injection, as well as the frequency of toxin administrations, depend upon a variety of factors within the skill of the treating physician, as previously set forth. Within about 1 to about 7 days after the modified neurotoxin administration, the patient's pain is substantially reduced. The pain alleviation persists for up to 27 months.

Example 3

Peripheral Administration of a Modified Neurotoxin to Treat "Shoulder-Hand Syndrome"

Pain in the shoulder, arm, and hand can develop, with muscular dystrophy, osteoporosis and fixation of joints. While most common after coronary insufficiency, this syndrome can occur with cervical osteoarthritis or localized shoulder disease, or after any prolonged illness that requires the patient to remain in bed.

A 46 year old woman presents a shoulder-hand syndrome type pain. The pain is particularly localized at the deltoid region. The patient is treated by a bolus injection of a modified neurotoxin subcutaneously to the shoulder; preferably the modified neurotoxin is botulinum type E comprising a leucine-based motif. The modified neurotoxin can also be, for example, modified botulinum type A, B, C1, C2, D, E, F or G which comprise a leucine-based motif. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 4

Peripheral Administration of a Modified Neurotoxin to Treat Postherapeutic Neuralgia Postherapeutic neuralgia is one of the most intractable of chronic pain problems. Patients suffering this excruciatingly painful process often are elderly, have debilitating disease, and are not suitable for major interventional procedures. The diagnosis is readily made by the appearance of the healed lesions of herpes and by the patient's history. The pain is intense and emotionally distressing. Postherapeutic neuralgia can occur anywhere, but is most often in the thorax.

A 76 year old man presents a postherapeutic type pain. The pain is localized to the abdomen region. The patient is treated by a bolus injection of a modified neurotoxin intradermally to the abdomen; the modified neurotoxin is, for example, botulinum type A, B, C1, C2, D, E, F and/or G. The modified neurotoxin comprises a leucine-based motif and/or additional tyrosine-based motifs. The particular dose as well as the frequency of administration depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 5

Peripheral Administration of a Modified Neurotoxin to Treat Nasopharyngeal Tumor Pain These tumors, most often squamous cell carcinomas, are usually in the fossa of Rosenmuller and can invade the base of the skull. Pain in the face is common. It is constant, dull-aching in nature.

A 35 year old man presents a nasopharyngeal tumor type pain. Pain is found at the lower left cheek. The patient is treated by a bolus injection of a modified neurotoxin intramuscularly to the cheek, preferably the modified neurotoxin is botulinum type A, B, C1, C2, D, E, F or G comprising additional biological persistence enhancing amino acid derivatives, for example, tyrosine phosphorylations. The particular dose as well as the frequency of administrations depends upon a variety of factors within the skill of the treating physician. Within 1-7 days after modified neurotoxin administration the patient's pain is substantially alleviated. The duration of the pain alleviation is from about 7 to about 27 months.

Example 6

Peripheral Administration of a Modified Neurotoxin to Treat Inflammatory Pain A patient, age 45, presents an inflammatory pain in the chest region. The patient is treated by a bolus injection of a modified neurotoxin intramuscularly to the chest, preferably the modified neurotoxin is botulinum type A, B, C1, C2, D, E, F or G comprising additional tyrosine-based motifs. The particular dose as well as the frequency of administrations depends upon a variety of factors within the skill of the treating physician, as previously set forth. Within 1-7 days after modified neurotoxin administration the patient's pain is substantially alleviated. The duration of the pain alleviation is from about 7 to about 27 months.

Example 7

Treatment of Excessive Sweating

A male, age 65, with excessive unilateral sweating is treated by administering a modified neurotoxin. The dose and frequency of administration depends upon degree of desired effect. Preferably, the modified neurotoxin is botulinum type A, B, C1, C2, D, E, F and/or G. The modified neurotoxins comprise a leucine-based motif. The administration is to the gland nerve plexus, ganglion, spinal cord or central nervous system. The specific site of administration is to be determined by the physician's knowledge of the anatomy and physiology of the target glands and secretory cells. In addition, the appropriate spinal cord level or brain area can be injected with the toxin. The cessation of excessive sweating after the modified neurotoxin treatment is up to 27 months.

Example 8

Post Surgical Treatments

A female, age 22, presents a torn shoulder tendon and undergoes orthopedic surgery to repair the tendon. After the surgery, the patient is administered intramuscularly with a modified neurotoxin to the shoulder. The modified neurotoxin can botulinum type A, B, C, D, E, F, and/or G wherein one or more amino acids of a biological persistence enhancing component are deleted from the toxin. For example, one or more leucine residues can be deleted from and/or mutated from the leucine-based motif in botulinum toxin serotype A. Alternatively, one or more amino acids of the leucine-based motif can be substituted for other amino acids. For example, the two leucines in the leucine-based motif can be substituted for alanines. The particular dose as well as the frequency of administrations depends upon a variety of factors within the skill of the treating physician. The specific site of administration is to be determined by the physician's knowledge of the anatomy and physiology of the muscles. The administered modified neurotoxin reduces movement of the arm to facilitate the recovery from the surgery. The effect of the modified neurotoxin is for about five weeks or less.

Example 9

Cloning, Expression and Purification of the Botulinum Neurotoxin Light Chain Gene This example describes methods to clone and express a DNA nucleotide sequence encoding a botulinum toxin light chain and purify the resulting protein product. A DNA sequence encoding the botulinum toxin light chain can be amplified by PCR protocols which employ synthetic oligonucleotides having sequences corresponding to the 5' and 3' end regions of the light chain gene. Design of the primers can allow for the introduction of restriction sites, for example, Stu I and EcoR I restriction sites into the 5' and 3' ends of the botulinum toxin light chain gene PCR product. These restriction sites can be subsequently used to facilitate unidirectional subcloning of the amplification products. Additionally, these primers can introduce a stop codon at the C-terminus of the light chain coding sequence. Chromosomal DNA from *C. botulinum*, for example, strain HaIIA, can serve as a template in the amplification reaction.

The PCR amplification can be performed in a 0.1 mL volume containing 10 mM Tris-HCl (pH 8.3), 50 mM KCl, 1.5 mM MgCl2, 0.2 mM of each deoxynucleotide triphosphate (dNTP), 50 pmol of each primer, 200 ng of genomic DNA and 2.5 units of Taq DNA polymerase. The reaction mixture can be subjected to 35 cycles of denaturation (1 minute at 94° C.), annealing (2 minutes at 55° C.) and polymerization (2 minutes at 72° C.). Finally, the reaction can be extended for an additional 5 minutes at 72° C.

The PCR amplification product can be digested with for example, Stu I and EcoR I, to release the light chain encoding, cloned, PCR DNA fragment. This fragment can then be purified by, for example, agarose gel electrophoresis, and ligated into, for example, a Sma I and EcoR I digested pBluescript II SK phagemid. Bacterial transformants, for example, *E. coli*, harboring this recombinant phagemid can be identified by standard procedures, such as blue/white screening. Clones comprising the light chain encoding DNA can be identified by DNA sequence analysis performed by standard methods. The cloned sequences can be confirmed by comparing the cloned sequences to published sequences for botulinum light chains, for example, Binz, et al., in *J. Biol. Chem.* 265, 9153 (1990), Thompson et al., in *Eur. J. Biochem.* 189, 73 (1990) and Minton, Clostridial Neurotoxins, The Molecular Pathogenesis of Tetanus and Botulism p. 161-191, Edited by C. Motecucco (1995).

The light chain can be subcloned into an expression vector, for example, pMal-P2. pMal-P2 harbors the malE gene encoding MBP (maltose binding protein) which is controlled by a strongly inducible promoter, $P_{tac}$.

To verify expression of the botulinum toxin light chain, a well isolated bacterial colony harboring the light chain gene containing pMal-P2 can be used to inoculate L-broth containing 0.1 mg/ml ampicillin and 2% (w/v) glucose, and grown overnight with shaking at 30° C. The overnight cultures can be diluted 1:10 into fresh L-broth containing 0.1 mg/ml of ampicillin and incubated for 2 hours. Fusion protein expression can be induced by addition of IPTG to a final concentration of 0.1 mM. After an additional 4 hour incubation at 30° C., bacteria can be collected by centrifugation at 6,000×g for 10 minutes.

A small-scale SDS-PAGE analysis can confirm the presence of a 90 kDa protein band in samples derived from IPTG-induced bacteria. This MW would be consistent with the predicted size of a fusion protein having MBP (~40 kDa) and botulinum toxin light chain (~50 kDa) components.

The presence of the desired fusion proteins in IPTG-induced bacterial extracts can be confirmed by western blotting using the polyclonal anti-L chain probe described by Cenci di Bello et al., in *Eur. J. Biochem.* 219, 161 (1993). Reactive bands on PVDF membranes (Pharmacia; Milton Keynes, UK) can be visualized using an anti-rabbit immunoglobulin conjugated to horseradish peroxidase (BioRad; Hemel Hempstead, UK) and the ECL detection system (Amersham, UK). Western blotting results typically confirm the presence of the dominant fusion protein together with several faint bands corresponding to proteins of lower MW than the fully sized fusion protein. This observation suggests that limited degradation of the fusion protein occurred in the bacteria or during the isolation procedure.

To produce the subcloned light chain, pellets from 1 liter cultures of bacteria expressing the wild-type Botulinum neurotoxin light chain proteins can be resuspended in column buffer [10 mM Tris-HCl (pH 8.0), 200 mM NaCl, 1 mM EGTA and 1 mM DTT] containing 1 mM phenylmethanesulfonyl fluoride (PMSF) and 10 mM benzamidine, and lysed by sonication. The lysates can be cleared by centrifugation at 15,000×g for 15 minutes at 4° C. Supernatants can be applied to an amylose affinity column [2×10 cm, 30 ml resin] (New England BioLabs; Hitchin, UK). Unbound proteins can be washed from the resin with column buffer until the eluate is free of protein as judged by a stable absorbance reading at 280 nm. The bound MBP-L chain fusion protein can be subsequently eluted with column buffer containing 10 mM maltose. Fractions containing the fusion protein can be pooled and dialyzed against 20 mM Tris-HCl (pH 8.0) supplemented with 150 mM NaCl, 2 mM, CaCl2 and 1 mM DTT for 72 hours at 4° C.

The MBP-L chain fusion proteins can be purified after release from the host bacteria. Release from the bacteria can be accomplished by enzymatically degrading or mechanically disrupting the bacterial cell membrane. Amylose affinity chromatography can be used for purification. Recombinant wild-type or mutant light chains can be separated from the sugar binding domains of the fusion proteins by site-specific cleavage with Factor Xa. This cleavage procedure typically yields free MBP, free light chains and a small amount of uncleaved fusion protein. While the resulting light chains present in such mixtures can be shown to possess the desired activities, an additional purification step can be employed. For example, the mixture of cleavage products can be applied to a second amylose affinity column which binds both the MBP and uncleaved fusion protein. Free light chains can be isolated in the flow through fraction.

Example 10

Reconstitution of Native Light Chain, Recombinant Wild-Type Light Chain with Purified Heavy Chain Native heavy and light chains can be dissociated from a BoNT with 2 M urea, reduced with 100 mM DTT and then purified according to established chromatographic procedures. For example, Kozaki et al. (1981, *Japan J. Med. Sci. Biol.* 34, 61) and Maisey et al. (1988, *Eur. J. Biochem.* 177, 683). A purified heavy chain can be combined with an equimolar amount of either native light chain or a recombinant light chain. Reconstitution can be carried out by dialyzing the samples against a buffer consisting of 25 mM Tris (pH 8.0), 50 µM zinc acetate and 150 mM NaCl over 4 days at 4° C. Following dialysis, the association of the recombinant light chain and native heavy chain to form disulfide linked 150 kDa dichains is monitored by SDS-PAGE and/or quantified by densitometric scanning.

Example 11

Production of a Modified Neurotoxin with an Enhanced Biological Persistence

A modified neurotoxin can be produced by employing recombinant techniques in conjunction with conventional chemical techniques.

A neurotoxin chain, for example a botulinum light chain that is to be fused with a biological persistence enhancing component to form a modified neurotoxin can be produced recombinantly and purified as described in example 9.

The recombinant neurotoxin chain derived from the recombinant techniques can be covalently fused with (or coupled to) a biological persistence enhancing component, for example a leucine-based motif, a tyrosine-based motif and/or an amino acid derivative. Peptide sequences comprising biological persistence enhancing components can be synthesized by standard t-Boc/Fmoc technologies in solution or solid phase as is known to those skilled in the art. Similar synthesis techniques are also covered by the scope of this invention, for example, methodologies employed in Milton et al. (1992, *Biochemistry* 31, 8799-8809) and Swain et al.

The modified neurotoxins produced according to this example have an enhanced biological persistence. Preferably, the biological persistence is enhanced by about 20% to about 300% relative to an identical neurotoxin without the additional biological persistence enhancing component(s).

Example 12

The first 30 residues of the amino-terminus (N-term) and the last 50 residues of the carboxyl-terminal (C-term) of the amino acid sequences of botulinum toxin serotypes A through G light chains (LC) are shown in Table 2.

TABLE 2

| Toxin | N-term (AAs 1-30) of LC | SEQ ID NO: | C-term (last 50 AAs) of LC | SEQ ID NO: |
|---|---|---|---|---|
| BoNT/A | MPFVNKQFNYKDPVNGVDIAY IKIPNAGQM | 14 | GFNLRNTNLAANFNGQNTEIN NMNFTKLKNFTGLFEFYKLLC VRGIITSK | 15 |
| BoNT/B | MPVTINNFNYNDPIDNDNIIM MEPPFARGT | 16 | YTIEEGFNISDKNMGKEYRGQ NKAINKQAYEEISKEHLAVYK IQMCKSVK | 17 |
| BoNT/C₁ | MPITINNFNYSDPVDNKNILY LDTHLNTLA | 18 | NIPKSNLNVLFMGQNLSRNPA LRKVNPENMLYLFTKFCHKAI DGRSLYNK | 19 |
| BoNT/D | MTWPVKDFNYSDPVNDNDILY LRIPQNKLI | 20 | YTIRDGFNLTNKGFNIENSGQ NIERNPALQKLSSESVVDLFT KVCLRLTK | 21 |
| BoNT/E | MPKINSFNYNDPVNDRTILYI KPGGCQEFY | 22 | GYNINNLKVNFRGQNANLNPR IITPITGRGLVKKIIRFCKNI VSVKGIRK | 23 |
| BoNT/F | MPVAINSFNYNDPVNDDTILY MQIPYEEKS | 24 | TVSEGFNIGNLAVNNRGQSIK LNPKIIDSIPDKGLVEKIVKF CKSVIPRK | 25 |
| BoNT/G | MPVNIKNFNYNDPINNDDIIM MEPFNDPGP | 26 | QNEGFNIASKNLKTEFNGQNK AVNKEAYEEISLEHLVIYRIA MCKPVMYK | 27 |

(1993, *Peptide Research* 6, 147-154). One or more synthesized biological persistence enhancing components can be fused to the light chain of botulinum type A, B, C1, C2, D, E, F or G at, for example, the carboxyl terminal end of the toxin. The fusion of the biological persistence enhancing components is achieved by chemical coupling using reagents and techniques known to those skilled in the art, for example PDPH/EDAC and Traut's reagent chemistry.

Alternatively, a modified neurotoxin can be produced recombinantly without the step of fusing the biological persistence enhancing component to a recombinant botulinum toxin chain. For example, a recombinant neurotoxin chain, for example, a botulinum light chain, derived from the recombinant techniques of example 9 can be produced with a biological persistence enhancing component, for example a leucine-based motif, a tyrosine-based motif and/or an amino acid derivative. For example, one or more DNA sequences encoding biological persistence enhancing components can be added to the DNA sequence encoding the light chain of botulinum type A, B, C1, C2, D, E, F or G. This addition can be done by any number of methods used for site directed mutagenesis which are familiar to those skilled in the art.

The recombinant modified light chain containing the fused or added biological persistence enhancing component can be reconstituted with a heavy chain of a neurotoxin by the method described in example 10 whereby producing a complete modified neurotoxin.

Alterations in the amino acid sequence of these serotypes can include amino acid substitutions, mutations, deletions, or various combinations of these alterations. Such alterations can be engineered in the first thirty amino acids (AAs) in the N-terminus of the light chain and/or the last fifty AAs in the C-terminus of the light chain using recombinant DNA technological methods that are standard in the art.

For example, studies showed that a GFP-LCA construct with eight amino acid residues (PFVNKQFN) (SEQ ID NO:120) deleted from the N-terminus (no C-terminus deletion) localized in PC12 cells a very similar pattern to the localization in PC12 cells of a truncated GFP-LCA construct with both the C and N terminus deletions.

Further studies showed that a GFP-LCA construct with twenty two amino acid residues (KNFTG LFEFYKLLCV RGIITSK) (SEQ ID NO:121) deleted from the C-terminus (no N-terminus deletion) localized in PC12 cells in a very similar manner to that of the GFP-LCA(LL-->AA) mutant.

A GFP-LCA construct with both eight amino acid residues (PFVNKQFN; SEQ ID NO: 120) deleted from the N-terminus and twenty two amino acid residues (KNFTG LFEFYKLLCV RGIITSK; SEQ ID NO: 121) deleted from the C-terminus accumulated intracellularly.

Examples of amino acid sequence substitutions include the replacement of one or more contiguous or non-contiguous amino acids in the first 30 amino acids of the N-terminus and/or the last 50 amino acids of the C-terminus of the light chain with an equal number and placement of amino acids that differ from the wild-type sequence. Substitutions can be conservative or non-conservative of the character of the amino acid. For example, the amino acid valine at a specific position in the wild-type sequence can be replaced with an alanine in the same position in the substituted sequence. Furthermore, basic residues such as arginine or lysine can be substituted for highly hydrophobic residues such as tryptophan. A proline or histidine residue may be substituted in order to form or disrupt a potentially important structural or catalytic element of the protein. Some examples of amino acid substitutions are indicated by bold underlined text in the sequences described in Table 3.

Examples of amino acid sequence mutations include changes in the first 30 amino acids of the N-terminus and/or the last 50 amino acids of the C-terminus of the light chain sequence such that one or several amino acids are added, substituted and/or deleted such that the identity, number and position of amino acids in the wild-type light chain sequence is not necessarily conserved in the mutated light chain sequence. Some examples of amino acid sequence mutations are described in Table 4, in which additions of amino acids are shown in bold underlined text, and deletions are indicated by dashes in the sequences shown.

TABLE 3

| Toxin | N-term (AAs 1-30) of LC | SEQ ID NO: | C-term (last 50 AAs) of LC | SEQ ID NO: |
|---|---|---|---|---|
| BoNT/A | MPFANKQFNYKDPVNGVDIAYIKIPNAGQM | 28 | GFNLRNTNLAANFNGQNTEINNMNRTKLKNFTGLFEFYKLLCVRGIITSK | 29 |
| BoNT/A | MPFVNKQFNKKDPVNGVDIAYIKIPNAGQM | 30 | GFNLRNTNLAANFNGQNTEINNMNFTKLKNAAGLFEFYKLLCVRGIITSK | 31 |
| BoNT/A | MPFVNKQFNYKDPVNGVDIARIKIPNAGQM | 32 | GFNLRNTNLAANHNGQNTEINNMNFTKLKNFTGLFEFYKLLCVRGIITSK | 33 |
| BoNT/A | MPFVNKHFNYKDPVNGVDIAYIKIPNAGQM | 34 | GFNLRNTNLAANFNGQNTEINNMNFTKLKNFTGLFEFYKLLCARGIITSK | 35 |
| BoNT/B | MPATINNFNYNDPIDNDNIIMMEPPFARGT | 36 | YTIEEGFNISDKNMGKEYRGQNKAINKQAYEEISKEHLAVYKIRMCKSVK | 37 |
| BoNT/B | MPVTINNFNYNDPIDNDNIIAAEPPFARGT | 38 | YTIEEGFNISDKNMGKEYRGQNKAINKQAYEEISKEHLAVRKIQMCKSVK | 39 |
| BoNT/B | MPVTINNFNRNDPIDNDNIIMMEPPFARGT | 40 | YTIEEGFNISDKNMGKEYRGQNKAINKQAKEEISKEHLAVYKIQMCKSVK | 41 |
| BoNT/C₁ | MPITINNKNYSDPVDNKNILYLDTHLNTLA | 42 | NIPKSNLNVLFMGQNLSRNPALRKVNPENMLYLFTKFCHKAIDGRSLRNK | 43 |
| BoNT/D | MTWPAKDFNYSDPANDNDILYLRIPQNKLI | 44 | YTIRDGFNLTNKGFNIENSGQNIERNPALQKLSSESVVDLFTKACLRLTK | 45 |
| BoNT/E | MPKINSFNYNDPANDRTILYIKPGGCQEFY | 46 | GYNINNLKVNFRGQNANLNPRIITPITGRGHVKKIIRFCKNIVSVKGIRK | 47 |
| BoNT/E | MPKINSRNYNDPVNDRTILYIKPGGCQEFY | 48 | GYNINNLKVNFRGQNANLNPRIITPITGRGLVKKIIRFCKNAASVKGIRK | 49 |
| BoNT/E | MPKINSFNYNDPVNDRTILYIKPGGCQEFR | 50 | GYNINNLKVNFRGQNANLNPRIITPITGRGLVKKIIRFCKNIVSAKGIRK | 51 |
| BoNT/F | MPAAINSFNYNDPVNDDTILYMQIPYEEKS | 52 | TVSEGFNIGNLAVNNRGQSIKLNPKIIDSIPDKGLVEKIVKFCKSAIPRK | 53 |
| BoNT/G | MPVNIKNHNYNDPINNDDIIMMEPFNDPGP | 54 | QNEGFNIASKNLKTEFNGQNKAVNKEAYEEISLEHLVIYRIAMCKPAMYK | 55 |

TABLE 4

| Toxin | N-term (AAs 1-30) of LC | SEQ ID NO: | C-term (last 50 AAs) of LC | SEQ ID NO: |
|---|---|---|---|---|
| BoNT/A | MPFVNKQFNYKDPVNGVDIAYIKIPH---- | 56 | GFNLRNTNLAANFNGQNTEINNMNAAAAAAAAAA-------CVRGIITSK | 57 |
| BoNT/A | MAAA----NYKDPVNGVDIAYIKIPNAGQM | 58 | GKNLRNTNLAANFNGQNTEINNMNFTKLKNFTGLFEFYK-CVRGIITSK | 59 |
| BoNT/A | MPFVNKQFNYKDPVNGVDIAR----NAGQM | 60 | GFNLRNTNLAA----HNTEINNMNFTKLKNFTGLFEFYKLLCVRGIITSK | 61 |
| BoNT/A | MPKVNKQFN----VNGVDIAYIKIPNAGQM | 62 | GFNLRNTNLAANFNGQNTEINNMNFTKLKNFTGLFEFRR--------TSK | 63 |
| BoNT/B | MPVTINNFNYNDPIDNDNIIAAAAAAARGT | 64 | YTIPPGFNISDKNMGKEYRGQNKAINKQAYEEISKEH------------- | 65 |
| BoNT/B | MPA----FNYNDPIDNDNIIMMEPPFARST | 66 | YTIEEGFNISDKNMGKEYRGQNKAAAAAAAAEEISKEHLAVYKIQMCKSVK | 67 |
| BoNT/B | MPVTINNFNR----------MMEPPFARST | 68 | YTIEESFNISDKNMSKEYRSQNKAINKQAY------AAAAAAIQMCKSVK | 69 |
| BoNT/C₁ | M---------SDPVDNKNILYLDTHLNTLA | 70 | NIPKSNLNVLFMSQNLSRNPALRKVNPENMLAAA---CHKAIDSRSLYNK | 71 |
| BoNT/D | MTRPVKD----DPVNDNDILYLRIPQNKLI | 72 | YTIRDSFNLTNKSFNIENSSQNIERNPALQKL------DLPPKVCLRLTK | 73 |
| BoNT/E | MPKINSPPNYNDPVNDRTILYIKPGGCQEFY | 74 | GYNINNLKVNFRSQNANLNPRIITPITSRSLVKKAAAACKNIVSVKSIRK | 75 |
| BoNT/E | MPKINSFNYNDPAAAANDRTILYIKPSSCQEFY | 76 | GYNINNLKVNFRSQNANLNPRIITPITSRSLV---HRFCKNIVSVKSIRK | 77 |
| BoNT/E | MPKINSFNYNDPVNDRTILKIKPGGCKEFY | 78 | GYNINNLKVNFRSQNANLNPRIITPITGRGLPP----------------- | 79 |
| BoNT/F | MP------NYNDPVNDDTILYMQIPYEEKS | 80 | TVSEGFNIGNLAVNNRGQSIKLNPKIIDSIPDKGAAAAAA--CKSVIPRK | 81 |
| BoNT/G | MPVNIPP----DPINNDDIIMMEPFNDPGP | 82 | QNEGFNIASKNLKTEFNGQNKAVNKEAY--------------AAAAAAA | 83 |

Examples of amino acid sequence deletions include the removal of one or more contiguous or non-contiguous amino acids from the first 30 amino acids of the N-terminus and/or the last 50 amino acids of the C-terminus of the light chain sequence. Some examples of amino acid sequence deletions are indicated by dashes in the sequences shown in Table 5.

TABLE 5

| Toxin | N-term (AAs 1-30) of LC | SEQ ID NO: | C-term (last 50 AAs) of LC | SEQ ID NO: |
|---|---|---|---|---|
| BoNT/A | M--------YKDPVNGVDIAYIKIPNAGQM | 84 | GFNLRNTNLAANFNGQNTEINNMNFTKLKNFTGLFEFYK----------- | 85 |
| BoNT/A | MPFVNKQ------VNGVDIAYIKIPNAGQM | 86 | GFNLRNTNLAANFNGQNTEINNMNFTKLK---------LLCVRGIITSK | 87 |
| BoNT/A | MPFVNKQFNYKDP------AYIKIPNAGQM | 88 | GFNLRNTNLAANFNGQNTEINNMN--------------GLFEFYKLLCVRGIITSK | 89 |

TABLE 5-continued

| Toxin | N-term (AAs 1-30) of LC | SEQ ID NO: | C-term (last 50 AAs) of LC | SEQ ID NO: |
|---|---|---|---|---|
| BoNT/A | MPFVNKQFNYKDPVNGVDIA---------- | 90 | GFNLRN----------NTEINNMNFTKLKNFTGLFEFYKLLCVRGIITSK | 91 |
| BoNT/B | MPVTINNFNYNDPIDNDNIIMME------- | 92 | YTI-----ISDKNMGKEYRGQNKAINKQAYEEISKEHLAVYKIQMCKSVK | 93 |
| BoNT/B | MPVTINNFNYND----------EPPFARGT | 94 | YTIEEGFNISD--------GQNKAINKQAYEEISKEHLAVYKIQMCKSVK | 95 |
| BoNT/B | MP--------NDPIDNDNIIMMEPPFARGT | 96 | YTIEEGFNISDKNMGKEYRGQNKAINKQA-------------KIQMCKSVK | 97 |
| BoNT/C₁ | MPI-------SDPVDNKNILYLDTHLNTLA | 98 | NIPKSNLNVLFMGQNLSRNPALRKV----------KFCHKAIDGRSLYNK | 99 |
| BoNT/D | MTW----------VNDNDILYLRIPQNKLI | 100 | YTIRDGFNLTNKGFNIENSGQNIERNPA----------DLFTKVCLRLTK | 101 |
| BoNT/E | MP--------DPVNDRTILYIKPGGCQEFY | 102 | GYNINNLKVNFRGQNANLNPRIITPI----------RFCKNIVSVKGIRK | 103 |
| BoNT/E | MPKINSFNYN----------IKPGGCQEFY | 104 | GYNINN------GQNANLNPRIITPITGRGLVKKIIRFCKNIVSVKGIRK | 105 |
| BoNT/E | MPKINSFNYNDPVNDRTILYIK-------- | 106 | GYNINNLKVNFRGQNANLNPRIITPITGRGLVKKIIR--------KGIRK | 107 |
| BoNT/F | MPVAINSFNYNDPVNDDTILYMQIP----- | 108 | TVSEGFNIGNLAVNNRGQSIKLNPKIIDSIPD--------KFCKSVIPRK | 109 |
| BoNT/G | M--------------------------- | — | QNEGFNIASKNLKTEFNGQNKAVNKEA------------RIAMCKPVMYK | 110 |

Example 13

In some embodiments of the present invention, the biological persistence and/or the enzymatic activity of a toxin can be altered by structurally modifying the toxin. In some embodiments, the structural modification includes the substitution, mutation or deletion of amino acids within the toxin. In some embodiments, the structural modification includes a chimeric fusion construct in which a biological persistence-enhancing component or an enzymatic activity-enhancing component may be fused to, swapped for, or incorporated within a terminal end of the light chain of a botulinum toxin. In some embodiments, the structural modification includes a chimeric fusion construct in which a biological persistence-reducing component or an enzymatic activity-reducing component may be fused to, swapped for, or incorporated within a terminal end of the light chain of a botulinum toxin. In some embodiments, the persistence- or activity-enhancing or persistence- or activity-reducing component is an N-terminal region including the first 30 amino acids of a light chain of a botulinum toxin, or a C-terminal region including the last 50 amino acids of a light chain of a botulinum toxin. This biological persistence- or enzymatic activity-enhancing component or biological persistence- or enzymatic activity-reducing component is swapped for, fused to, or incorporated within an N- and/or C-terminus of a light chain of a botulinum toxin to enhance or reduce its biological persistence and/or enzymatic activity.

In some embodiments, the fusion of, addition to, or swapping of the N-terminal region of the light chain of BoNT/A into a chimeric construct results in an increase in biological persistance and/or enzymatic activity. In some embodiments, a substituted, mutated, or deleted N-terminal region of the light chain of BoNT/A within a chimeric construct results in a decrease in biological persistance and/or enzymatic activity. In some embodiments, the fusion of, addition to, or swapping of the C-terminal region of the light chain of BoNT/A into a chimeric construct results in an increase in biological persistance and/or enzymatic activity. In some embodiments, a substituted, mutated, or deleted C-terminal region of the light chain of BoNT/A within a chimeric construct results in a decrease in biological persistance and/or enzymatic activity.

Generally, it is suitable that the chimeric toxin has a biological persistence of about 20% to 300% greater than an identical toxin without the structural modification. The biological persistence of the chimeric toxin may be enhanced by about 100%. That is, for example, the modified botulinum neurotoxin including the biological persistence-enhancing component is able to cause a substantial inhibition of neurotransmitter release (for example, acetylcholine) from a nerve terminal for about 20% to about 300% longer than a neurotoxin without the structural modification.

Similarly, it is suitable that the chimeric botulinum toxin light chain has an altered enzymatic activity. For example, the chimeric toxin can exhibit a reduced or an enhanced inhibition of exocytosis (such as exocytosis of a neurotransmitter) from a target cell with or without any alteration in the biological persistence of the modified neurotoxin. Altered enzymatic activities include increased or decreased efficiency or potency, increased or decreased localization to the plasma membrane, increased or decreased substrate specificity, and/or increased or decreased rate of proteolysis of SNAP/SNARE proteins. An increase in enzymatic activity can be from 1.5 to 5 times greater than the biological activity of the native or unmodified light chain. For example, the chimeric botulinum neurotoxin including the enzymatic activity-enhancing component is able to cause a substantial inhibition of neurotransmitter release (for example, acetylcholine) from a nerve terminal due to an increased rate of proteolysis of the SNAP-25 substrate as compared to a neurotoxin without the structural modification.

It has been observed that a recombinant construct with both eight amino acid residues (PFVNKQFN; SEQ ID NO: 120) deleted from the N-terminus and twenty-two amino acid residues (KNFTG LFEFYKLLCV RGIITSK; SEQ ID NO: 121) deleted from the C-terminus of the light chain of botulinum toxin A exhibits a reduced activity such that the effective concentration ($EC_{50}$) required to cleave the SNAP-25 substrate is nearly ten-fold greater than that of a similar construct with only the C-terminal twenty-two amino acid deletion ($EC_{50}$ ΔN8ΔC22=4663 pM vs. $EC_{50}$ΔC22=566 pM). The recombinant light chain of botulinum toxin A was used as a control ($EC_{50}$ rLC/A=7 pM), and, therefore, as compared to the rLC/A construct, a 666-fold greater concentration of the ΔN8ΔC22 construct is required. A recombinant light chain construct with the dileucine motif mutated to dialanine [rLC/A(LL-->AA)] also exhibits reduced activity ($EC_{50}$ rLC/A (LL-->AA)=184 pM); however, the effective concentration of the ΔN8ΔC22 construct is twenty-five fold greater than the rLC/A(LL-->AA) construct.

A modified light chain may include a light chain from botulinum toxins A, B, C1, D, E, F or G. One or multiple domains at the N- and/or C-terminus may be modified by addition, deletion or substitution. For example, a modified chimeric light chain component may include a light chain from BoNT/E modified by adding or replacing/substituting one or more N- and/or C-terminal end sequences derived from the BoNT/A light chain, thereby resulting in a chimeric BoNT/E-BoNT/A chimeric light chain with one or both terminal ends having one or more sequences which convey an increased or decreased ability to localize to a plasma membrane, increased or decreased biological persistence and/or an increased or decreased enzymatic activity.

A chimeric botulinum toxin can be constructed such that a C-terminal portion of the light chain of one botulinum toxin serotype replaces a similar C-terminal portion within the light chain of another botulinum toxin serotype. For example, the last twenty two amino acid residues bearing the dileucine motif from the C-terminus of the light chain of BoNT/A can replace the last twenty two amino acid residues of the C-terminus of the light chain of BoNT/E. The amino acid sequence of the entire light chain of such a chimeric construct is shown below:

(SEQ ID NO: 124)
MPKINSFNYNDPVNDRTILYIKPGGCQEFYKSFNIMKNIWIIPERNVIGT

TPQDFHPPTSLKNGDSSYYDPNYLQSDEEKDRFLKIVTKIFNRINNNLSG

GILLEELSKANPYLGNDNTPDNQFHIGDASAVEIKFSNGSQDILLPNVII

MGAEPDLFETNSSNISLRNNYMPSNHGFGSIAIVTFSPEYSFRFNDNSMN

EFIQDPALTLMHELIHSLHGLYGAKGITTKYTITQKQNPLITNIRGTNIE

EFLTFGGTDLNIITSAQSNDIYTNLLADYKKIASKLSKVQVSNPLLNPYK

DVFEAKYGLDKDASGIYSVNINKFNDIFKKLYSFTEFDLATKFQVKCRQT

YIGQYKYFKLSNLLNDSIYNISEGYNINNLKVNFRGQNANLNPRIITPIT

GKNFTGLFEFYKLLCVRGIITSK

In the construct above, the majority of the amino acid sequence is derived from BoNT/E serotype, and the amino acids shown in bold underlined text are derived from the last twenty two amino acid residues of the C-terminus of the light chain of BoNT/A which bears the dileucine motif.

In a further example, the first thirty amino acid residues from the N-terminus of the light chain of BoNT/A can replace the first thirty amino acid residues of the N-terminus of the light chain of BoNT/B. The amino acid sequence of the entire light chain of such a chimeric construct is shown below:

(SEQ ID NO: 125)
MPFVNKQFNYKDPVNGVDIAYIKIPNAGQMGRYYKAFKITDRIWIIPERY

TFGYKPEDFNKSSGIFNRDVCEYYDPDYLNTNDKKNIFFQTLIKLFNRIK

SKPLGEKLLEMIINGIPYLGDRRVPLEEFNTNIASVTVNKLISNPGEVER

KKGIFANLIIFGPGPVLNENETIDIGIQNHFASREGFGGIMQMKFCPEYV

SVFNNVQENKGASIFNRRGYFSDPALILMHELIHVLHGLYGIKVDDLPIV

PNEKKFFMQSTDTIQAEELYTFGGQDPSIISPSTDKSIYDKVLQNFRGIV

DRLNKVLVCISDPNININIYKNKFKDKYKFVEDSEGKYSIDVESFNKLYK

SLMLGFTEINIAENYKIKTRASYFSDSLPPVKIKNLLDNEIYTIEEGFNI

SDKNMGKEYRGQNKAINKQAYEEISKEHLAVYKIQMCKSVK

In the construct above, the majority of the amino acid sequence is derived from BoNT/B serotype, and the amino acids shown in bold underlined text are derived from the first thirty amino acid residues of the N-terminus of the light chain of BoNT/A.

Still further, the chimeric construct can have both N-terminal and the C-terminal replacements. For example, the first nine amino acid residues from the N-terminus of the light chain of BoNT/A can replace the first nine amino acid residues of the N-terminus of the light chain of BoNT/E. Additionally, in the same construct, the last twenty-two amino acid residues from the C-terminus of the light chain of BoNT/A can replace the last twenty-two amino acid residues from the C-terminus of the light chain of BoNT/E. The amino acid sequence of the entire light chain of such a chimeric construct is shown below:

(SEQ ID NO: 126)
MPFVNKQFNNDPVNDRTILYIKPGGCQEFYKSFNIMKNIWIIPERNVIGT

TPQDFHPPTSLKNGDSSYYDPNYLQSDEEKDRFLKIVTKIFNRINNNLSG

GILLEELSKANPYLGNDNTPDNQFHIGDASAVEIKFSNGSQDILLPNVII

MGAEPDLFETNSSNISLRNNYMPSNHGFGSIAIVTFSPEYSFRFNDNSMN

EFIQDPALTLMHELIHSLHGLYGAKGITTKYTITQKQNPLITNIRGTNIE

EFLTFGGTDLNIITSAQSNDIYTNLLADYKKIASKLSKVQVSNPLLNPYK

-continued

DVFEAKYGLDKDASGIYSVNINKFNDIFKKLYSFTEFDLATKFQVKCRQT

YIGQYKYFKLSNLLNDSIYNISEGYNINNLKVNFRGQNANLNPRIITPIT

GKNFTGLFEFYKLLCVRGIITSK

In the construct above, the majority of the amino acid sequence is derived from BoNT/E serotype, and the amino acids shown in bold underlined text are derived from the first nine amino acid residues of the N-terminus and the last twenty-two amino acid residues of the C-terminus of the light chain of BoNT/A.

Similarly, the first nine amino acid residues from the N-terminus of the light chain of BoNT/A can replace the first nine amino acid residues of the N-terminus of the light chain of BoNT/B. Additionally, in the same construct, the last twenty-two amino acid residues from the C-terminus of the light chain of BoNT/A can replace the last twenty-two amino acid residues from the C-terminus of the light chain of BoNT/B. The amino acid sequence of the entire light chain of such a chimeric construct is shown below:

(SEQ ID NO: 127)
MPFVNKQFNYNDPIDNDNIIMMEPPFARGTGRYYKAFKITDRIWIIPERY

TFGYKPEDFNKSSGIFNRDVCEYYDPDYLNTNDKKNIFFQTLIKLFNRIK

SKPLGEKLLEMIINGIPYLGDRRVPLEEFNTNIASVTVNKLISNPGEVER

KKGIFANLIIFGPGPVLNENETIDIGIQNHFASREGFGGIMQMKFCPEYV

SVFNNVQENKGASIFNRRGYFSDPALILMHELIHVLHGLYGIKVDDLPIV

PNEKKFFMQSTDTIQAEELYTFGGQDPSIISPSTDKSIYDKVLQNFRGIV

DRLNKVLVCISDPNININIYKNKFKDKYKFVEDSEGKYSIDVESFNKLYK

SLMLGFTEINIAENYKIKTRASYFSDSLPPVKIKNLLDNEIYTIEEGFNI

SDKNMGKEYRGQNKAINKQKNFTGLFEFYKLLCVRGIITSK

In the construct above, the majority of the amino acid sequence is derived from BoNT/B serotype, and the amino acids shown in bold underlined text are derived from the first nine amino acid residues of the N-terminus and the last twenty-two amino acid residues of the C-terminus of the light chain of BoNT/A.

Furthermore, the first nine amino acid residues from the N-terminus of the light chain of BoNT/A can replace the first nine amino acid residues of the N-terminus of the light chain of BoNT/F. Additionally, in the same construct, the last twenty-two amino acid residues from the C-terminus of the light chain of BoNT/A can replace the last twenty-two amino acid residues from the C-terminus of the light chain of BoNT/F. The amino acid sequence of the entire light chain of such a chimeric construct is shown below:

(SEQ ID NO: 128)
MPFVNKQFNYNDPVNDDTILYMQIPYEEKSKKYYKAFEIMRNVWIIPERN

TIGTNPSDFDPPASLKNGSSAYYDPNYLTTDAEKDRYLKTTIKLFKRINS

NPAGKVLLQEISYAKPYLGNDHTPIDEFSPVTRTTSVNIKLSTNVESSML

LNLLVLGAGPDIFESCCYPVRKLIDPDVVYDPSNYGFGSINIVTFSPEYE

YTFNDISGGHNSSTESFIADPAISLAHELIHALHGLYGARGVTYEETIEV

KQAPLMIAEKPIRLEEFLTFGGQDLNIITSAMKEKIYNNLLANYEKIATR

-continued
LSEVNSAPPEYDINEYKDYFQWKYGLDKNADGSYTVNENKFNEIYKKLYS

FTESDLANKFKVKCRNTYFIKYEFLKVPNLLDDDIYTVSEGFNIGNLAVN

NRGQSIKLNPKIIDKNFTGLFEFYKLLCVRGIITSK

In the construct above, the majority of the amino acid sequence is derived from BoNT/F serotype, and the amino acids shown in bold underlined text are derived from the first nine amino acid residues of the N-terminus and the last twenty-two amino acid residues of the C-terminus of the light chain of BoNT/A.

In some embodiments, a light chain can be engineered such that one or more segments of the light chain of one or more toxin serotypes replace one or more segments of equal or unequal length within the light chain of another toxin serotype. In a non-limiting example of this kind of chimeric construct, fifty amino acid residues from the N-terminus of the light chain of BoNT/A can replace eight amino acid residues of the N-terminus of the light chain of BoNT/B, resulting in a net gain of forty-two amino acids in length in the N-terminal region of the light chain chimera. The amino acid sequence of the entire light chain of such a chimeric construct is shown below:

(SEQ ID NO: 129)
MPFVNKQFNYKDPVNGVDIAYIKIPNAGQMQPVKAFKIHNKIWVIPERDT

FYNDPIDNDNIIMMEPPFARGTGRYYKAFKITDRIWIIPERYTFGYKPED

FNKSSGIFNRDVCEYYDPDYLNTNDKKNIFFQTLIKLFNRIKSKPLGEKL

LEMIINGIPYLGDRRVPLEEFNTNIASVTVNKLISNPGEVERKKGIFANL

IIFGPGPVLNENETIDIGIQNHFASREGFGGIMQMKFCPEYVSVFNNVQE

NKGASIFNRRGYFSDPALILMHELIHVLHGLYGIKVDDLPIVPNEKKFFM

QSTDTIQAEELYTFGGQDPSIISPSTDKSIYDKVLQNFRGIVDRLNKVLV

CISDPNININIYKNKFKDKYKFVEDSEGKYSIDVESFNKLYKSLMLGFTE

INIAENYKIKTRASYFSDSLPPVKIKNLLDNEIYTIEEGFNISDKNMGKE

YRGQNKAINKQAYEEISKEHLAVYKIQMCKSVK

In the construct above, the majority of the amino acid sequence is derived from BoNT/B serotype, and the amino acids shown in bold underlined text are derived from the first fifty amino acid residues of the N-terminus of the light chain of BoNT/A.

In a non-limiting example of this kind of chimeric construct, the last fifty amino acid residues from the C-terminus of the light chain of BoNT/A can replace fifteen amino acid residues within the C-terminus of the light chain of BoNT/E, resulting in a net gain of thirty-five amino acids in the C-terminal region of the light chain chimera. The amino acid sequence of the entire light chain of such a chimeric construct is shown below:

(SEQ ID NO: 130)
MPKINSFNYNDPVNDRTILYIKPGGCQEFYKSFNIMKNIWIIPERNVIGT

TPQDFHPPTSLKNGDSSYYDPNYLQSDEEKDRFLKIVTKIFNRINNNLSG

GILLEELSKANPYLGNDNTPDNQFHIGDASAVEIKFSNGSQDILLPNVII

MGAEPDLFETNSSNISLRNNYMPSNHGFGSIAIVTFSPEYSFRFNDNSMN

EFIQDPALTLMHELIHSLHGLYGAKGITTKYTITQKQNPLITNIRGTNIE

```
EFLTFGGTDLNIITSAQSNDIYTNLLADYKKIASKLSKVQVSNPLLNPYK

DVFEAKYGLDKDASGIYSVNINKFNDIFKKLYSFTEFDLATKFQVKCRQT

YIGQYKYFKLSNLLNDSIYNISEGYNINNLKVNFRGQNANLNPRIITPGF

NLRNTNLAANFNGQNTEINNMNFTKLKNFTGLFEFYKLLCVRGIITSKNI

VSVKGIRK
```

In the construct above, the majority of the amino acid sequence is derived from BoNT/E serotype, and the amino acids shown in bold underlined text are derived from the last fifty amino acid residues of the C-terminus of the light chain of BoNT/A.

In a non-limiting example of this kind of chimeric construct, thirty amino acid residues from the N-terminus of the light chain of BoNT/A can replace ten amino acid residues of the N-terminus of the light chain of BoNT/E, resulting in a net gain of twenty amino acids in length in the N-terminal region of the chimera. Additionally, in the same construct, the last fifty amino acid residues from the C-terminus of the light chain of BoNT/A can replace the last fifty amino acid residues from the C-terminus of the light chain of BoNT/E. The amino acid sequence of the entire light chain of such a chimeric construct is shown below:

```
                                          (SEQ ID NO: 131)
MPKINSFNYMPFVNKQFNYKDPVNGVDIAYIKIPNAGQMYIKPGGCQEFY

KSFNIMKNIWIIPERNVIGTTPQDFHPPTSLKNGDSSYYDPNYLQSDEEK

DRFLKIVTKIFNRINNNLSGGILLEELSKANPYLGNDNTPDNQFHIGDAS

AVEIKFSNGSQDILLPNVIIMGAEPDLFETNSSNISLRNNYMPSNHGFGS

IAIVTFSPEYSFRFNDNSMNEFIQDPALTLMHELIHSLHGLYGAKGITTK

YTITQKQNPLITNIRGTNIEEFLTFGGTDLNIITSAQSNDIYTNLLADYK

KIASKLSKVQVSNPLLNPYKDVFEAKYGLDKDASGIYSVNINKFNDIFKK

LYSFTEFDLATKFQVKCRQTYIGQYKYFKLSNLLNDSIYNISEGFNLRNT

NLAANFNGQNTEINNMNFTKLKNFTGLFEFYKLLCVRGIITSK
```

In the construct above, the majority of the amino acid sequence is derived from BoNT/E serotype, and the amino acids shown in bold underlined text are derived from the thirty amino acid residues of the N-terminus and the last fifty amino acid residues of the C-terminus of the light chain of BoNT/A.

In a non-limiting example of this kind of chimeric construct, thirty amino acid residues from the N-terminus of the light chain of BoNT/A can replace ten amino acid residues of the N-terminus of the light chain of BoNT/B, resulting in a net gain of twenty amino acids in length in the N-terminal region of the chimera. Additionally, in the same construct, the last fifty amino acid residues from the C-terminus of the light chain of BoNT/A can replace the last fifty amino acid residues from the C-terminus of the light chain of BoNT/B. The amino acid sequence of the entire light chain of such a chimeric construct is shown below:

```
                                          (SEQ ID NO: 132)
MPVTINNFNMPFVNKQFNYKDPVNGVDIAYIKIPNAGQMIMMEPPFARGT

GRYYKAFKITDRIWIIPERYTFGYKPEDFNKSSGIFNRDVCEYYDPDYLN

TNDKKNIFFQTLIKLFNRIKSKPLGEKLLEMIINGIPYLGDRRVPLEEFN

TNIASVTVNKLISNPGEVERKKGIFANLIIFGPGPVLNENETIDIGIQNH

FASREGFGGIMQMKFCPEYVSVFNNVQENKGASIFNRRGYFSDPALILMH

ELIHVLHGLYGIKVDDLPIVPNEKKFFMQSTDTIQAEELYTFGGQDPSII

SPSTDKSIYDKVLQNFRGIVDRLNKVLVCISDPNININIYKNKFKDKYKF

VEDSEGKYSIDVESFNKLYKSLMLGFTEINIAENYKIKTRASYFSDSLPP

VKIKNLLDNEIGFNLRNTNLAANFNGQNTEINNMNFTKLKNFTGLFEFYK

LLCVRGIITSK
```

In the construct above, the majority of the amino acid sequence is derived from BoNT/B serotype, and the amino acids shown in bold underlined text are derived from the thirty amino acid residues of the N-terminus and the last fifty amino acid residues of the C-terminus of the light chain of BoNT/A.

In a non-limiting example of this kind of chimeric construct, thirty amino acid residues from the N-terminus of the light chain of BoNT/A can replace ten amino acid residues of the N-terminus of the light chain of BoNT/F, resulting in a net gain of twenty amino acids in length in the N-terminal region of the chimera. Additionally, in the same construct, the last fifty amino acid residues from the C-terminus of the light chain of BoNT/A can replace the last fifty amino acid residues from the C-terminus of the light chain of BoNT/F. The amino acid sequence of the entire light chain of such a chimeric construct is shown below:

```
                                          (SEQ ID NO: 133)
MPVAINSFNMPFVNKQFNYKDPVNGVDIAYIKIPNAGQMLYMQIPYEEKS

KKYYKAFEIMRNVWIIPERNTIGTNPSDFDPPASLKNGSSAYYDPNYLTT

DAEKDRYLKTTIKLFKRINSNPAGKVLLQEISYAKPYLGNDHTPIDEFSP

VTRTTSVNIKLSTNVESSMLLNLLVLGAGPDIFESCCYPVRKLIDPDVVY

DPSNYGFGSINIVTFSPEYEYTFNDISGGHNSSTESFIADPAISLAHELI

HALHGLYGARGVTYEETIEVKQAPLMIAEKPIRLEEFLTFGGQDLNIITS

AMKEKIYNNLLANYEKIATRLSEVNSAPPEYDINEYKDYFQWKYGLDKNA

DGSYTVNENKFNEIYKKLYSFTESDLANKFKVKCRNTYFIKYEFLKVPNL

LDDDIYGFNLRNTNLAANFNGQNTEINNMNFTKLKNFTGLFEFYKLLCVR

GIITSK
```

In the construct above, the majority of the amino acid sequence is derived from BoNT/F serotype, and the amino acids shown in bold underlined text are derived from the thirty amino acid residues of the N-terminus and the last fifty amino acid residues of the C-terminus of the light chain of BoNT/A.

In some embodiments, the swapped sequences can be derived from two different serotypes, resulting in a chimera with regions from three different serotypes in all. In this example, eight amino acid residues from the N-terminus of the light chain of BoNT/B can replace five amino acid residues of the N-terminus of the light chain of BoNT/E, resulting in a net gain of three amino acids in length in the N-terminal region of the chimera. Additionally, in the same construct, 30 amino acid residues including the dileucine repeat of the C-terminus of the light chain of BoNT/A can replace ten amino acid residues within the C-terminus of the light chain of BoNT/E, resulting in a net gain of 20 amino acids in the C-terminal region of the chimera. The amino acid sequence of the entire light chain of such a chimeric construct is shown below:

(SEQ ID NO: 134)
MPKINSFNYNDP _VTINNFNY_DRTILYIKPGGCQEFYKSFNIMKNIWIIPE

RNVIGTTPQDFHPPTSLKNGDSSYYDPNYLQSDEEKDRFLKIVTKIFNRI

NNNLSGGILLEELSKANPYLGNDNTPDNQFHIGDASAVEIKFSNGSQDIL

LPNVIIMGAEPDLFETNSSNISLRNNYMPSNHGFGSIAIVTFSPEYSFRF

NDNSMNEFIQDPALTLMHELIHSLHGLYGAKGITTKYTITQKQNPLITNI

RGTNIEEFLTFGGTDLNIITSAQSNDIYTNLLADYKKIASKLSKVQVSNP

LLNPYKDVFEAKYGLDKDASGIYSVNINKFNDIFKKLYSFTEFDLATKFQ

VKCRQTYIGQYKYFKLSNLLNDSIYNISEGYNINNLKVNFRGQNANLNPR

IITPITGRGLVKKIIRFCKNNMNFTKLKNFTGLFEFYKLLCVRGIITSK

In the construct above, the majority of the amino acid sequence is derived from BoNT/E serotype, and the amino acids shown in bold italicized text are derived from eight amino acid residues of the N-terminus of the light chain of BoNT/B and thirty amino acid residues shown in bold underlined text are derived from thirty amino acid residues of the C-terminus of the light chain of BoNT/A.

In a non-limiting example, eight amino acid residues from the N-terminus of the light chain of BoNT/B can replace five amino acid residues of the N-terminus of the light chain of BoNT/F, resulting in a net gain of three amino acids in length in the N-terminal region of the chimera. Additionally, in the same construct, 30 amino acid residues including the dileucine repeat of the C-terminus of the light chain of BoNT/A can replace ten amino acid residues within the C-terminus of the light chain of BoNT/F, resulting in a net gain of 20 amino acids in the C-terminal region of the chimera. The amino acid sequence of the entire light chain of such a chimeric construct is shown below:

(SEQ ID NO: 135)
MPVAINSFNYND _VTINNFNY_TIILYMQIPYEEKSKKYYKAFEIMRN-VWIIP

ERNTIGTNPSDFDPPASLKNGSSAYYDPNYLTTDAEKDRYLKTTIKLFKR

INSNPAGKVLLQEISYAKPYLGNDHTPIDEFSPVTRTTSVNIKLSTNVES

SMLLNLLVLGAGPDIFESCCYPVRKLIDPDVVYDPSNYGFGSINIVTFSP

EYEYTFNDISGGHNSSTESFIADPAISLAHELIHALHGLYGARGVTYEET

IEVKQAPLMIAEKPIRLEEFLTFGGQDLNIITSAMKEKIYNNLLANYEKI

ATRLSEVNSAPPEYDINEYKDYFQWKYGLDKNADGSYTVNENKFNEIYKK

LYSFTESDLANKFKVKCRNTYFIKYEFLKVPNLLDDDIYTVSEGFNIGNL

AVNNRGQSIKLNPKIIDSIPDKGLVEKNNMNFTKLKNFTGLFEFYKLLCV

RGIITSKRK

In the construct above, the majority of the amino acid sequence is derived from BoNT/F serotype, and the amino acids shown in bold italicized text are derived from eight amino acid residues of the N-terminus of the light chain of BoNT/B and thirty amino acid residues shown in bold underlined text are derived from thirty amino acid residues of the C-terminus of the light chain of BoNT/A.

Example 14

The invention also provides for a light chain of a botulinum toxin B, C1, D, E, F or G comprising about the first 30 amino acids from the N-terminus of the light chain of botulinum toxin type A and about the last 50 amino acids from the C-terminus of the light chain of botulinum toxin type A. The first 30 amino acids of the N-terminus of type A here may be all or part, for example 2-16 contiguous or non contiguous amino acids, of the 30 amino acids. The last 50 amino acids here may be all or part, for example 5-43 contiguous or non-contiguous, amino acids of the 50 amino acids.

In some embodiments, such a light chain comprises about the first 20 amino acids from the N-terminus of the light chain of botulinum toxin type A and about the last 30 amino acids from the C-terminus of the light chain of botulinum toxin type A. The first 20 amino acids of the N-terminus of type A here may be all or part, for example 2-16 contiguous or non contiguous amino acids, of the 20 amino acids. The last 30 amino acids here may be all or part, for example 5-23 contiguous or non-contiguous, amino acids of the 30 amino acids.

In some embodiments, such a light chain comprises about the first 4 to 8, e.g. the first 8, amino acids from the N-terminus of the light chain of botulinum toxin type A and about the last 7 to 22, e.g. the last 22, amino acids from the C-terminus of the light chain of botulinum toxin type A. The first 8 amino acids of the N-terminus of type A here may be all or part, for example 2-7 contiguous or non contiguous amino acids, of the 7 amino acids. The last 22 amino acids here may be all or part, for example 5-16 contiguous or non-contiguous, amino acids of the 20 amino acids.

In some embodiments, the inclusion of about the first 30 amino acids from the N-terminus and about the last 50 amino acids from the C-terminus of the light chain of type A replaces one or more amino acids at the N- and C-termini, respectively, of the light chain of botulinum toxin type B, C1, D, E, F or G. The first 30 amino acids of the N-terminus of type A here may be all or part, for example 2-16 contiguous or non contiguous amino acids, of the 30 amino acids. The last 50 amino acids here may be all or part, for example 5-43 contiguous or non-contiguous, amino acids of the 50 amino acids.

In some embodiments, the inclusion of about the 20 amino acids from the N-terminus and about the 30 amino acids from the C-terminus of the light chain of type A replaces one or more amino acids at the N- and C-termini, respectively, of the light chain of botulinum toxin type B, C1, D, E, F or G. The first 20 amino acids of the N-terminus of type A here may be all or part, for example 2-16 contiguous or non contiguous amino acids, of the 20 amino acids. The last 30 amino acids here may be all or part, for example 5-23 contiguous or non-contiguous, amino acids of the 30 amino acids.

In some embodiments, the inclusion of about the first 4 to 8, for example the first 8, amino acids from the N-terminus and about the last 7 to 22, for example the last 22, amino acids from the C-terminus of the light chain of type A replaces one or more amino acids at the N- and C-termini, respectively, of the light chain of botulinum toxin type B, C1, D, E, F or G. The first 8 amino acids of the N-terminus of type A here may be all or part, for example 2-7 contiguous or non contiguous amino acids, of the 7 amino acids. The last 22 amino acids here may be all or part, for example 5-16 contiguous or non-contiguous, amino acids of the 20 amino acids.

The invention also provides for a modified botulinum toxin comprising the light chain of described herein, including the ones described in the Examples above.

Example 15

Generation of LC/E Chimeras

Truncation of 8 amino acids at the N-terminus of the LC/A (SEQ ID NO: 120) completely disrupts plasma membrane localization. The LC/A(ΔN8) is cytoplasmic with a distribution similar to LC/E. The sequences at the N-terminus of LC/A and LC/E are different (FIG. 1).

To generate the LC/E with the N-terminus of the LC/A we pursued two different approaches. The first one was to perform PCR on the native beluga LC/E gene with a 5' primer that contains the N-terminus of the LC/A. Primers for PCR were:

```
N-ter LC/A forward:
                                    (SEQ ID NO: 146)
5'ACCGGATCCCCATTTGTTAATAAACAGTTTAATTATAATGA 3'

N-ter LC/A reverse:
                                    (SEQ ID NO: 147)
5' CGCGAAGCTTCCTTATGCCTTTTACAGAAACAATATTTTTAC 3'
```

The PCR was performed with 0.4 μg of the plasmid template pQBI25fC3beluga LC/E, and 125 ng of each primer. The cycling program was:

Denaturalizat: 95° C. for 15 min
- 5 cycles
  - 94° C. for 30 sec
  - 50° C. for 30 sec
  - 72° C. for 1 min
- 25 cycles
  - 94° C. for 30 sec
  - 68° C. for 30 sec
  - 72° C. for 1 min Extension: 72° C. for 10 min The first five cycles at low annealing temperature will allow the primer to anneal to the 5' sequence of the LC/E despite the differences in sequence. The second set of 25 cycles will use the product with the right sequence for further and more restricted amplification.

The second strategy to generate the LC/E chimera with the N-terminus of the LC/A was to mutate one amino acid as a time using site-directed mutagenesis. The primers designed were as follow:

1. Change the sequence on LC/E from Pro-Lys-Ile to Pro-Phe-Val:

```
                                    (SEQ ID NO: 148)
5' CCGGTTACCGGTACCGGATCCCCATTTGTTAATAGTTTTAATTA
T 3'
```

2. Change the sequence Pro-Phe-Val-Asn-Ser to Pro-Phe-Val-Asn-Lys:

```
                                    (SEQ ID NO: 149)
5' CGGATCCCCATTTGTTAATAAATTTAATTATAATGATCCTGTT 3'
```

3. Insert a glutamine to complete the N-terminal sequence of the LC/A in the LC/E:

```
                                    (SEQ ID NO: 150)
5' GATCCCCATTTCTTAATAAACAGTTTAATTATAATGATCCTGTT 3'
```

Primers shown are on the sense strand, a complimentary primer corresponding to the antisense strand was also ordered and used in the PCR. The template used in the QuikChange mutagenesis was pQBI25fC3beluga LC/E.

We also analyzed the importance of the di-leucine motif present only in the LC/A by generating a motif in the LC/E in a similar area at the C-terminus (FIG. 2). The sequence in the LC/E reads LxxxlI (SEQ ID NO: 163). Since Isoleucines can substitute for Leucines in some of the motif published we designed primers to generate ExxxII (SEQ ID NO: 144), and also primers to generate ExxxLL (SEQ ID NO: 145). Those mutations were done in the native LC/E gene and also in the LC/E containing the N-terminus of the LC/A.

We generated a total of 5 chimeras with all the combinations of the N-terminus of the LC/A and various stages of the di-leucine motif construction as seen in FIG. 3. The complete DNA and annotated amino acid sequence of the wild type LC/E, the chimeric LC/E with the N-terminus of the LC/A, the chimeric LC/E with the LC/A di-leucine motif at the C-terminus, and the full chimeric LC/E with both the N-terminus and the di-leucine motif from LC/A are shown in FIGS. 14-17. We have tested all those mutants for expression, activity, and subcellular localization.

Cell Lines and Growth Conditions

SH-SY5Y (Human Neuroblastoma cell line) cells were cultured in Costar brand polystyrene flasks with vented caps. Growth media consisted of Minimum Essential Medium with Earle's salts and L-glutamine, F-12 Nutrient Mixture (Ham) with L-glutamine, 10% Fetal Bovine Serum (heat-inactivated), Non-Essential Amino-Acids, HEPES, L-Glutamine, Penicillin/Streptomycin. PC-12 (Rat Chromaffin Pheochromocytoma cell line) cells were maintained on Collagen IV coated BD Biocoat dishes (BD Biosciences, Bedford, Mass.). Growth media consisted of RPMI-1640 with L-glutamine, 10% Horse Serum (heat-inactivated), 5% Fetal Bovine Serum (heat-inactivated), HEPES, D-Glucose (Sigma), Sodium Pyruvate, Penicillin/Streptomycin. All (except D-Glucose, Sigma) growth media components were Gibco products purchased from Invitrogen and all cell lines were cultured and maintained at 37° C. with 7.5% $CO_2$.

Transient Transfection:

The day before transfection, SH-SY5Y cells were plated at $1\times10^6$ into 6-well plates. Transfections were carried out by diluting LipofectAmine 2000 (Invitrogen, Carlsbad, Calif.) at 60 μl per ml in OPTI-MEM Reduced Serum Medium following incubation at RT for 5 min. Next, we diluted 20 μg DNA per ml in OPTI-MEM, then combined equal amount of DNA mix and LipofectAmine 2000 (LF) mix, and incubated at RT for another 20 min. Meanwhile, the culture medium in the plates were replaced with 2 ml of serum free medium, 0.5 ml of DNA+LF mix was then added into the wells and incubated at 37° C. $CO_2$ incubator for 6 hours. After the incubation the medium was removed and replaced with 10% FCS culture medium. The cells were harvested 24 hours post transfection for further analysis. For confocal analysis, transfections were usually performed in 2-well culture slices with proportionally reduced amount of reagents.

Transfection into PC12 cells were performed as follow: PC12 cells were plated the day before transfection in Collagen IV coated dishes at $10\times10^6$ cells per 100 mm dishes and $2\times10^6$ cells per 60 mm dishes. Plates were transfected with 20 μg or 10 μg respectively with Lipofectamine 2000 in OPTI-MEM media. 48 hours after transfection, cells were placed on differentiation media and collected for western blots or fixed in 4% paraformaldehyde for confocal imaging.

Western Blot Analysis:

Cells were collected in 15 ml Falcon tubes, washed once with 1 ml of PBS, and then transferred to 1.5 ml microcentrifuge tubes. Cells were lysed in 0.5 ml of lysis buffer (50 mM HEPES, 150 mM NaCl, 1.5 mM $MgCl_2$, 1 mM EGTA, 10% glycerol and 1% triton X-100) on rotator at 4° C. for 1 hour. Lysed cells were spun down at 5000 rpm at 4° C. for 10 min to eliminate debris; supernatants were transferred to fresh siliconized tubes. Protein concentrations were measured by the Bradford's method and resuspended in 1×SDS sample buffer at 1 mg/ml or higher concentration. Samples were boiled for 5 min, 20 to 40 µl of the samples were loaded on 4-12% Tris-HCl gels. Proteins were transferred to PVDF membranes, and blocked in 5% non-fat milk in TBST buffer for 1 hour at room temperature. The cleaved SNAP25 was detected with antiSNAP25$_{197}$ antibody or with antiS-NAP25$_{180}$ diluted in blocking buffer; blot was washed extensively, and the bound antibody was detected with horseradish peroxidase conjugated to species-specific antibody.

When we needed to detect SNAP25$_{206}$, SNAP25$_{197}$ and SNAP25$_{206}$ in the same blot using the Monoclonal antibody SMI-81 to the N-terminus of the SNAP25, cell lysates were run on a 12% Bis-Tris gel to allow separation of the cleaved SNAP25.

We used the Typhoon 9410 Imager (Amersham) for Western Blot Analysis instead of traditional film. After the final washes the membrane was reacted with ECL Plus western blot detection reagent (Amersham) rather than SuperSignal reagent used previously, blot was incubated at room temperature for 5 min to develop. The choice of pixel size and PMT voltage settings will depend on the individual blot. Membranes were scanned and quantified using Typhoon Scanner and Imager Analysis software.

SH-SY5Y Transient Transfections for SNAP-25 Immunocytochemistry

One day before transfection, SH-SY5Y cells were plated in 60 mm tissue culture dishes at densities of $1.5 \times 10^6$ or $1.6 \times 10^6$ cells per dish to achieve 90-95% confluence at the time of transfection. Transfections were performed by diluting 25 µl of Lipofectamine™ 2000 (Invitrogen) in 0.5 ml Opti-MEM® I Reduced Serum Medium (Invitrogen) followed by incubation at room temperature for 5 min. DNA (10 µg) was diluted in 0.5 ml Opti-MEM® I Reduced Serum Medium. The diluted DNA was mixed gently with the diluted Lipofectamine™ 2000. This mixture was incubated for 20 min at room temperature. Meanwhile, the culture medium in the plates was replaced with 2 ml of serum-free and antibiotic-free medium. The DNA plus Lipofectamine™ 2000 complex was added drop-wise to the cells and mixed into the culture medium by rocking the plates back and forth. Cells were incubated at 37° C., 7.5% $CO_2$ for 24 hours. Transfection efficiencies were determined by viewing cells with the fluorescence microscope. Transfection efficiencies obtained with the GFP construct were ca. 40-50%. Lower transfection efficiencies were observed with the GFP-LCE constructs, ca. 10-15%. Antibiotic selection of cells was accomplished in complete medium containing 0.5 mg/ml Geneticin G418 (Invitrogen) for 48 hours before proceeding with the immunocytochemistry.

PC-12 Transient Transfections for SNAP-25 Immunocytochemistry

Cells were plated one day before transfection in Collagen IV coated dishes (BD Biosciences) at $1-2 \times 10^6$ cells per 60 mm dish. Plates were transfected using 10 µg DNA and 25 µl Lipofectamine™ 2000 (each diluted in 0.5 ml Opti-MEM® I Reduced Serum Medium). The cells were incubated with the DNA/Lipofectamine™ 2000 complex for 24 hours in serum- and antibiotic-free medium at 37° C., 7.5% $CO_2$. The transfection medium was replaced with complete growth medium (serum and antibiotics included) containing 0.5 mg/ml G418 (antibiotic selection) and incubation continued at 37° C., 7.5% $CO_2$ for a further 48 hours. Cells were placed in differentiation medium (RPMI-1640 with L-glutamine, D-Glucose (Sigma), Sodium Pyruvate, Penicillin/Streptomycin, BSA (ALBUMAX II, lipid rich), N2-Supplement) containing Nerve Growth Factor (NGF) (Harlan Bioproducts for Science, Indianapolis, Ind.) at 50 ng/ml final concentration for 24 hours and stained with antibodies specific for GFP, SNAP25$_{206}$ and SNAP25$_{180}$ (Table 6).

TABLE 6

List of antibodies used in the immunocytochemistry experiments

| Antibody | Source | Dilution Used | Specificity/Immunogen |
|---|---|---|---|
| 1A3A7, ascites IgG1-K, mouse monoclonal | Allergan | 1:100, 1:50 | Anti-SNAP25$_{180}$ cleavage product. Does not cross-react with SNAP25$_{206}$ |
| 1G8C11, ascites IgG1-K, mouse monoclonal | Allergan | 1:100, 1:50 | Anti-SNAP25$_{180}$ cleavage product. Does not cross-react with SNAP25$_{206}$ |
| 1C9F3, ascites IgG1-K, mouse monoclonal | Allergan | 1:100, 1:50 | Anti-SNAP25$_{180}$ cleavage product. Does not cross-react with SNAP25$_{206}$ |
| Anti-GFP(FL), rabbit polyclonal IgG | Santa Cruz Biotechnologies | 1:100 | Full length GFP (amino acids 1-238 of *Aequorea Victoria* origin) |
| Anti-GFP, mouse monoclonal IgG2 | Abcam Inc. | 1:100 | Full length GFP (amino acids 1-246 of *Aequorea Victoria* origin) |
| Anti-SNAP-25, rabbit polyclonal | Stressgen Biotechnologies | 1:100 | Amino acids 195-206 of mouse/human/chicken SNAP-25. Specific for SNAP25$_{206}$ |
| Alexa Fluor 568 Goat Anti-Rabbit IgG (H + L), highly cross-absorbed | Molecular Probes | 1:100 | Secondary for SNAP-25$_{206}$ detection |
| Alexa Fluor 488 Goat Anti-Rabbit IgG (H + L) | Molecular Probes | 1:100, 1:200 | Secondary for rabbit polyclonal to GFP(FL) |
| Alexa Fluor 568 Goat Anti-Mouse IgG (H + L) | Molecular Probes | 1:100 | Secondary for mouse monoclonals to SNAP25$_{180}$ |
| Alexa Fluor 488 Goat Anti-Mouse IgG (H + L) | Molecular Probes | 1:100 | Secondary for mouse monoclonal to GFP |

Figure 8:
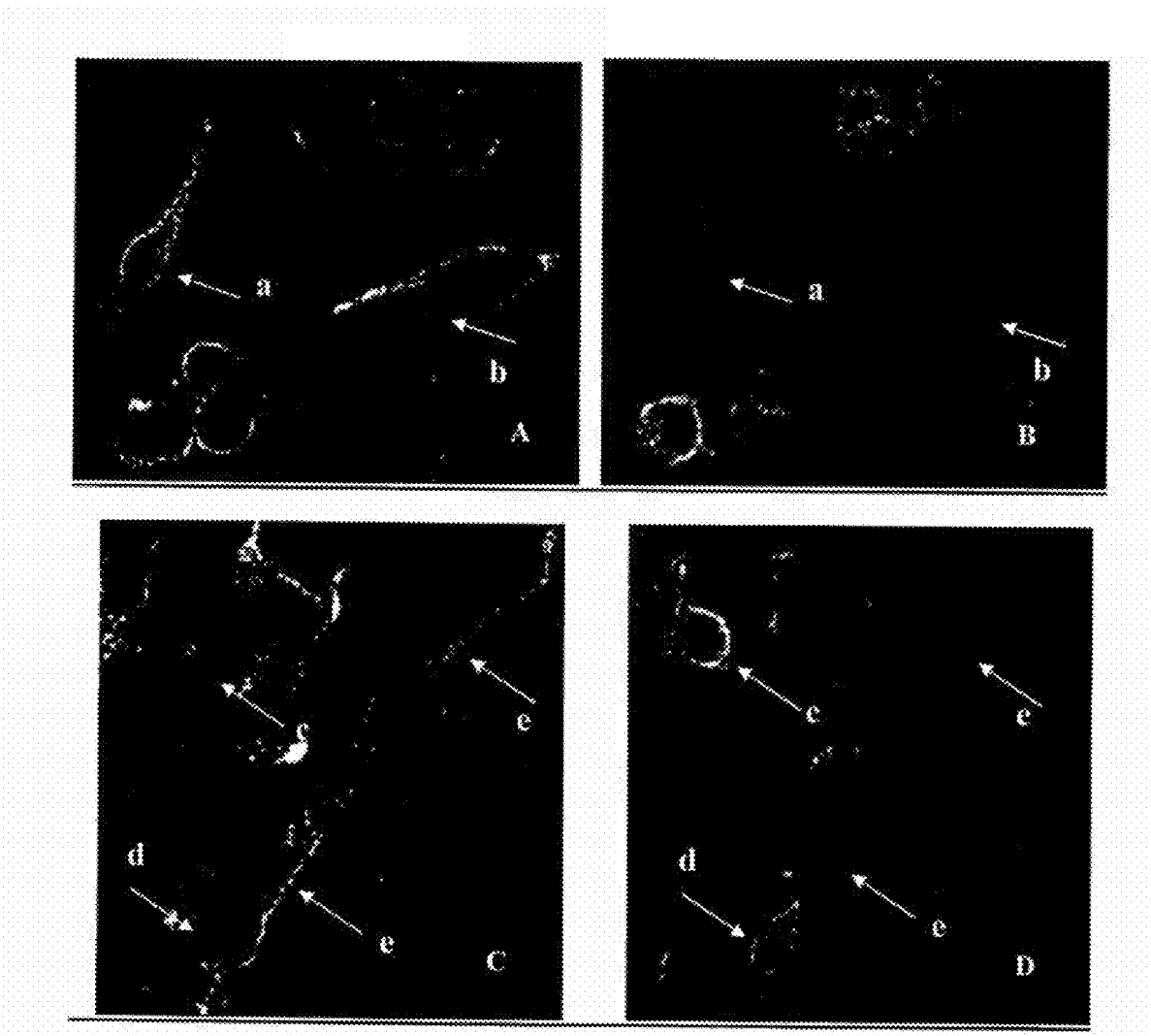
FIG. 8: Differentiated PC-12 cells transfected with GFP-LC/E (N-LCA/ExxxLL). Cells were immunostained with antibodies to GFP, mouse monoclonal at 1:100 (FIGS. 8A and 8C) and Anti-SNAP25$_{206}$ rabbit polyclonal antibody at 1:100 (FIGS. 8B and 8D). (63× magnification). Specific cells are indicated by an arrow and are designated a, b, c, d or e. Transfected cells do not contain SNAP25$_{206}$ that is only present in non-transfected cells.

Immunocytochemistry Using Fixative Paraformaldehyde for SNAP25$_{206}$ and SNAP25$_{180}$ Growth medium was removed from cells by aspiration and cells were washed twice with PBS (Invitrogen, Carlsbad, Calif.). Cells were fixed with 4% paraformaldehyde in PBS (Electron Microscopy Sciences, Washington, Pa.) for 15 to 30 min at room temperature and washed in three changes of PBS. Cells were permeabilized with 0.5% Triton X-100 in PBS for 5 min at room temperature and washed in PBS a total of three times. Cells were again permeabilized in ice-cold methanol for 6 min at −20° C. Methanol was removed by aspiration and dishes inverted to allow the cells to dry at room temperature. Wells were drawn around cells using a Pap pen (Zymed, San Francisco, Calif.) and cells were washed and rehydrated in six changes of PBS. Cells were blocked with 100 mM glycine in PBS for 30 min at room temperature followed by three washes in PBS. Cells were incubated in 0.5% BSA in PBS for 30 min at room temperature washed in three changes of PBS before addition of the primary antibodies diluted in 0.5% BSA in PBS (Table 6). Cells were incubated at room temperature in a humid chamber for 2 hours or at 4° C. overnight. Primary antibody was removed by a PBS wash without incubation and was followed by three 5 min washes in PBS. Cells were incubated with the fluorescently labeled secondary antibodies (Alexa Fluor Anti-Mouse or Anti-Rabbit Antibodies, Molecular Probes, Table 6) diluted in 0.5% BSA/PBS for 1 hour at room temperature in a humid chamber and washed in PBS. Cells were mounted using VECTASHIELD® Mounting Medium (Vector, Burlingham, Calif.) and coverslipped. Cells were stored at 4° C. before viewing with a Leica confocal microscope Results Generation of LC/E Chimeras Containing the Localization Signals for LC/A We have identified sequences in the N-terminus and C-terminus of the LC/A that are important for localization of the protein to the plasma membrane. Deletion of the first 8 amino acids at the N-terminus causes complete loss of plasma membrane localization, with the LC/A(ΔN8) localizing in the cytoplasm with nuclear exclusion. Disruption of the di-leucine motif at the C-terminus produces also changes in localization. To validate those signals we generated chimeras between the LC/A and the LC/E, since both cleave the same substrate at different sites, but have different subcellular localization and duration of action. LC/E localizes to the cytoplasm and lasts 1-2 weeks. We generated the following constructs using the native beluga LC/E sequence of SEQ ID NO: 136: LC/E(N-LCA) of SEQ ID NO: 138, LC/E(ExxxII) of SEQ ID NO: 122, LC/E(ExxxLL) of SEQ ID NO: 140, LC/E(N-LCA/ExxxII) of SEQ ID NO: 123, and LC/E(N-LCA/ExxxLL) of SEQ ID NO: 142 (FIG. 3 and Table 7) in order to analyze the effect of each signal by itself, and the effect of both signals combined. These constructs were transfected into the human neuroblastoma cell line SH-SY5Y. Cell lysates were prepared and the activity of the mutants was analyzed with the SMI-81 antibody that recognizes both cleaved and intact SNAP25 (FIG. 4).

TABLE 7

| Name | Contains GFP attached to: |
|---|---|
| GFP-LCE | SEQ ID NO: 136, a Wild-type-LC/E |
| GFP-LCE Nterm LCA | SEQ ID NO: 138, a LC/E with the first eight amino-acid of LC/A at the N-terminus |
| GFP-LCE (ExxxII) | SEQ ID NO: 122, a LC/E with a di-isoleucine motif in C-terminal region di-isoleucine can substitute for leucine in the motif) |
| GFP-LCE (ExxxLL) | SEQ ID NO: 140, a LC/E with a di-leucine motif in C-terminal region |
| GFP-LCE Nterm LCA (ExxxII) | SEQ ID NO: 123, a LC/E with the first eight amino-acid of LC/A at the N-terminus and di-isoleucine motif in C-terminal region |
| GFP-LCE Nterm LCA (ExxxLL) | SEQ ID NO: 142, a LC/E with the first eight amino-acid of LC/A at the N-terminus and dileucine motif in C-terminal region |

All the chimeras expressed in SH-SY5Y are able to cleave $SNAP25_{206}$ into $SNAP25_{180}$, and they do not cleave the substrate at any other sites (FIG. 4). The preliminary data from the two experiments performed shows different levels of activity of the chimeras when compared to native LC/E. We could not distinguish if those differences are due to lower or higher levels of expression of the mutants, or to true changes on catalytic activity, because there was not enough material to run an immunoprecipitation to detect the chimeric LC/Es. FIG. 5 shows the results of a new set of three independent experiments transfecting the chimeric LC/Es into PC12 and SH-SY5Y cells. The levels of expression of each construct are different but all of them retain catalytic activity towards the cleavage of SNAP25. For some of the constructs the catalytic activity seemed diminished when compared with the wild-type LC/E but those changes can only be confirmed by expressing the protein recombinantly and performing ELISA or GFP assays.

Work previously published by Fernandez-Salas, Steward et al. (PNAS 101, 3208-3213, 2004) showed the sub-cellular localization of GFP-LC/A and GFP-LC/E proteins in differentiated PC-12 cells (FIG. 6). GFP-LC/A localized in a punctate manner in specific areas in the plasma membrane of the cell body and the neurites, with no localization of GFP-LC/A protein in the cytoplasm of the cells (FIG. 6A.). GFP-LC/E showed cytoplasmic localization with nuclear exclusion. Cells displayed rounded morphology and lack of neurites even in differentiation medium (FIG. 6B.).

The results in FIG. 6 demonstrate that the light chains from BoNT serotypes A and E are directed to distinct sub-cellular compartments. To identify sequences of importance in directing LC/A localization to the plasma membrane, PC-12 and SH-SY5Y cells were transiently transfected with GFP-LC/E and GFP-LC/E (N-LCA/ExxxLL) plasmid constructs. Transfected SH-SY5Y cells were selected in growth medium containing 0.5 mg/ml G418 for 2 days before staining with the Anti-SNAP25 and Anti-GFP antibodies. The transfected PC-12 cells were exposed to selection medium for 2 days followed by differentiation medium (containing NGF at 50 ng/ml final concentration) for 24 hours before staining.

Staining for the GFP portion of the LC/E chimera demonstrated that most of the GFP-LCE(N-LCA/ExxxLL) protein was localized at the plasma membrane in a punctuate manner (FIGS. 7A and C), similar to the previously reported GFP-LC/A localization (FIG. 6A). The mouse monoclonal antibodies to $SNAP25_{180}$ used in this staining have high background staining but the cells expressing LC/E displayed a stronger signal. Moreover, cells expressing the GFP-LCE (N-LCA/ExxxLL) chimera contain $SNAP25_{180}$ that remains in the cytoplasm.

GFP staining shown in FIGS. 8A and 8C demonstrates the punctate localization of GFP-LC/E (N-LCA/ExxxLL) protein at the plasma membrane of the cells, similar to the GFP-LC/A localization presented in FIG. 6A. The cells that are expressing the GFP-LC/E (N-LCA/ExxxLL) chimera protein (indicated by arrows corresponding to cells ‘a’, ‘b’ and ‘e’ min FIGS. 8A and 8C) do not show staining with Anti-$SNAP25_{206}$ antibody (cells ‘a’, ‘b’ and ‘e’ min FIGS. 8B and 8D). This confirms the proteolytic activity of the GFP-LC/E (N-LCA/ExxxLL) protein expressed in these cells, as demonstrated by its ability to cleave $SNAP25_{206}$. On the contrary, cells depicted ‘c’ and ‘d’ min FIG. 8C that are not expressing the GFP-LC/E (N-LCA/ExxxLL) protein give a good signal for the presence of full length SNAP25$_{206}$ protein as indicated by cells 'c' and 'd' min FIG. 8D.

Figure 6:
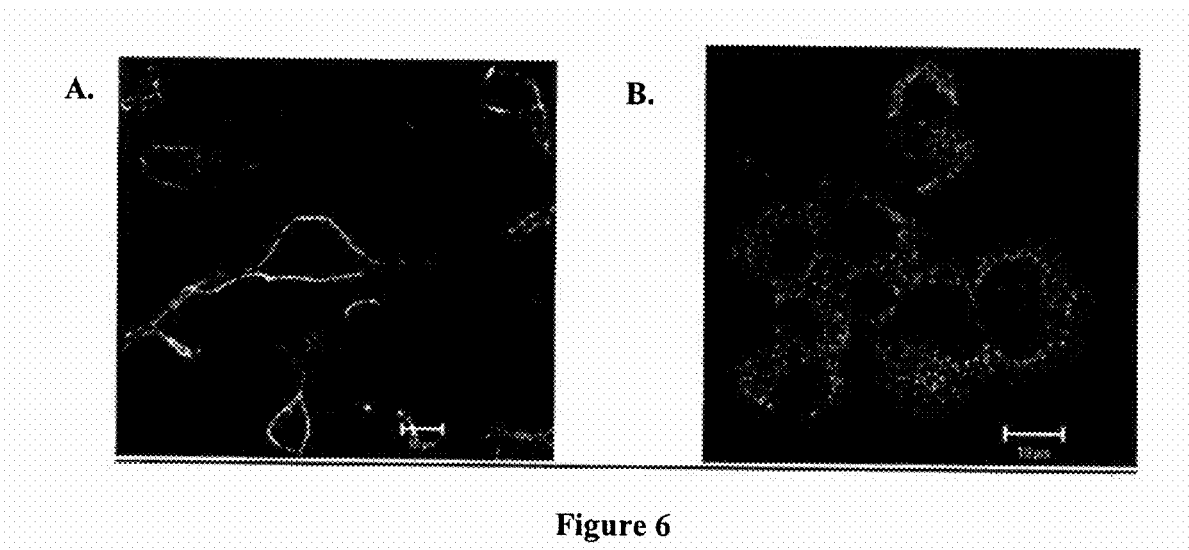
FIG. 6: Taken from PNAS publication (1). Differentiated PC-12 cells expressing GFP-LC/A (A) and GFP-LC/E (B).
Figure 7:
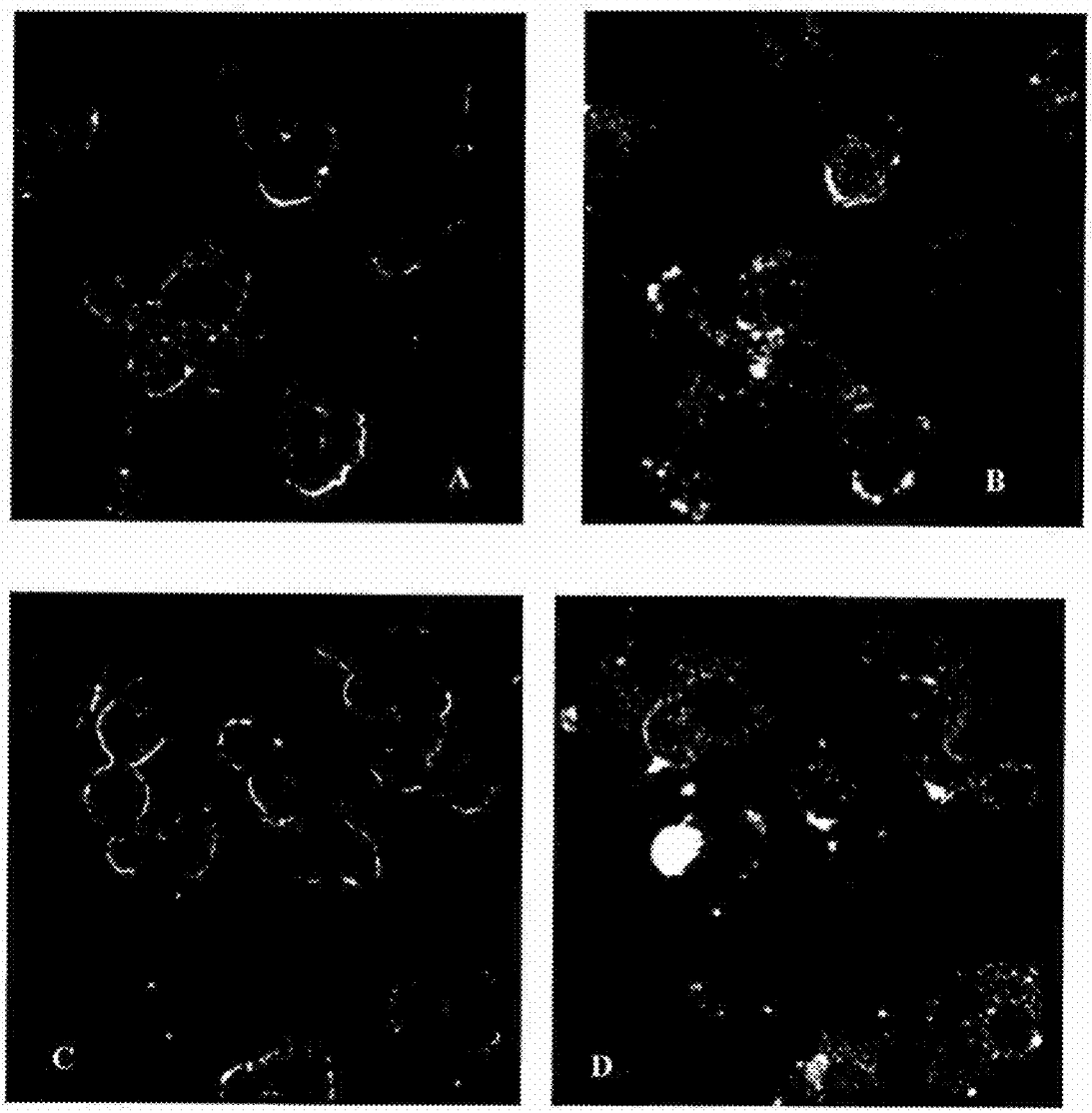
FIG. 7: Differentiated PC-12 cells transfected with GFP-LCE (N-LCA/ExxxLL). Immunostained with antibodies to GFP, rabbit polyclonal at 1:100 (FIGS. 7A and 7C) and a combination of three Anti-SNAP$_{180}$ mouse monoclonal antibodies (1A3A7, 1G8C11 and 1C9F3), each at 1:50 dilution (FIGS. 7B and 7D). (63× magnification).
Figure 9:
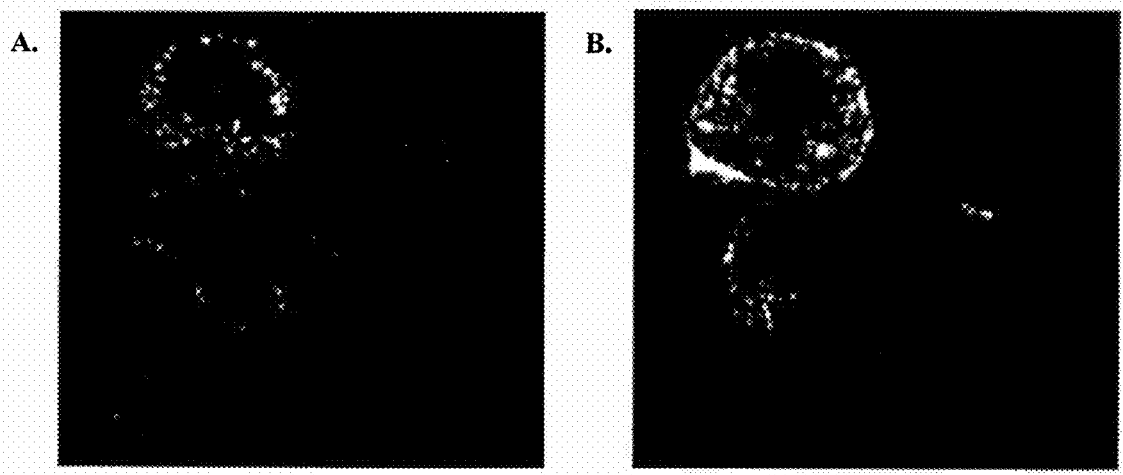
FIG. 9: Differentiated PC-12 cells transfected with native beluga GFP-LC/E, and immunostained with rabbit polyclonal antibodies to GFP (FIG. 9A) and 1:1:1 combination of anti-SNAP25$_{180}$ mouse monoclonal antibodies, each at 1:50 dilution (FIG. 9B) (63× magnification) as used in the previous figure with the chimeric LC/E. Both images correspond to the same cell but are not from the same plane.

The GFP-LC/E protein is shown to localize to a structure within the cytoplasm in a punctate manner as previously reported in Fernandez-Salas, Steward et al. and Fernandez-Salas, Ho et al. (Movement Disorders 19, S23-S34., 2004) and shown in FIG. 6B. SNAP25$_{180}$ protein also localizes in the cytoplasm of cells expressing GFP-LCE and appears to be in a granular structure (FIG. 9B).

SH-SY5Y Localization of GFP-LC/E

Figure 10:
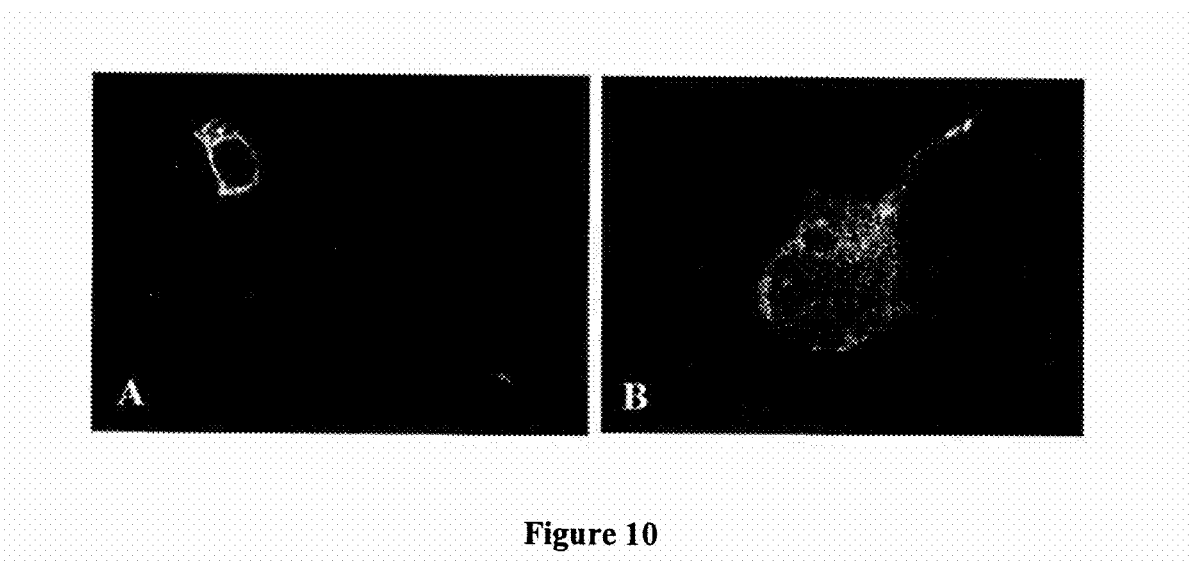
FIG. 10: SH-SY5Y cells transfected with GFP-LCE construct and stained with anti-GFP, rabbit polyclonal at a dilution of 1:100 and secondary anti-rabbit at 1:200. (63× magnification). A and B represent two different cells from the same transfection experiment.

GFP-LC/E protein localizes in the cytoplasm of SH-SY5Y cells. Notice the large area of GFP exclusion in the nuclei of both cells shown in FIG. 10.

Figure 11:
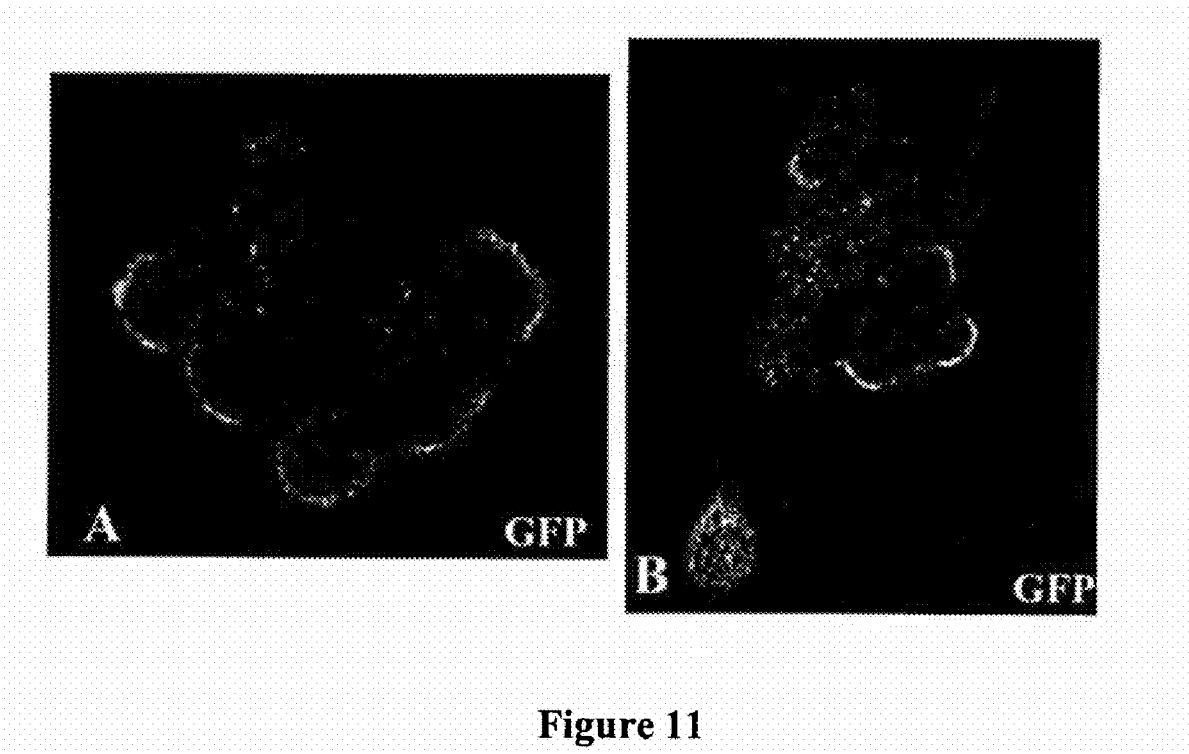
FIG. 11: SH-SY5Y cells transfected with GFP-LCE (N-LCA/ExxxLL) and stained with anti-GFP antibodies. (63× magnification). A and B are different groups of cells from the same transfection experiment.

The GFP-LCE (N-LCA/ExxxLL) chimera was also expressed in SH-SY5Y cells. Staining with an anti-GFP antibody (FIG. 11) demonstrated localization at the plasma membrane, similar to that seen for the chimera expressed in PC-12 cells.

Figure 12:
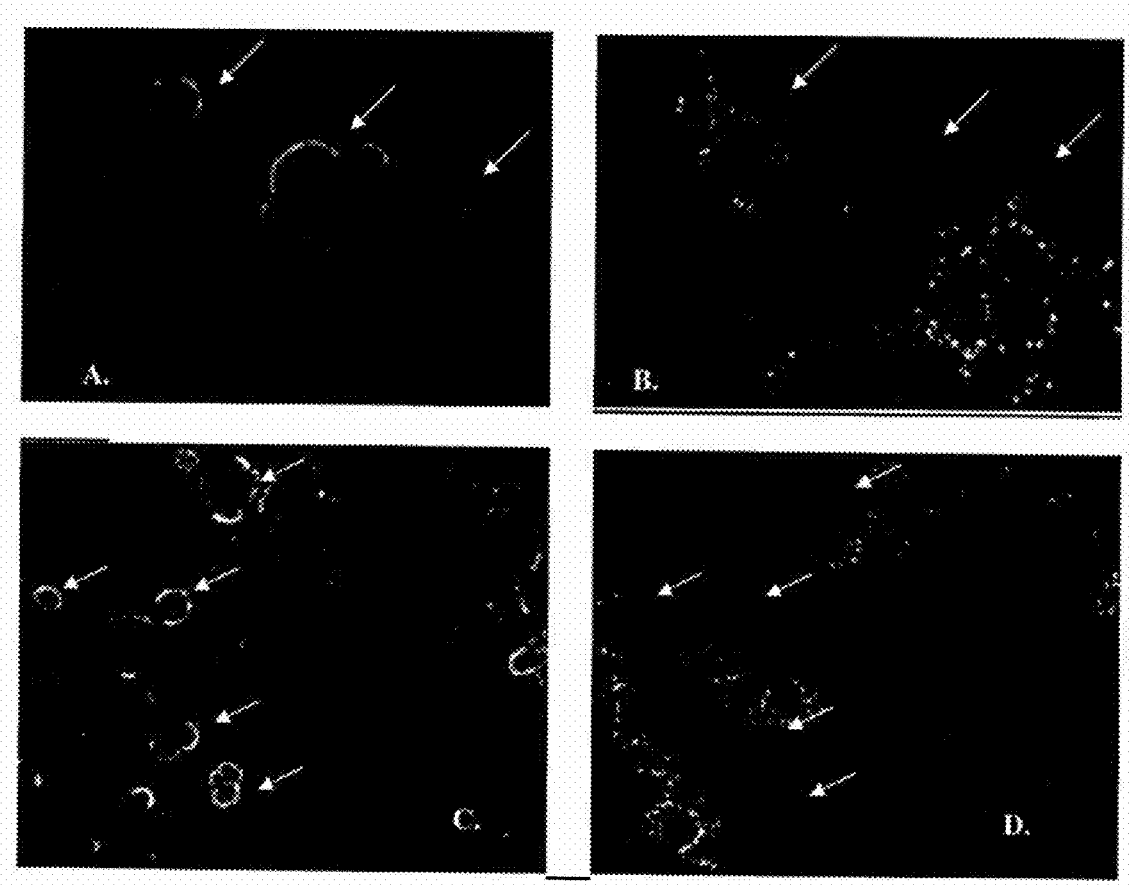
FIG. 12: SH-SY5Y cells transfected with GFP-LCE (N-LCA/ExxxLL). Cells were immunostained with antibodies to anti-GFP (FIGS. 12A and 12C) and uncleaved SNAP25$_{206}$ (FIGS. 12B & 12D). (63× magnification).

The plasmid encoding chimeric GFP-LC/E (N-LCA/ExxxLL) was transfected into the human neuroblastoma cell line SH-SY5Y. The chimeric protein was expressed and dishes were fixed for immunostaining. Cells stained positive for GFP (monoclonal antibody) (indicated by arrows in FIGS. 12A and 12C) show the GFP-LCE (N-LCA/ExxxLL) protein localized to the plasma membrane. Full length SNAP25$_{206}$ protein is not detected in cells expressing the GFP-LCE (N-LCA/ExxxLL) protein as indicated by the arrows in FIGS. 12B and 12D. This suggests the GFP-LCE (N-LCA/ExxxLL) chimera protein is functional and cleaves SNAP25$_{206}$.

Figure 13:
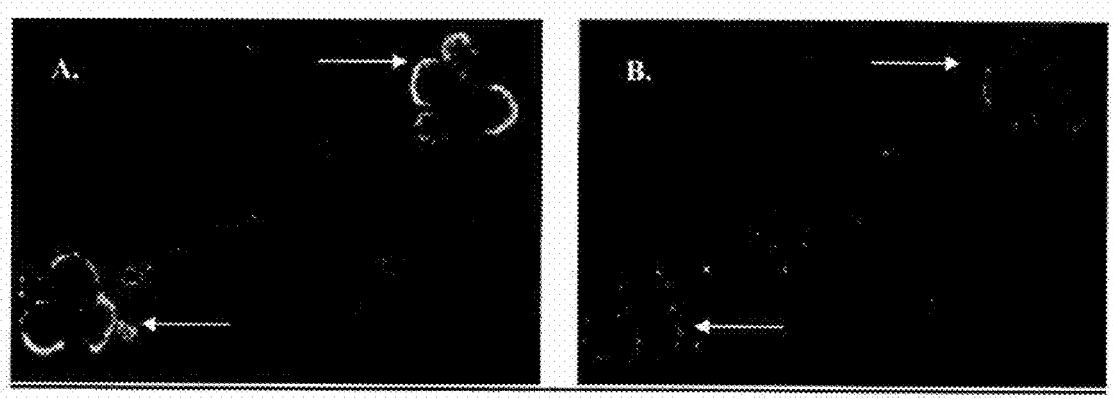
FIG. 13: SH-SY5Y cells transfected with GFP-LC/E (N-LCA/ExxxLL). Cells were immunostained with antibodies to GFP (FIG. 13A) and 1A3A7 mouse monoclonal antibody specific for SNAP25$_{180}$ (FIG. 13B). (63× mag).

To further confirm activity the transfected cells were also stained with the GFP and the monoclonal antibodies to SNAP25$_{180}$. Staining for GFP (polyclonal antibody) showed the GFP-LC/E (N-LCA/ExxxLL) protein localized at the plasma membrane as shown in the previous figure (FIG. 13A). The 1A3A7 ascites mouse monoclonal antibody used to stain SNAP25$_{180}$ has high background staining and is very weak (arrows in FIG. 13B indicate groups of cells positive for SNAP25$_{180}$ staining. This antibody was used at 1:100 dilution in this early experiment. However, cells expressing the GFP-LCE (N-LCA/ExxxLL) protein in FIG. 13A contain SNAP25$_{180}$ in the cytoplasm as indicated by arrows in FIG. 13B.

The GFP-LC/E fusion protein has previously been demonstrated to localize in the cytoplasm of PC12, HIT-T15, and HeLa cells. Adding the N-terminal LC/A signal (8 amino acids of SEQ ID NO: 120) and the C-terminal di-leucine motif of LC/A (SEQ ID NO: 145) into the LCE protein sequence (GFP-LCE (N-LCA/ExxxLL) dramatically changed the sub-cellular localization of LC/E. Adding the LC/A localization signals to LC/E directed localization of the LC/E (N-LCA/ExxxLL) chimera to the plasma membrane, validating these motifs/sequences as important signals for LC/A localization. Cleavage of SNAP25 by LC/E was detected using antibodies to the N-terminus of SNAP25. Co-staining with antibodies to full length SNAP25$_{206}$ demonstrated a loss of intact SNAP25 in cells expressing the functional GFP-LCE (N-LCA/ExxxLL) chimera protein. SNAP25$_{180}$ protein was also detected in the cytoplasm of cells expressing GFP-LCE (N-LCA/ExxxLL), indicating LC/E SNAP25 proteolysis. Further work will need to be done to optimize staining of SNAP25$_{180}$ cleavage product in the paraformaldehyde fixed cells because the anti-SNAP25$_{180}$ antibodies used in this study were weak. To identify compartments where the LC/A, LC/E and LC/E (N-LCA/ExxxLL) proteins reside, a panel of dyes and antibodies specific for cytoplasmic organelles and plasma membrane proteins (channels and receptors) will be employed. PC-12 cells have been transfected with wild-type GFP-LC/E, GFP-LC/E (ExxxLL), GFP-LC/E (ExxxII), GFP-LC/E (N-LCA), GFP-LC/E (N-LCA/ExxxII) and wild-type GFP-LC/A constructs. Localization of these chimera proteins will confirm sequences of importance in LC/A localization. The LC/E chimera containing the N-terminus of the LC/A and the di-leucine motif presents a very distinct localization and may constitute a LC/E with a longer duration of action.

While this invention has been described with respect to various specific examples and embodiments, it is to be understood that the invention is not limited thereto and that it can be variously practiced with the scope of the following claims. All articles, references, publications, and patents set forth above are incorporated herein by reference in their entireties.

What is claimed is:

1. A nucleic acid comprising a region that encodes a modified toxin comprising a modified light chain of a botulinum toxin type E, wherein the modification to the botulinum toxin type E light chain is the addition of one or more amino acid sequences comprising SEQ ID NO: 120 within the N-terminal 30 amino acids of a wild-type botulinum toxin type E light chain of SEQ ID NO: 136 and the addition of one or more leucine-based motifs of SEQ ID NO: 112 within the C-terminal 50 amino acids of a wild-type botulinum toxin type E light chain of SEQ ID NO: 136,
  wherein the addition of the amino acid sequence comprising SEQ ID NO: 120 increases biological half-life of the modified toxin relative to an identical modified toxin without the additional amino acid sequence comprising SEQ ID NO: 120, and,
  wherein the addition of the leucine-based motif of SEQ ID NO: 112 increases biological half-life of the modified toxin relative to an identical modified toxin without the additional leucine-based motif comprising SEQ ID NO: 112.

2. The nucleic acid of claim 1, wherein the addition of one or more amino acid sequences comprising SEQ ID NO: 120 to the encoded modified toxin is within the first 12 amino acids of the N-terminal of a wild-type botulinum toxin type E light chain of SEQ ID NO: 136, and the addition of one or more leucine-based motifs of SEQ ID NO: 112 is within the last 27 amino acids of the C-terminal of a wild-type botulinum toxin type E chain of SEQ ID NO: 136.

3. The nucleic acid of claim 1, wherein the addition of one or more amino acid sequences comprising SEQ ID NO: 120 to the encoded modified toxin is within the first 8 amino acids of the N-terminal of a wild-type botulinum toxin type E light chain of SEQ ID NO: 136, and the addition of one or more leucine-based motifs of SEQ ID NO: 112 is within the last 23 amino acids of the C-terminal of a wild-type botulinum toxin type E light chain of SEQ ID NO: 136.

4. The nucleic acid of claim 1, wherein the addition of one or more amino acid sequences comprising SEQ ID NO: 120 to the encoded modified toxin is within the first 8 amino acids of the N-terminal of a wild-type botulinum toxin type E light chain of SEQ ID NO: 136; and the addition of one or more leucine-based motifs of SEQ ID NO: 112 is prior to the last 16 amino acids at the C-terminal of a wild-type botulinum toxin type E light chain of SEQ ID NO: 136.

5. The nucleic acid of claim 1, 2, 3, or 4, wherein the encoded modified toxin further comprises a heavy chain of a Clostridial toxin.

6. The nucleic acid of claim 5, wherein the heavy chain is a heavy chain of a botulinum toxin type A, botulinum toxin type B, botulinum toxin type C1, botulinum toxin type D, botulinum toxin type E, botulinum toxin type F, or botulinum toxin type G.

7. The nucleic acid of claim 5, wherein the heavy chain is a heavy chain of a botulinum toxin type A.

8. The nucleic acid of claim 5, wherein the heavy chain is a heavy chain of a botulinum toxin type E.

9. The nucleic acid of claim 1, wherein the leucine-based motif added to the encoded modified toxin is SEQ ID NO: 1, SEQ ID NO: 4, SEQ ID NO: 6, or SEQ ID NO: 13.

10. The nucleic acid of claim 1, wherein the encoded modified botulinum toxin type E light chain is SEQ ID NO: 126.

11. The nucleic acid of claim 1, wherein the encoded modified botulinum toxin type E light chain is SEQ ID NO: 131.

12. A nucleic acid comprising a region that encodes a modified toxin comprising a modified light chain of SEQ ID NO: 136, wherein one or more of SEQ ID NO: 120 occur within the N-terminal 30 amino acids of the light chain, and one or more of SEQ ID NO: 112 occur within the C-terminal 50 amino acids of the light chain, wherein the addition of one or more SEQ ID NO: 120 increases biological half-life of the modified toxin relative to an identical modified toxin without the addition of one or more SEQ ID NO: 120, and, wherein the addition of one or more SEQ ID NO: 112 increases biological half-life of the modified toxin relative to an identical modified toxin without the addition of one or more SEQ ID NO: 112.

* * * * *

UNITED STATES PATENT AND TRADEMARK OFFICE
CERTIFICATE OF CORRECTION

PATENT NO. : 8,008,465 B2
APPLICATION NO. : 12/684745
DATED : August 30, 2011
INVENTOR(S) : Ester Fernandez-Salas et al.

It is certified that error appears in the above-identified patent and that said Letters Patent is hereby corrected as shown below:

On page 2, in column 1, under "Other Publications", line 1, delete "botulinium" and insert -- botulinum --, therefor.

On page 2, in column 1, under "Other Publications", line 13, delete "bindng" and insert -- binding --, therefor.

On page 2, in column 1, under "Other Publications", line 16, delete "Botlinum" and insert -- botulinum --, therefor.

On page 2, in column 1, under "Other Publications", line 29, delete "botuinum" and insert -- botulinum --, therefor.

In column 1, line 49, delete "writers" and insert -- writer's --, therefor.

In column 2, line 54, delete "aspargine," and insert -- asparagine, --, therefor.

In column 8, line 41, delete "aspargine," and insert -- asparagine, --, therefor.

In column 10, line 7, delete "myristylated" and insert -- myristoylated --, therefor.

In column 10, line 53, delete "unctuate" and insert -- punctuate --, therefor.

In column 10, line 55, delete "unctuate" and insert -- punctuate --, therefor.

In column 12, line 10, delete "torticolis," and insert -- torticollis, --, therefor.

In column 14, line 23, delete "that that" and insert -- than that --, therefor.

In column 19, line 6, delete "HaIIA," and insert -- HallA, --, therefor.

Signed and Sealed this
Twenty-eighth Day of February, 2012

David J. Kappos
*Director of the United States Patent and Trademark Office*

CERTIFICATE OF CORRECTION (continued)
U.S. Pat. No. 8,008,465 B2

In column 21, line 66, delete "whereby" and insert -- thereby --, therefor.

In column 25-26, line 2, Seq. Id No. 68, delete "MMEPPFARST" and insert -- MMEPPFARGT --, therefor.

In column 25-26, line 1, Seq. Id No. 69, delete "YTIEESFNISDKNMSKEYRSQ" and insert -- YTIEEGFNISDKNMGKEYRGQ --, therefor.

In column 25-26, line 1, Seq. Id No. 71, delete "NIPKSNLNVLFMSQNLSRN" and insert -- NIPKSNLNVLFMGQNLSRN --, therefor.

In column 25-26, line 3, Seq. Id No. 71, delete "CHKAIDSRSLYNK" and insert -- CHKAIDGRSLYNK --, therefor.

In column 25-26, line 1-2, Seq. Id No. 73, delete "YTIRDSFNLTNKSFNIENSSQNIERNPALQKL" and insert -- YTIRDGFNLTNKGFNIENSGQNIERNPALQKL --, therefor.

In column 25-26, line 1-3, Seq. Id No. 75, delete "GYNINNLKVNFRSQNANLNPRIITPITS RSLVKKAAAACKNIVSVKSIRK" and insert -- GYNINNLKVNFRGQNANLNPRIIT PITGRGLVKKAAAACKNIVSVKGIRK --, therefor.

In column 25-26, line 2, Seq. Id No. 76, delete "LYIKPSSCQEFY" and insert -- LYIKPGGCQEFY --, therefor.

In column 25-26, line 1-3, Seq. Id No. 77, delete "GYNINNLKVNFRSQNANLNPRIITPITSRSLV---HRFCKNIVSVKSIRK" and insert -- GYNINNLKVNFRGQNANLNPRIITPITGRGLV---HRFCKNIVSVKGIRK --, therefor.

In column 25-26, line 1, Seq. Id No. 79, delete "GYNINNLKVNFRSQNANLN" and insert -- GYNINNLKVNFRGQNANLN --, therefor.

In column 28, line 45, delete "persistance" and insert -- persistence --, therefor.

In column 28, line 48, delete "persistance" and insert -- persistence --, therefor.

In column 28, line 51-52, delete "persistance" and insert -- persistence --, therefor.

In column 28, line 55, delete "persistance" and insert -- persistence --, therefor.

In column 35, line 39, delete "TIILY" and insert -- TILY --, therefor.

In column 37, line 21, delete "Denaturalizat:" and insert -- Denaturalization: --, therefor.

In column 39-40, line 10, delete "rabbitpolyclonal" and insert -- rabbit polyclonal --, therefor.

CERTIFICATE OF CORRECTION (continued)
U.S. Pat. No. 8,008,465 B2

In column 41, line 14, delete "Burlingham," and insert -- Burlingame, --, therefor.

In column 41, line 16, delete "microscope" and insert -- microscope. --, therefor.

In column 42, line 17, delete "6B.)." and insert -- 6B). --, therefor.

In column 42, line 61, delete "min" and insert -- in --, therefor.

In column 42, line 62, delete "min" and insert -- in --, therefor.

In column 42, line 66, delete "min" and insert -- in --, therefor.

In column 43, line 2, delete "min" and insert -- in --, therefor.

In column 157-158, line 7, delete "(7)" and insert -- (6) --, therefor.

In column 157-158, line 7, delete "(7)" and insert -- (6) --, therefor.

In column 165-166, line 7, delete "(7)" and insert -- (6) --, therefor.